(12) United States Patent
Graham et al.

(10) Patent No.: US 10,035,847 B2
(45) Date of Patent: Jul. 31, 2018

(54) AMYLOID PROTOFIBRIL ANTIBODIES AND METHODS OF USE THEREOF

(71) Applicant: The Rockefeller University, New York, NY (US)

(72) Inventors: W. Vallen Graham, New York, NY (US); Thomas P. Sakmar, New York, NY (US)

(73) Assignee: THE ROCKEFELLER UNIVERSITY, New York, NY (US)

( * ) Notice: Subject to any disclaimer, the term of this patent is extended or adjusted under 35 U.S.C. 154(b) by 0 days.

(21) Appl. No.: 15/026,545

(22) PCT Filed: Oct. 2, 2014

(86) PCT No.: PCT/US2014/058880
§ 371 (c)(1),
(2) Date: Mar. 31, 2016

(87) PCT Pub. No.: WO2015/051159
PCT Pub. Date: Apr. 9, 2015

(65) Prior Publication Data
US 2016/0251419 A1    Sep. 1, 2016

Related U.S. Application Data

(60) Provisional application No. 61/885,593, filed on Oct. 2, 2013.

(51) Int. Cl.
C07K 14/47    (2006.01)
C07K 16/18    (2006.01)
A61K 49/00    (2006.01)

(52) U.S. Cl.
CPC .......... C07K 16/18 (2013.01); A61K 49/0004 (2013.01); C07K 14/4711 (2013.01);
(Continued)

(58) Field of Classification Search
CPC .................. C07K 16/18; C07K 14/4711; C07K 2317/21; C07K 2317/24; C07K 2317/31;
(Continued)

(56) References Cited

U.S. PATENT DOCUMENTS 5,693,761 A    12/1997  Queen et al.
7,244,429 B2    7/2007  Zhou et al.
(Continued)

FOREIGN PATENT DOCUMENTS

WO    2010009330 A1    1/2010
WO    2012136552 A1    10/2012

OTHER PUBLICATIONS

Brettschneider S et al. Decreased serum amyloid beta 1-42 autoantibody levels in Alzheimer's disease, determined by a newly developed immuno-precipitation assay with radiolabeled amyloid beta 1-42 peptide. Biol. Psychiatry, 2005, 57:813-816.*
(Continued)

*Primary Examiner* — Kimberly Ballard
(74) *Attorney, Agent, or Firm* — Thompson Coburn LLP; Charles P. Romano

(57) ABSTRACT

The invention relates to methods for obtaining antibodies that recognize amyloid protofibrils and antibodies that recognize one or more amyloid protofibrils. Also provided are methods of using the antibodies to prevent or inhibit amyloid disease in a subject, to diagnose amyloid disease in a subject, and to detect amyloid protofibrils in a sample.

16 Claims, 38 Drawing Sheets

(52) U.S. Cl.
CPC ...... *C07K 2317/21* (2013.01); *C07K 2317/24* (2013.01); *C07K 2317/31* (2013.01); *C07K 2317/33* (2013.01)

(58) Field of Classification Search
CPC ............ C07K 2317/33; C07K 2317/34; A61K 49/0004; A61K 49/06; G01N 33/58–33/583; G01N 33/6896; G01N 2333/4709; G01N 2333/4727
See application file for complete search history.

(56) References Cited

U.S. PATENT DOCUMENTS

| | | | |
|---|---|---|---|
| 7,741,448 | B2 | 6/2010 | Yanagisawa et al. |
| 7,777,017 | B2 | 8/2010 | Stinson et al. |
| 7,875,704 | B2 | 1/2011 | Stassen et al. |
| 7,888,483 | B2 | 2/2011 | Cohen et al. |
| 8,043,620 | B2 | 10/2011 | Qian et al. |
| 8,062,635 | B2 | 11/2011 | Hattori et al. |
| 8,080,243 | B2 | 12/2011 | Liang et al. |
| 8,084,585 | B2 | 12/2011 | Kamogawa et al. |
| 8,221,754 | B2 | 7/2012 | Kanayama et al. |
| 8,309,094 | B2 | 11/2012 | Gerber et al. |
| 8,329,173 | B2 | 12/2012 | Goetsch |
| 8,383,350 | B1 | 2/2013 | Kolz et al. |
| 8,481,687 | B2 | 7/2013 | Vincent et al. |
| 8,496,937 | B2 | 7/2013 | Schneider et al. |
| 2004/0223909 | A1 | 11/2004 | Montalto et al. |
| 2006/0079447 | A1* | 4/2006 | Wetzel ............... A61K 31/4164 514/1.1 |
| 2006/0280733 | A1* | 12/2006 | Kayed ................ A61K 39/0007 424/133.1 |
| 2007/0189967 | A1 | 8/2007 | Siclovan et al. |
| 2008/0131907 | A1 | 6/2008 | Wang et al. |
| 2010/0031377 | A1 | 2/2010 | Schenk et al. |
| 2010/0209422 | A1 | 8/2010 | Ravetch et al. |
| 2012/0183527 | A1* | 7/2012 | Relkin ................... C07K 16/18 424/130.1 |

OTHER PUBLICATIONS

Gupta R et al. Halting the amyloid march: How a novel Ca2+-binding protein, NUCB1, prevents the formation of amyloid fibrils. Biophysical J. 2011, 100(3, Suppl. 1):538, Meeting abstract 2926-Pos.*
Agdeppa et al., "A Review of Imaging Agent Development", The American Association of Pharmaceutical Scientists Journal, Jun. 2009, pp. 286-299, vol. 11, No. 2.
Gupta et al., "Nucleobindin 1 Caps Human Islet Amyloid Polypeptide Protofibrils to Prevent Amyloid Fibril Formation", Journal of Molecular Biology, Aug. 10, 2012, pp. 378-389, vol. 421 Nos. 2-3.
Gupta, "Study of Factors Affecting Amylin Fibril Formation and the Characterization of a Protein Which Prevents Amyloidogenesis", The Graduate School in Partial Fulfillment of Requirements for the Degree of Doctor of Philosophy in Chemistry, Stony Brook University, Aug. 2008, 279 pages.
International Search Report and Written Opinion for PCT/US2014/058880 dated Mar. 3, 2015.
Kayed et al., "Fibril Specific, Conformation Dependent Antibodies Recognize a Generic Epitope Common to Amyloid Fibrils and Fibrillar Oligomers that is Absent in Prefibrillar Oligomers", Molecular Neurodegeneration, 2007, pp. 1-11, vol. 2, No. 18.
Lin et al., "Calnuc Binds to Alzheimer's b-amyloid Precursor Protein and Affects its Biogenesis", Journal of Neurochemistry, 2007, pp. 1505-1514, vol. 100.
Miura et al., "Molecular Cloning of Nucleobindin, a Novel DNA-Binding Protein that Contains Both a Signal Peptide and a Leucine Zipper Structure", Biochemical and Biophysical Research Communications, Aug. 31, 1992, pp. 375-380, vol. 187, No. 1.
O'Nuallain et al., "Anti-Amyloidogenic Activity of IgGs Contained in Normal Plasma", Journal of Clinical Immunology, 2010, pp. S37-S42, vol. 30, Suppl. 1.
O'Nuallain et al., "Human Plasma Contains Cross-Reactive Ab Conformer-Specific IgG Antibodies", Biochemistry, 2008, pp. 12254-12256, vol. 47, No. 47.
Cerf et al., "High Ability of Apolipoprotein E4 to Stabilize Amyloid-β Peptide Oligomers, the Pathological Entities Responsible for Alzheimer's Disease", The FASEB Journal, Nov. 2017, pp. 1585-1595, vol. 25, No. 5.
Conway, et al., "Kinetic Stabilization of the α-Synuclein Protofibril by a Dopamine-α-Synuclein Adduct", Science, Nov. 2001, pp. 1346-1349, vol. 294.
Guivernau, et al., "Amyloid-β Peptide Nitrotyrosination Stabilizes Oligomers and Enhances NMDAR-Mediated Toxicity", The Journal of Neuroscience, Nov. 16, 2016, pp. 11693-11703, vol. 36, No. 46.
Hawkes, et al., "Small Molecule -β-amyloid Inhibitors that Stabilize Protofibrillar Structures in vitro Improve Cognition and Pathology in a Mouse Model of Alzheimer's Disease", European Journal of Neuroscience, 2010, pp. 203-213, vol. 31.
Hayden, et al., "Herne Stabilization of a-Synuclein Olgomers During Amyloid Fibril Formation", BioChemistry, Aug. 4, 2015, pp. 4599-4610, vol. 54, No. 30.
Hayden, et al., "Preparation of Pure Populations of Covalently Stabilized Amyloid β-Protein Oilgomers of Specific Sizes", Analytical Biochemistry, 2017, pp. 78-85, vol. 518.
Johansson, et al., "Docosahexaenoic Acid Stabilizes Soluble Amyloid-β Protofibrils and Sustains Amyloid-β-Induced Neurotoxicity in vitro", FEBS Journal, 2007, pp. 990-1000.
Ryan, et al., "Stabilization of Nontoxic Aβ-Oligomers: Insights into the Mechanism of Action of Hydroxyquinolines in Alzheimer's Disease", Neurobiology of Disease, Feb. 18, 2015, pp. 2871-2884, vol. 35, No. 7.
Sandberg, et al., "Stabilization of Neurotoxic Alzheimer Amyloid-β Oligomers by Protein Engineering", PNAS, Aug. 31, 2010, pp. 15595-15600, vol. 107, No. 35.
Williams, et al., "Structural Properties of Aβ Protofribils Stabilized by a Small Molecule", PNAS, May 17, 2005, pp. 7115-7120, vol. 102, No. 20.
Williams, et al., "Stabilization of Native Amyloid β-Protein Oligomers by Copper and Hydrogen Peroxide Induced Cross-linking of Unmodified Proteins (CHICUP)", Biochem Biophys, Mar. 2016, pp. 249-259, vol. 1864, Issue. 3.

* cited by examiner

|  | Size | Solubility | Toxicity |
|---|---|---|---|
| monomer | 2 nm [A] | yes | no |
| oligomer | 10 nm [B] | yes [E] | yes [G] |
| protofibril | 100 nm [B,C] | yes [F] | yes [G] |
| fibril | 1 μm [B] | no [F] | yes [G] |
| plaque | 50 μm [B] | no [F] | yes [H] |
| *NUCB1-capped protofibril antigen* | 40-100 nm [D] | yes [D] | no [D] |

A Erickson HP, Biol Proced Olnine, 11(32-51) 2009
B Knowles and Buehler, Nature Nanotechnology 6, 469-79, 2011
C Dubnovitsky A et al, Plos One, 8(7) 2013
D Gupta R et al, J Mol Biol 421(2-3) 2012
E Kayed R et al, Science, 300(5618) 2003
F Nichols MR et al, JBC, 280 (2471-2480), 2004
G Lee YJ et al, Plos One, 6(5) 2011
H Meyer-Luehmann M et al Nature, 451(7179) 2008

Figure 2

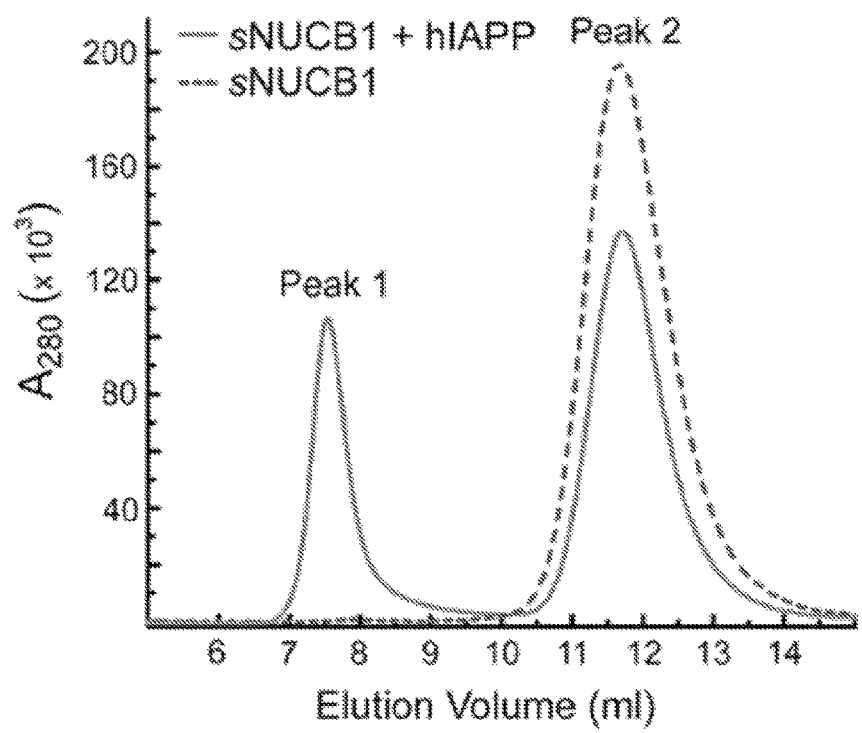
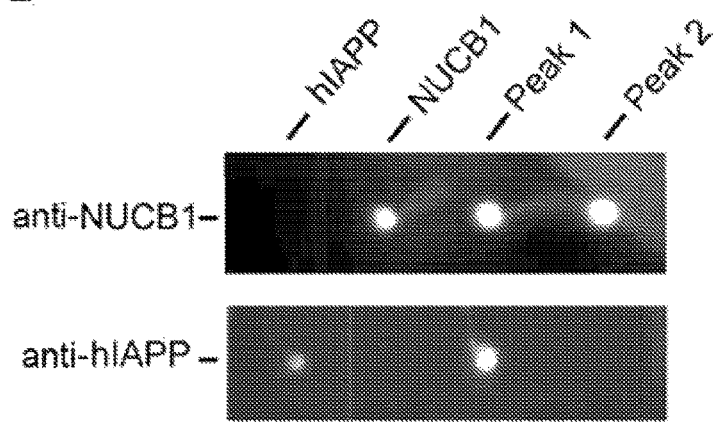
Figure 3 A,B

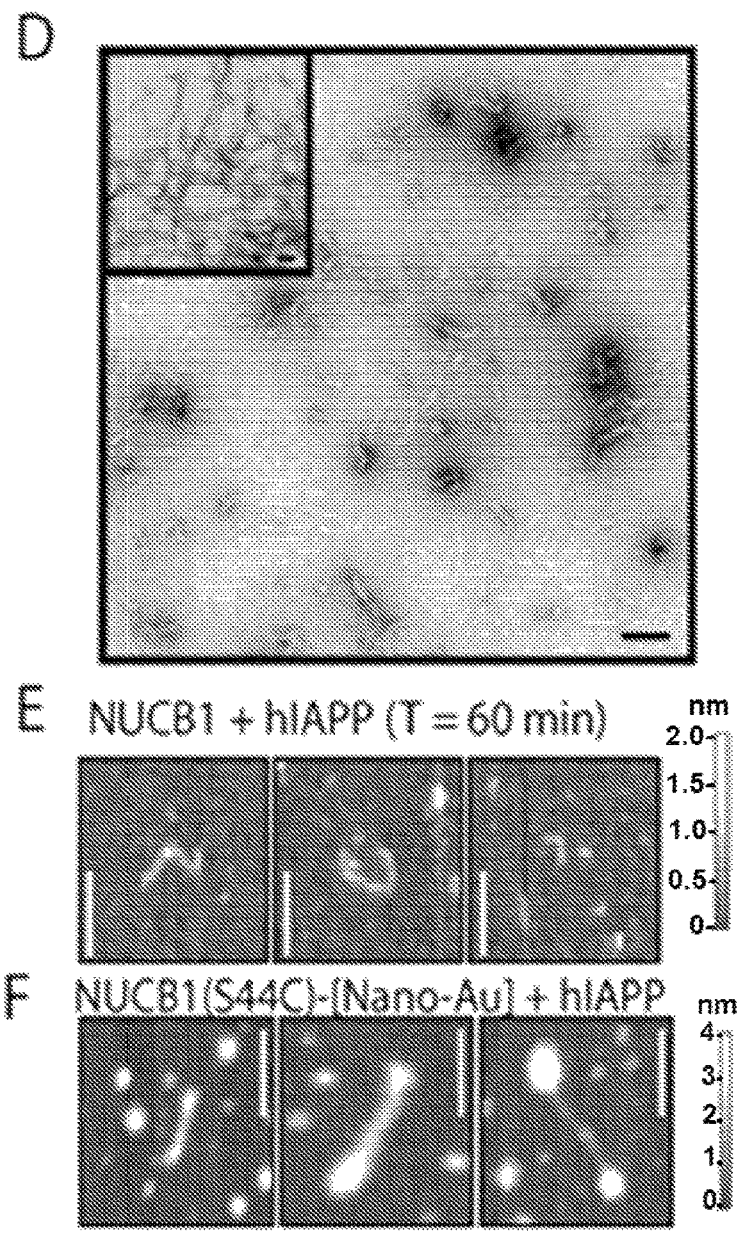
Figure 3 D,E,F

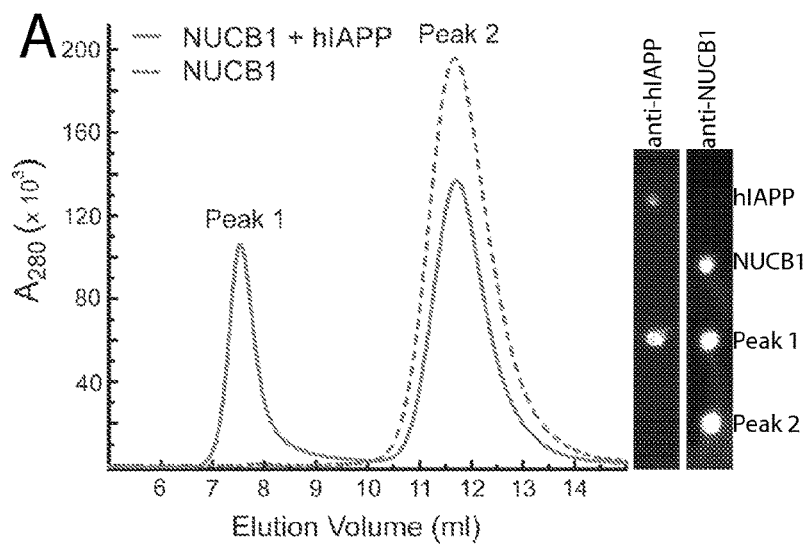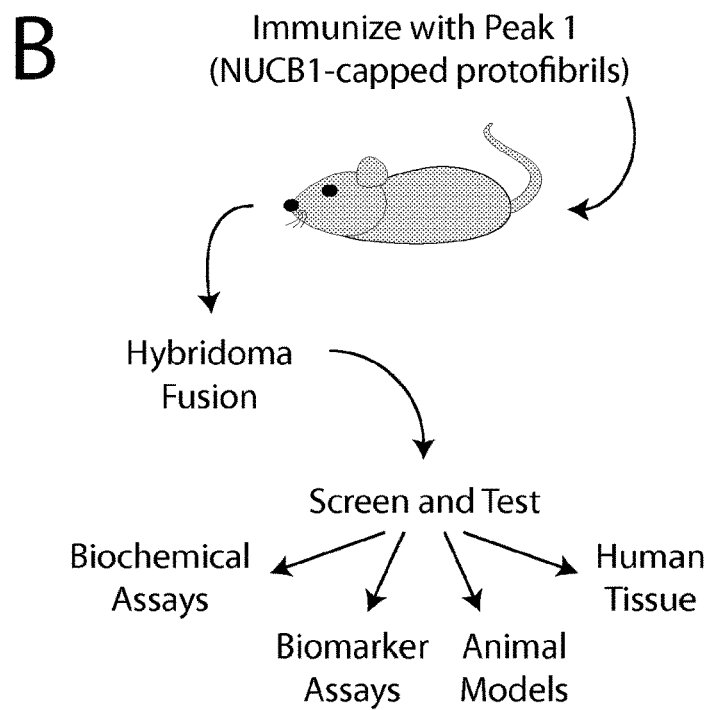
Figure 4 A,B

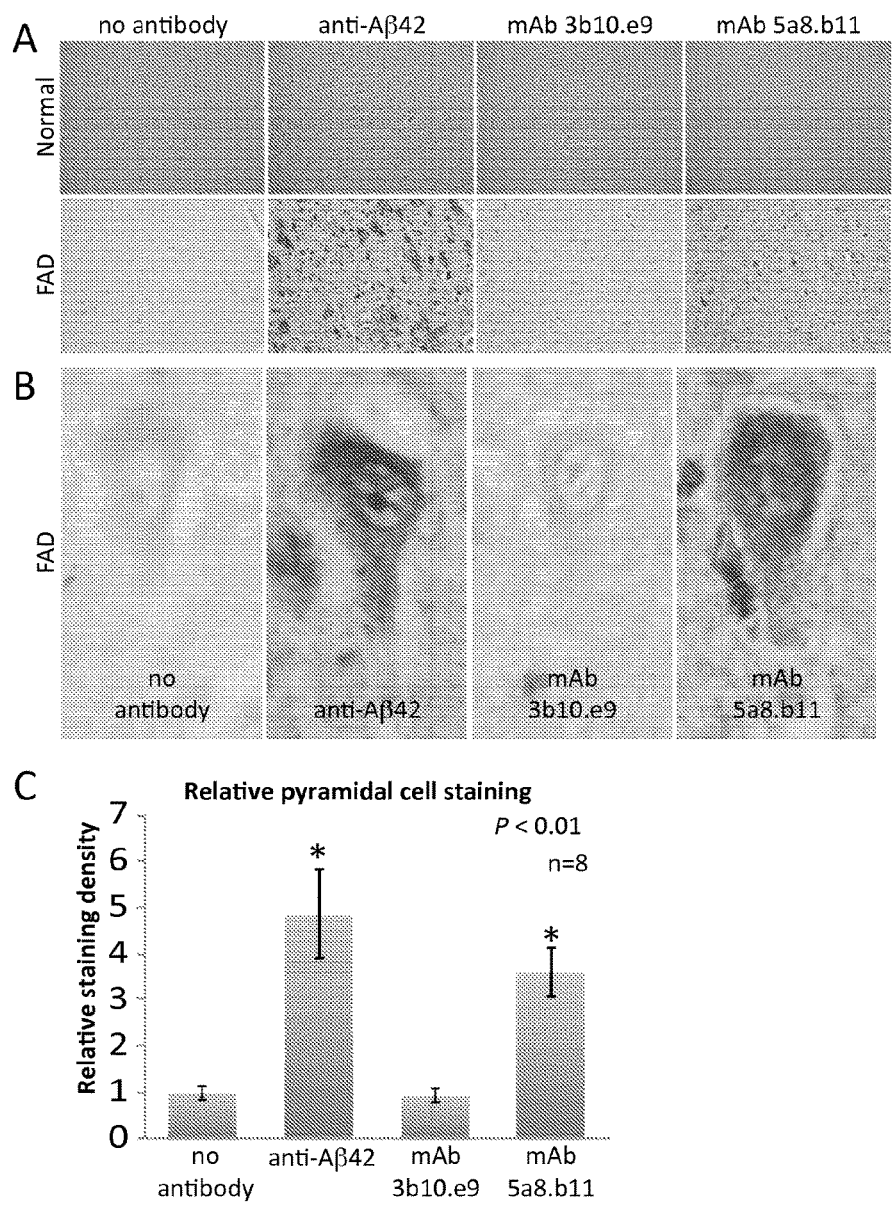
Figure 6 A,B,C

Heavy Chains

```
7b6.b12    EVQLQESGAELVKPGASVKISCKVSGYTFTDHTIHWMKQRPEQGLEWIGYIYPRDG--
ST
5c9.a2     EVQLQESGPVLVKPGASVKMSCKASGYTFTDYYMNWVKQSHGKSLEWIGVINPYNG--
GT
5a8.b11    EVQLQESGPELVKPGASVKIPCKASGYTFTDYNMDWVKQSHGKSLEWIGDINPNNG--
GT
4b1.h9     EVQLQESGPVLVKPGASVKMSCKASGYTFTDYYMNWVKQSHGKSLEWIGVINPYNG--
GT
4a8.e11    EVQLQESGGGLVKPGGSLKLSCAASGFTFSDYGMHWVRQAPEKGLEWVAYISSGSS--
TV
3f2.e10
EVQLQESGGGLVQPKGSLKLSCAASGFSFNTYAMNWVRQAPGKGLEWVARIRSKSNNYAT

KYNEKFKGKATLTADKSSSTAYMQLNSLTSEDSAVYFCAR-PYDYAWFAYWGQGTLVTVSA
SYNQKFKGKATLTVDKSSSTAYMELNSLTSEDSAVYYCASLRRRTDYFDYWGQGTTLTVSS
IYNQKFKGKATLTVDKSSSTAYMELRSLTSEDTAVYYCA--RKGERGFDYWGQGTTLTVSS
SYNQKFKGKATLTVDKSSSTAYMELNSLTSEDSAVYYCA--RRRGYAMDYWGQGTSVTVSS
YCADTVKGRFTISRDNAKNTLFLQMTSLRSEDTAMYYCARR---WGYFDYWGQGTTLTVSS
YYADSVKDRFTISRDDSESMLYLQMNNLKTEDTAMYYCVR----LGAMDYWGQGTSVTVSS
```

Light Chains

```
7b6.b12
DILLTQSPAILSVSPGERVSFSCRASQSIGTSIHWYQQRTNGSPRLLIKYASESISGIPS
5c9.a2
DIVMTQSHKFMSTSVGDRVSITCKASQDVGTAVAWYQQKPGQSPKLLIYWASTRHTGVPD
5a8.b11    ENVLTQSPAIMSASLGEKVTMSCRASSSVN-
YMYWYQQKSDASPKLWIYYTSNLAPGVPA
4b1.h9
DIQMTQSPASLSASVGETVTITCRASENIYSYLAWYQQKQGKSPQLLVYNAKTLAEGVPS
4a8.e11
DIKMTQSPSSMYASLGERVTFTCKASQDINSFLSWFQQKPGKSPKTLIYRANRLVDGVPS
3f2.e10
DIVMTQSQKFMSTSVGDRVSVTCKASQNVGTNVAWYQQKPGQSPKALIYSASYRYSGVPD

RFSGSGSGTDFTLSINSVESEDIADYYCQQSNSWPFTFGSGTKLEIK
RFTGSGSGTDFTLTISNVQSEDLADYFCQQYSSYPLTFGAGTKLELK
RFSGSGSGNSYSLTISSMEGEDAATYYCQQFTSSPSTFGAGTKLELK
RFSGSGSGTQFSLKINSLQPEDFGSYYCQHHYGTPYTFGGGTNLEIK
RFSGSGSGQDYSLTITSLEFEDMGIYYCLQYDEFPYTFGGGTKLEIK
RFTGSGSGTDFTLTISNVQSEDLAEYFCQQYNSYPLTFGAGTKLEL-
```

Figure 7 mAb 5a8.b11 Heavy Chain

```
<-------------FR1-------><-CDR1-><-------FR2--------><-CDR2-><-------------------FR3-------
EVQLQESGPELVKPGASVKIPCKASGYTFTDYNMDWVKQSHGKSLEWIGDINPNNGGTIYNQKFKGKATLTVDKSSTAYMELRSLTSE
-------><---CDR3--><----FR4--->
DTAVYYCARKGERGFDYWGQGTTLTVSS
``` mAb 5a8.b11 Light-Kappa

```
<-----------FR1----------><CR1><-------FR2-------><-------------FR3----------><-2-><-
ENVLTQSPAIMSASLGEKVTMSCRASSSVNYMYWYQQKSDASPKLWIYYTSNLAPGVPARFSGSGSGNSYSLTISSMEGEDAATYCQQ
-CDR3-><--FR4--->
FTSSPSTFGAGTKLELK
```

Figure 9 mAb 4a8.E11 Heavy Chain

```
<-------FR1-------><-CDR1-><-------FR2-------><-CDR2-><-------------FR3-------------
EVQLQESGGGLVKPGGSLKLSCAASGFTFSDYGMHWVRQAPEKGLEWVAYISSGSSTVYCADTVKGRFTISRDNAKNTLFLQMTSLRSE
------><-CDR3--><---FR4--->
DTAMYYCARRWGYFDYWGQGTTLTVSS
``` mAb 4a8.E11 Light-Kappa Chain

```
<-------FR1-------><-CDR1><------FR2-------><2><-------------FR3-------------------><
DIKMTQSPSSMYASLGERVTFTCKASQDINSFLSWFQQKPGKSPKTLIYRANRLVDGVPSRFSGSGSGQDYSLTITSLEFEDMGIYYCL
--CDR3-><---FR4--->
QYDEFPYTFGGGTKLEIK
```

Figure 10 mAb 4b1.h9 Heavy Chain

<------------FR1-------><--CDR1--><------FR2-------><--CDR2--><--------------FR3------
EVQLQESGPVLVKPGASVKMSCKASGYTFTDYYMNWVKQSHGKSLEWIGVINPYNGGTSYNQKFKGKATLTVDKSSTAYMELNSLTSE
-----><---CDR3---><----FR4--->
DSAVYYCARRRGYAMDYWGQGTSVTVSS mAb 4b1.h9 Light-Kappa Chain <------------FR1-------><CDR1><------FR2-------><2><-------------FR3-------------><
DIQMTQSPASLSASVGETVTITCRASENIYSYLAWYQQKQGKSPQLLVYNAKTLAEGVPSRFSGSGSGTQFSLKINSLQPEDFGSYYCQ
--CDR3--><----FR4--->
HHYGTPYTFGGGTNLEIK

Figure 11 mAb 3f2.e10 Heavy Chain

<-------FR1------><--CDR1--><-------FR2-------><--CDR2--><-----------FR3---------
EVQLQESGGGLVQPKGSLKLSCAASGFSFNTYAMNWVRQAPGKGLEWVARIRSKSNNYATYYADSVKDRFTISRDDSESMLYLQMNNLK
------><--CDR3--><---FR4--->
TEDTAMYYCVRLGAMDYWGQGTSVTVSS mAb 3f2.e10 Light-Kappa Chain <-------FR1------><CDR1><----FR2-----><2><------------FR3-----------><
DIVMTQSQKFMSTSVGDRVSVTCKASQNVGTNVAWYQQKPGQSPKALIYSASYRYSGVPDRFTGSGSGTDFTLTISNVQSEDLAEYFCQ
--CDR3--><---FR4-->
QYNSYPLTFGAGTKLELK

Figure 12 mAb 5C9.A2 Heavy Chain

```
<--------FR1------><-CDR1-><------FR2------><-CDR2-><-------------FR3-------
EVQLQESGPVLVKPGASVKMSCKASGYTFTDYYMNWVKQSHGKSLEWIGVINPYNGGTSYNQKFKGKATLTVDKSSTAYMELNSLTSE
------><----CDR3--><----FR4--->
DSAVYYCASLRRRTDYFDYWGQGTTLTVSS
``` mAb 5C9.A2 Light-Kappa Chain

```
<-------FR1-------><CDR1><------FR2-------><2><-------------FR3---------><
DIVMTQSHKFMSTSVGDRVSITCKASQDVGTAVAWYQQKPGQSPKLLIYWASTRHTGVPDRFTGSGSGTDFTLTISNVQSEDLADYFCQ
-CDR3--><----FR4--->
QYSSYPLTFGAGTKLELK
```

Figure 13 mAb 7b6.b12 Heavy Chain

```
<-------------FR1------><-CDR1-><------FR2--------><-CDR2-><-----------FR3-----
EVQLQESGAELVKPGASVKISCKVSGYTFTDHTIHWMKQRPEQGLEWIGYIYPRDGSTKYNEKFKGKATLTADKSSTAYMQLNSLTSE
------><-----CDR3--><----FR4--->
DSAVYFCARPYDYAWFAYWGQGTLVTVSA
``` mAb 7b6.b12 Light-Kappa Chain

```
<--------------FR1-----------><CDR1><------FR2------><2><-------------FR3----------------><
DILLTQSPAILSVSPGERVSFSCRASQSIGTSIHWYQQRTNGSPRLLIKYASESISGIPSRFSGSGSGTDFTLSINSVESEDIADYYCQ
--CDR3---><----FR4--->
QSNSWPFTFGSGTKLEIK
```

Figure 14

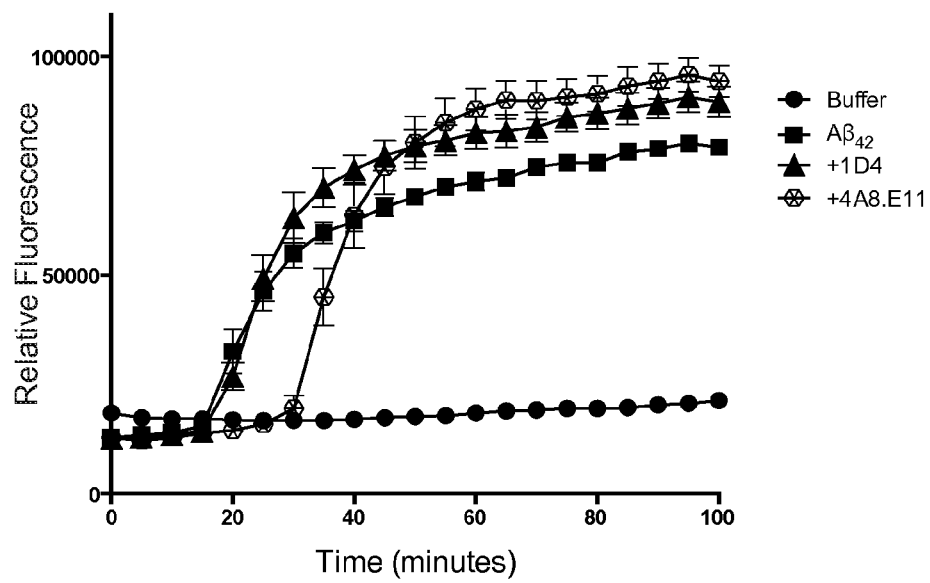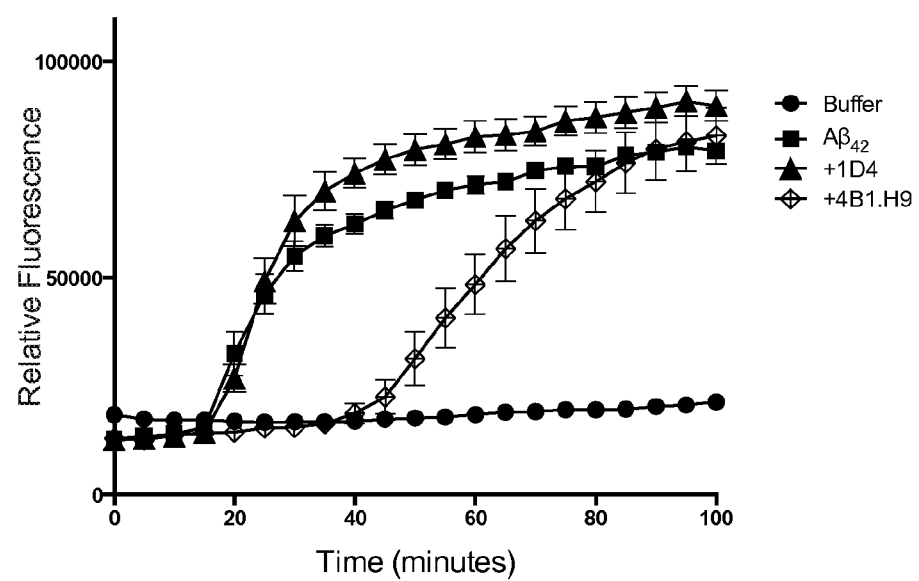
Figure 15 A

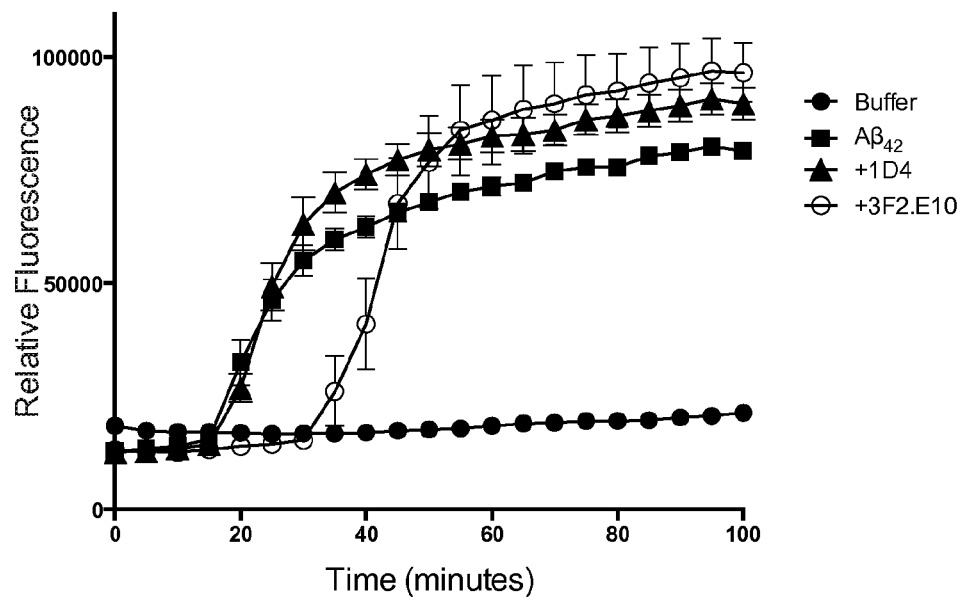
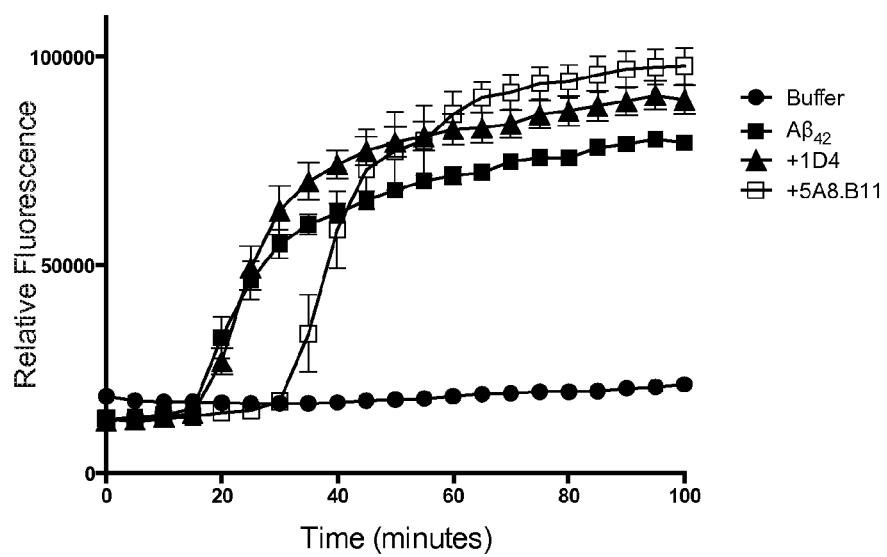
Figure 15 B

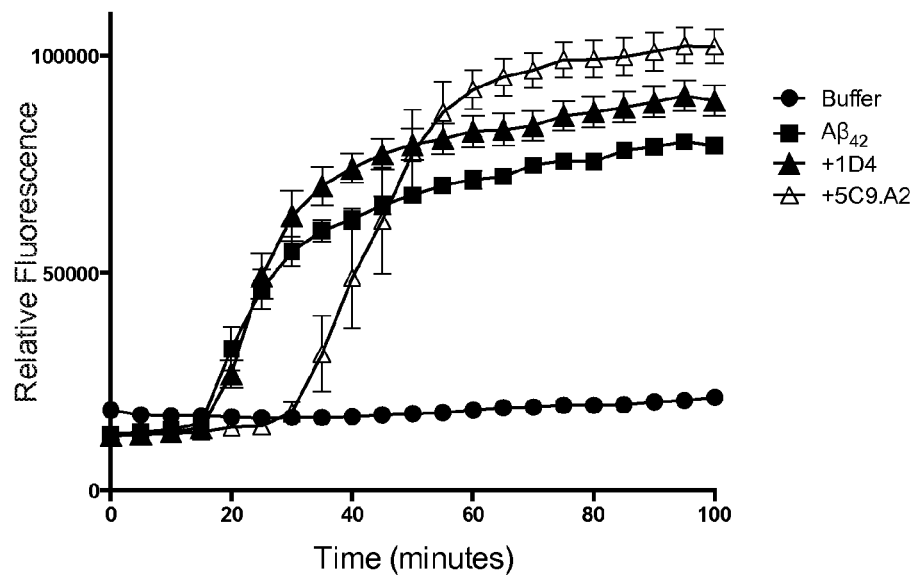
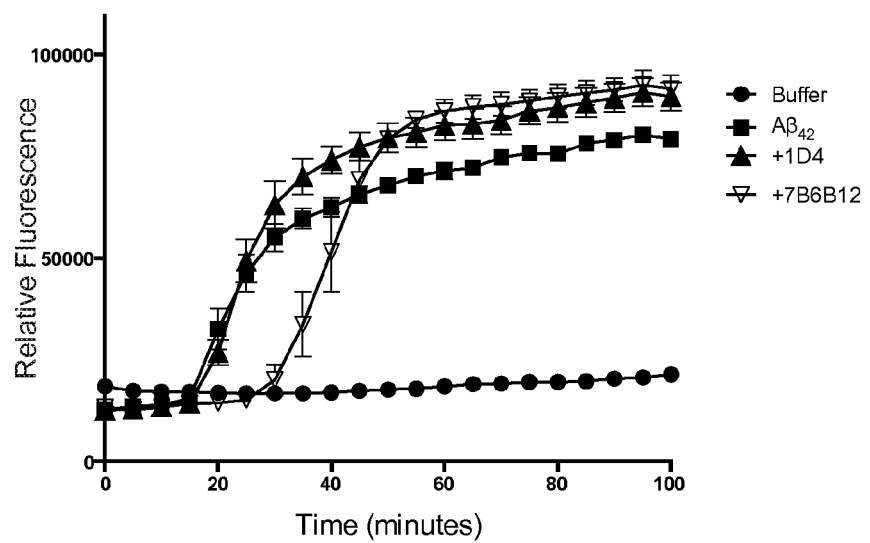
Figure 15 C

B.

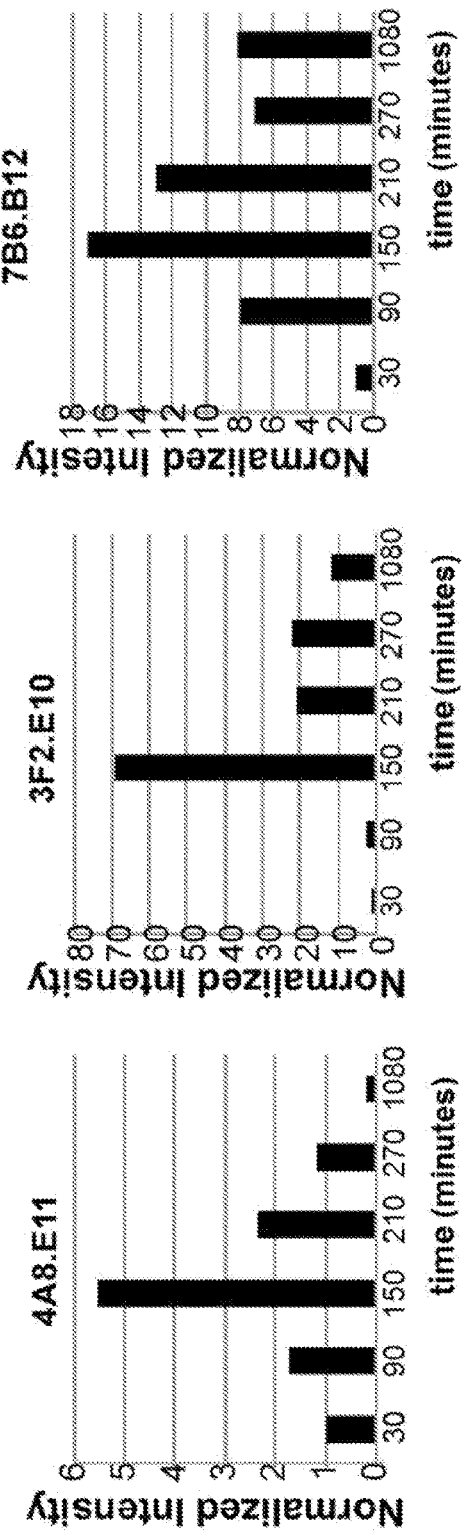
Figure 18 C, D, E

```
                        SEQUENCE LISTING

<160> NUMBER OF SEQ ID NOS: 102

<210> SEQ ID NO 1
<211> LENGTH: 461
<212> TYPE: PRT
<213> ORGANISM: Homo sapiens

<400> SEQUENCE: 1

Met Pro Pro Ser Gly Pro Arg Gly Thr Leu Leu Leu Pro Leu Leu
1               5                   10                  15

Leu Leu Leu Leu Leu Arg Ala Val Leu Ala Val Pro Leu Glu Arg Gly
                20                  25                  30

Ala Pro Asn Lys Glu Glu Thr Pro Ala Thr Glu Ser Pro Asp Thr Gly
            35                  40                  45

Leu Tyr Tyr His Arg Tyr Leu Gln Glu Val Ile Asp Val Leu Glu Thr
    50                  55                  60

Asp Gly His Phe Arg Glu Lys Leu Gln Ala Ala Asn Ala Glu Asp Ile
65                  70                  75                  80

Lys Ser Gly Lys Leu Ser Arg Glu Leu Asp Phe Val Ser His His Val
                85                  90                  95

Arg Thr Lys Leu Asp Glu Leu Lys Arg Gln Glu Val Ser Arg Leu Arg
            100                 105                 110

Met Leu Leu Lys Ala Lys Met Asp Ala Glu Gln Asp Pro Asn Val Gln
        115                 120                 125

Val Asp His Leu Asn Leu Leu Lys Gln Phe Glu His Leu Asp Pro Gln
130                 135                 140

Asn Gln His Thr Phe Glu Ala Arg Asp Leu Glu Leu Leu Ile Gln Thr
145                 150                 155                 160

Ala Thr Arg Asp Leu Ala Gln Tyr Asp Ala Ala His His Glu Glu Phe
                165                 170                 175

Lys Arg Tyr Glu Met Leu Lys Glu His Glu Arg Arg Tyr Leu Glu
            180                 185                 190

Ser Leu Gly Glu Glu Gln Arg Lys Glu Ala Glu Arg Lys Leu Glu Glu
        195                 200                 205

Gln Gln Arg Arg His Arg Glu His Pro Lys Val Asn Val Pro Gly Ser
    210                 215                 220

Gln Ala Gln Leu Lys Glu Val Trp Glu Glu Leu Asp Gly Leu Asp Pro
225                 230                 235                 240

Asn Arg Phe Asn Pro Lys Thr Phe Phe Ile Leu His Asp Ile Asn Ser
                245                 250                 255
```

-continued

Asp Gly Val Leu Asp Glu Gln Glu Leu Glu Ala Leu Phe Thr Lys Glu
            260                 265                 270

Leu Glu Lys Val Tyr Asp Pro Lys Asn Glu Glu Asp Met Arg Glu
        275                 280                 285

Met Glu Glu Glu Arg Leu Arg Met Arg Glu His Val Met Lys Asn Val
    290                 295                 300

Asp Thr Asn Gln Asp Arg Leu Val Thr Leu Glu Glu Phe Leu Ala Ser
305                 310                 315                 320

Thr Gln Arg Lys Glu Phe Gly Asp Thr Gly Glu Gly Trp Glu Thr Val
                325                 330                 335

Glu Met His Pro Ala Tyr Thr Glu Glu Glu Leu Arg Arg Phe Glu Glu
                340                 345                 350

Glu Leu Ala Ala Arg Glu Ala Glu Leu Asn Ala Lys Ala Gln Arg Leu
            355                 360                 365

Ser Gln Glu Thr Glu Ala Leu Gly Arg Ser Gln Gly Arg Leu Glu Ala
    370                 375                 380

Gln Lys Arg Glu Leu Gln Gln Ala Val Leu His Met Glu Gln Arg Lys
385                 390                 395                 400

Gln Gln Gln Gln Gln Gln Gly His Lys Ala Pro Ala His Pro
                405                 410                 415

Glu Gly Gln Leu Lys Phe His Pro Asp Thr Asp Val Pro Val Pro
                420                 425                 430

Ala Pro Ala Gly Asp Gln Lys Glu Val Asp Thr Ser Glu Lys Lys Leu
            435                 440                 445

Leu Glu Arg Leu Pro Glu Val Glu Val Pro Gln His Leu
    450                 455                 460

<210> SEQ ID NO 2
<211> LENGTH: 474
<212> TYPE: PRT
<213> ORGANISM: Bos taurus

<400> SEQUENCE: 2

Met Pro Pro Ser Gly Pro Arg Ala Ala Leu Phe Leu Leu Pro Ser Leu
1               5                   10                  15

Leu Leu Leu Arg Ala Val Leu Ala Val Pro Leu Glu Arg Gly Ala Pro
            20                  25                  30

Lys Glu Glu Asn Pro Ala Thr Glu Ser Pro Asp Thr Gly Leu Tyr Tyr
        35                  40                  45

His Arg Tyr Leu Gln Glu Val Ile Asn Val Leu Glu Thr Asp Gly His
    50                  55                  60

Phe Arg Glu Lys Leu Gln Ala Ala Asn Ala Glu Asp Ile Lys Ser Gly
65                  70                  75                  80

Lys Leu Ser Arg Glu Leu Asp Phe Val Ser His His Val Arg Thr Lys
                85                  90                  95

Leu Asp Glu Leu Lys Arg Gln Glu Val Ser Arg Leu Arg Met Leu Leu
            100                 105                 110

Lys Ala Lys Met Asp Ala Gln Gln Glu Pro Asn Ile Gln Leu Asp His
        115                 120                 125

Leu Asn Leu Leu Lys Gln Phe Glu His Leu Asp Pro Gln Asn Gln His
    130                 135                 140

Thr Phe Glu Ala Arg Asp Leu Glu Leu Leu Ile Gln Thr Ala Thr Arg
145                 150                 155                 160

Asp Leu Ala Gln Tyr Asp Ala Ala His His Glu Glu Phe Lys Arg Tyr

```
            165                 170                 175
Glu Met Leu Lys Glu His Glu Arg Arg Tyr Leu Glu Ser Leu Gly
            180                 185                 190

Glu Glu Gln Arg Lys Glu Ala Glu Arg Lys Leu Glu Glu Gln Arg
            195                 200                 205

Arg His Arg Glu His Pro Lys Val Asn Val Pro Gly Ser Gln Ala Gln
210                 215                 220

Leu Lys Glu Val Trp Glu Leu Asp Gly Leu Asp Pro Asn Arg Phe
225                 230                 235                 240

Asn Pro Lys Thr Phe Phe Ile Leu His Asp Ile Asn Ser Asp Gly Val
            245                 250                 255

Leu Asp Glu Gln Glu Leu Glu Ala Leu Phe Thr Lys Glu Leu Glu Lys
            260                 265                 270

Val Tyr Asp Pro Lys Asn Glu Asp Asp Met Arg Glu Met Glu Glu
            275                 280                 285

Glu Arg Leu Arg Met Arg Glu His Val Met Lys Asn Val Asp Thr Asn
            290                 295                 300

Gln Asp Arg Leu Val Thr Leu Glu Glu Phe Leu Ala Ser Thr Gln Arg
305                 310                 315                 320

Lys Glu Phe Gly Asp Thr Gly Glu Gly Trp Glu Gly Lys Ala Gly
            325                 330                 335

Val Pro Leu Pro Met Ala Pro Val Leu Thr Leu Gln Thr Val Glu Met
            340                 345                 350

His Pro Ala Tyr Thr Glu Glu Leu Arg Arg Phe Glu Glu Glu Leu
            355                 360                 365

Ala Ala Arg Glu Ala Glu Leu Asn Ala Lys Ala Gln Arg Leu Ser Gln
            370                 375                 380

Glu Thr Glu Ala Leu Gly Arg Ser Gln Gly Arg Leu Glu Ala Gln Lys
385                 390                 395                 400

Arg Glu Leu Gln Gln Ala Val Leu Gln Met Glu Gln Arg Lys Gln Gln
                    405                 410                 415

Gln Gln Ser His Asn Asn Pro Ala Pro Gly Pro Glu Gly Gln Leu Lys
            420                 425                 430

Phe His Pro Asp Thr Asp Val Pro Val Pro Ala Pro Ala Gly Asp
            435                 440                 445

Gln Lys Asp Val Asp Ala Ser Glu Lys Lys Val Pro Glu Gln Thr Pro
            450                 455                 460

Glu Pro Pro Gln Leu Asp Ser Gln His Leu
465                 470

<210> SEQ ID NO 3
<211> LENGTH: 457
<212> TYPE: PRT
<213> ORGANISM: Sus scrofa

<400> SEQUENCE: 3

Met Pro Pro Tyr Gly Thr Leu Thr Ala Leu Leu Leu Pro Leu
1               5                   10                  15

Leu Leu Leu His Ala Val Leu Ala Val Pro Leu Asp Arg Gly Ala Ser
            20                  25                  30

Lys Glu Glu Asn Pro Ala Thr Glu Ser Pro Asp Thr Gly Leu Tyr Tyr
            35                  40                  45

His Arg Tyr Leu Gln Glu Val Ile Asn Val Leu Glu Thr Asp Gly His
        50                  55                  60
```

Phe Arg Glu Lys Leu Gln Ala Ala Asn Ala Glu Asp Ile Lys Ser Gly
65                  70                  75                  80

Lys Leu Ser Arg Glu Leu Asp Phe Val Ser His His Val Arg Thr Lys
                85                  90                  95

Leu Asp Glu Leu Lys Arg Gln Glu Val Ser Arg Leu Arg Met Leu Leu
            100                 105                 110

Lys Ala Lys Met Asp Ala Glu Gln Glu Pro Asn Val Gln Leu Asp His
        115                 120                 125

Leu Asn Leu Leu Lys Gln Phe Glu His Leu Asp Pro Gln Asn Gln His
    130                 135                 140

Thr Phe Glu Ala Arg Asp Leu Glu Leu Leu Ile Gln Thr Ala Thr Arg
145                 150                 155                 160

Asp Leu Ala Gln Tyr Asp Ala Ala His His Glu Glu Phe Lys Arg Tyr
                165                 170                 175

Glu Met Leu Lys Glu His Glu Arg Arg Arg Tyr Leu Glu Ser Leu Gly
            180                 185                 190

Glu Glu Gln Arg Lys Glu Ala Gly Lys Lys Leu Glu Glu Gln Gln Arg
        195                 200                 205

Arg His Arg Glu His Pro Lys Val Asn Val Pro Gly Ser Gln Ala Gln
    210                 215                 220

Leu Lys Glu Val Trp Glu Glu Leu Asp Gly Leu Asp Pro Asn Arg Phe
225                 230                 235                 240

Asn Pro Lys Thr Phe Phe Ile Leu His Asp Ile Asn Ser Asp Gly Val
                245                 250                 255

Leu Asp Glu Gln Glu Leu Glu Ala Leu Phe Thr Lys Glu Leu Glu Lys
            260                 265                 270

Val Tyr Asp Pro Lys Asn Glu Glu Asp Asp Met Arg Glu Met Glu Glu
        275                 280                 285

Glu Arg Leu Arg Met Arg Glu His Val Met Lys Asn Val Asp Thr Asn
    290                 295                 300

Gln Asp Arg Leu Val Thr Leu Asp Glu Phe Leu Ala Ser Thr Gln Arg
305                 310                 315                 320

Lys Glu Phe Gly Asp Thr Gly Glu Gly Trp Glu Thr Val Glu Met His
                325                 330                 335

Pro Ala Tyr Thr Glu Asp Glu Leu Arg Arg Phe Glu Glu Glu Leu Ala
            340                 345                 350

Ala Arg Glu Ala Glu Leu Asn Ala Lys Ala Gln Arg Leu Ser Gln Glu
        355                 360                 365

Thr Glu Ala Leu Gly Arg Ser Gln Gly Arg Leu Glu Ala Gln Lys Arg
    370                 375                 380

Glu Leu Gln Gln Ala Val Leu Gln Met Glu Gln Arg Lys Gln Gln Gln
385                 390                 395                 400

Gln Gly His Lys Asp Pro Ala Thr Gly Pro Glu Gly Gln Leu Lys Phe
                405                 410                 415

His Pro Asp Thr Asp Ala Pro Val Pro Ala Pro Ala Gly Asp Gln
            420                 425                 430

Lys Asp Val Asp Ala Ser Glu Lys Lys Val Pro Glu Gln Thr Pro Glu
        435                 440                 445

Leu Pro Gln Leu Asp Ser Gln His Leu
    450                 455

<210> SEQ ID NO 4
<211> LENGTH: 457
<212> TYPE: PRT

<213> ORGANISM: Canis familiaris

<400> SEQUENCE: 4

Met Pro Ser Ser Gly Pro Arg Ala Ala Leu Leu Leu Pro Pro Leu
1               5                   10                  15

Leu Leu Leu Arg Ala Val Leu Ala Val Pro Leu Glu Arg Gly Ala Pro
            20                  25                  30

Lys Gln Glu Ser Pro Ala Thr Glu Ser Pro Asp Thr Gly Leu Tyr Tyr
            35                  40                  45

His Arg Tyr Leu Gln Glu Val Ile Asn Val Leu Glu Thr Asp Gly His
    50                  55                  60

Phe Arg Glu Lys Leu Gln Ala Ala Asn Ala Glu Asp Ile Lys Ser Gly
65                  70                  75                  80

Lys Leu Ser Arg Glu Leu Asp Phe Val Ser His His Val Arg Thr Lys
            85                  90                  95

Leu Asp Glu Leu Lys Arg Gln Glu Val Ser Arg Leu Arg Met Leu Leu
            100                 105                 110

Lys Ala Lys Met Asp Ala Glu Gln Glu Pro Asn Val Gln Leu Asp His
            115                 120                 125

Leu Ser Leu Leu Lys Gln Phe Glu His Leu Asp Pro Gln Asn Gln His
    130                 135                 140

Thr Phe Glu Ala Arg Asp Leu Glu Leu Leu Ile Gln Thr Ala Thr Arg
145                 150                 155                 160

Asp Leu Ala Gln Tyr Asp Ala Ala His His Glu Glu Phe Lys Arg Tyr
            165                 170                 175

Glu Met Leu Lys Glu His Glu Arg Arg Tyr Leu Glu Ser Leu Gly
            180                 185                 190

Glu Glu Gln Arg Lys Glu Ala Glu Arg Lys Leu Glu Glu Gln Gln Arg
            195                 200                 205

Arg His Arg Glu His Pro Lys Val Asn Val Pro Gly Ser Gln Ala Gln
            210                 215                 220

Leu Lys Glu Val Trp Glu Glu Leu Asp Gly Leu Asp Pro Asn Arg Phe
225                 230                 235                 240

Asn Pro Lys Thr Phe Phe Ile Leu His Asp Ile Asn Ser Asp Gly Val
            245                 250                 255

Leu Asp Glu Gln Glu Leu Glu Ala Leu Phe Thr Lys Glu Leu Glu Lys
            260                 265                 270

Val Tyr Asp Pro Lys Asn Glu Glu Asp Asp Met Arg Glu Met Glu Glu
            275                 280                 285

Glu Arg Leu Arg Met Arg Glu His Val Met Lys Asn Val Asp Thr Asn
            290                 295                 300

Gln Asp Arg Leu Val Thr Leu Glu Glu Phe Leu Ala Ser Thr Gln Arg
305                 310                 315                 320

Lys Glu Phe Gly Asp Thr Gly Glu Gly Trp Glu Thr Val Glu Met His
            325                 330                 335

Pro Ala Tyr Thr Glu Glu Glu Leu Arg Arg Phe Glu Glu Glu Leu Ala
            340                 345                 350

Ala Arg Glu Ala Glu Leu Asn Ala Lys Ala Gln Arg Leu Ser Gln Glu
            355                 360                 365

Thr Glu Ala Leu Gly Arg Ser Gln Gly Arg Leu Glu Ala Gln Lys Arg
            370                 375                 380

Glu Leu Gln Gln Ala Val Leu Gln Met Glu Gln Arg Lys Gln Gln Gln
385                 390                 395                 400

-continued

Gln Asn Gln Asn Ser Pro Ala Pro Gly Pro Glu Gly Gln Leu Gln Phe
            405                 410                 415

His Pro Asp Thr Asp Asp Ala Pro Val Pro Ala Pro Ala Gly Asp Gln
        420                 425                 430

Lys Asp Ala Asp Thr Ser Glu Lys Lys Ala Pro Asp Gln Pro Pro Glu
    435                 440                 445

Leu Pro Gln Leu Asp Thr Gln His Leu
    450                 455

<210> SEQ ID NO 5
<211> LENGTH: 31
<212> TYPE: DNA
<213> ORGANISM: Artificial
<220> FEATURE:
<223> OTHER INFORMATION: synthetic

<400> SEQUENCE: 5
gggaattcga ggtgcagctg caggagtctg g                              31

<210> SEQ ID NO 6
<211> LENGTH: 24
<212> TYPE: DNA
<213> ORGANISM: Artificial
<220> FEATURE:
<223> OTHER INFORMATION: synthetic

<400> SEQUENCE: 6 aggggggctct cgcaggagac gagg                                     24

<210> SEQ ID NO 7
<211> LENGTH: 23
<212> TYPE: DNA
<213> ORGANISM: Artificial
<220> FEATURE:
<223> OTHER INFORMATION: synthetic

<400> SEQUENCE: 7
ggaaggtgtg cacaccgctg gac                                       23

<210> SEQ ID NO 8
<211> LENGTH: 23
<212> TYPE: DNA
<213> ORGANISM: Artificial
<220> FEATURE:
<223> OTHER INFORMATION: synthetic

<400> SEQUENCE: 8
ggaaggtgtg cacaccactg gac                                       23

<210> SEQ ID NO 9
<211> LENGTH: 23
<212> TYPE: DNA
<213> ORGANISM: Artificial
<220> FEATURE:
<223> OTHER INFORMATION: synthetic

<400> SEQUENCE: 9
ggaaggtgtg cacactgctg gac                                       23

<210> SEQ ID NO 10
<211> LENGTH: 23
<212> TYPE: DNA
<213> ORGANISM: Artificial
<220> FEATURE:
<223> OTHER INFORMATION: synthetic

```
<400> SEQUENCE: 10
agactgtgcg cacaccgctg gac                                          23

<210> SEQ ID NO 11
<211> LENGTH: 23
<212> TYPE: DNA
<213> ORGANISM: Artificial
<220> FEATURE:
<223> OTHER INFORMATION: synthetic

<400> SEQUENCE: 11
gaaagttcac ggtggttata tcc                                          23

<210> SEQ ID NO 12
<211> LENGTH: 31
<212> TYPE: DNA
<213> ORGANISM: Artificial
<220> FEATURE:
<223> OTHER INFORMATION: synthetic

<400> SEQUENCE: 12
gggaattcga ggtgcagctg caggagtctg g                                 31

<210> SEQ ID NO 13
<211> LENGTH: 24
<212> TYPE: DNA
<213> ORGANISM: Artificial
<220> FEATURE:
<223> OTHER INFORMATION: synthetic

<400> SEQUENCE: 13 aggggggaaga catttgggaa ggac                                        24

<210> SEQ ID NO 14
<211> LENGTH: 22
<212> TYPE: DNA
<213> ORGANISM: Artificial
<220> FEATURE:
<223> OTHER INFORMATION: synthetic

<400> SEQUENCE: 14
gctcagggaa atagcccttg ac                                           22

<210> SEQ ID NO 15
<211> LENGTH: 22
<212> TYPE: DNA
<213> ORGANISM: Artificial
<220> FEATURE:
<223> OTHER INFORMATION: synthetic

<400> SEQUENCE: 15
gctcagggaa ataccccttg ac                                           22

<210> SEQ ID NO 16
<211> LENGTH: 22
<212> TYPE: DNA
<213> ORGANISM: Artificial
<220> FEATURE:
<223> OTHER INFORMATION: synthetic

<400> SEQUENCE: 16
actcagggaa gtagcccttg ac                                           22

<210> SEQ ID NO 17
```

<211> LENGTH: 22
<212> TYPE: DNA
<213> ORGANISM: Artificial
<220> FEATURE:
<223> OTHER INFORMATION: synthetic

<400> SEQUENCE: 17
gctcagggaa gtagcctttg ac                                          22

<210> SEQ ID NO 18
<211> LENGTH: 25
<212> TYPE: DNA
<213> ORGANISM: Artificial
<220> FEATURE:
<223> OTHER INFORMATION: synthetic

<400> SEQUENCE: 18
tgccgaaagg gaagtaatcg tgaat                                       25

<210> SEQ ID NO 19
<211> LENGTH: 21
<212> TYPE: DNA
<213> ORGANISM: Artificial
<220> FEATURE:
<223> OTHER INFORMATION: synthetic

<400> SEQUENCE: 19
tgctgctgct ctgggttcca g                                           21

<210> SEQ ID NO 20
<211> LENGTH: 21
<212> TYPE: DNA
<213> ORGANISM: Artificial
<220> FEATURE:
<223> OTHER INFORMATION: synthetic

<400> SEQUENCE: 20
attwtcagct tcctgctaat c                                           21

<210> SEQ ID NO 21
<211> LENGTH: 21
<212> TYPE: DNA
<213> ORGANISM: Artificial
<220> FEATURE:
<223> OTHER INFORMATION: synthetic

<400> SEQUENCE: 21
ttttgctttt ctggattyca g                                           21

<210> SEQ ID NO 22
<211> LENGTH: 21
<212> TYPE: DNA
<213> ORGANISM: Artificial
<220> FEATURE:
<223> OTHER INFORMATION: synthetic

<400> SEQUENCE: 22
tcgtgttkct stggttgtct g                                           21

<210> SEQ ID NO 23
<211> LENGTH: 20
<212> TYPE: DNA
<213> ORGANISM: Artificial
<220> FEATURE:
<223> OTHER INFORMATION: synthetic

<400> SEQUENCE: 23

-continued atggaatcac agrcycwggt                                        20

<210> SEQ ID NO 24
<211> LENGTH: 21
<212> TYPE: DNA
<213> ORGANISM: Artificial
<220> FEATURE:
<223> OTHER INFORMATION: synthetic

<400> SEQUENCE: 24
tcttgttgct ctggttycca g                                      21

<210> SEQ ID NO 25
<211> LENGTH: 24
<212> TYPE: DNA
<213> ORGANISM: Artificial
<220> FEATURE:
<223> OTHER INFORMATION: synthetic

<400> SEQUENCE: 25
cagttcctgg ggctcttgtt gttc                                   24

<210> SEQ ID NO 26
<211> LENGTH: 19
<212> TYPE: DNA
<213> ORGANISM: Artificial
<220> FEATURE:
<223> OTHER INFORMATION: synthetic

<400> SEQUENCE: 26
ctcactagct cttctcctc                                         19

<210> SEQ ID NO 27
<211> LENGTH: 24
<212> TYPE: DNA
<213> ORGANISM: Artificial
<220> FEATURE:
<223> OTHER INFORMATION: synthetic

<400> SEQUENCE: 27
gatggtggga agatggatac agtt                                   24

<210> SEQ ID NO 28
<211> LENGTH: 24
<212> TYPE: DNA
<213> ORGANISM: Artificial
<220> FEATURE:
<223> OTHER INFORMATION: synthetic

<400> SEQUENCE: 28
gayattgtgm tsacmcarwc tmca                                   24

<210> SEQ ID NO 29
<211> LENGTH: 30
<212> TYPE: DNA
<213> ORGANISM: Artificial
<220> FEATURE:
<223> OTHER INFORMATION: synthetic

<400> SEQUENCE: 29
gccaccgtac gtttgatttc cagcttggtg                             30

<210> SEQ ID NO 30
<211> LENGTH: 30
<212> TYPE: DNA

```
<213> ORGANISM: Artificial
<220> FEATURE:
<223> OTHER INFORMATION: synthetic

<400> SEQUENCE: 30
gccaccgtac gttttatttc cagcttggtc                                    30

<210> SEQ ID NO 31
<211> LENGTH: 30
<212> TYPE: DNA
<213> ORGANISM: Artificial
<220> FEATURE:
<223> OTHER INFORMATION: synthetic

<400> SEQUENCE: 31
gccaccgtac gttttatttc caactttgtc                                    30

<210> SEQ ID NO 32
<211> LENGTH: 30
<212> TYPE: DNA
<213> ORGANISM: Artificial
<220> FEATURE:
<223> OTHER INFORMATION: synthetic

<400> SEQUENCE: 32
gccaccgtac gtttcagctc cagcttggtc                                    30

<210> SEQ ID NO 33
<211> LENGTH: 18
<212> TYPE: DNA
<213> ORGANISM: Artificial
<220> FEATURE:
<223> OTHER INFORMATION: synthetic

<400> SEQUENCE: 33
caggctgttg tgactcag                                                 18

<210> SEQ ID NO 34
<211> LENGTH: 18
<212> TYPE: DNA
<213> ORGANISM: Artificial
<220> FEATURE:
<223> OTHER INFORMATION: synthetic

<400> SEQUENCE: 34
caacttgtgc tcactcag                                                 18

<210> SEQ ID NO 35
<211> LENGTH: 24
<212> TYPE: DNA
<213> ORGANISM: Artificial
<220> FEATURE:
<223> OTHER INFORMATION: synthetic

<400> SEQUENCE: 35
gtaccatytg ccttccagkc cact                                          24

<210> SEQ ID NO 36
<211> LENGTH: 18
<212> TYPE: DNA
<213> ORGANISM: Artificial
<220> FEATURE:
<223> OTHER INFORMATION: synthetic

<400> SEQUENCE: 36
caggctgttg tgactcag                                                 18
```

<210> SEQ ID NO 37
<211> LENGTH: 18
<212> TYPE: DNA
<213> ORGANISM: Artificial
<220> FEATURE:
<223> OTHER INFORMATION: synthetic

<400> SEQUENCE: 37
caacttgtgc tcactcag                                                 18

<210> SEQ ID NO 38
<211> LENGTH: 23
<212> TYPE: DNA
<213> ORGANISM: Artificial
<220> FEATURE:
<223> OTHER INFORMATION: synthetic

<400> SEQUENCE: 38
ctcytcagrg gaaggtggra aca                                           23

<210> SEQ ID NO 39
<211> LENGTH: 352
<212> TYPE: DNA
<213> ORGANISM: Mus musculus

<400> SEQUENCE: 39
gaggtgcagc tgcaggagtc tggacctgag ctggtgaagc ctggggcttc agtgaagata    60
ccctgcaagg cttctggata cacattcact gactacaaca tggactgggt gaagcagagc   120
catggaaaga gccttgagtg gattggagat attaatccta caatggtgg tactatctac    180 aaccagaagt tcaagggcaa ggccacattg actgtagaca gtcctccag cacagcctac    240 atggagctcc gcagcctgac atctgaggac actgcagtct attactgtgc aagaaagggg   300
gagaggggct ttgactactg gggccaaggc accactctca cagtctcctc ag           352

<210> SEQ ID NO 40
<211> LENGTH: 117
<212> TYPE: PRT
<213> ORGANISM: Mus musculus

<400> SEQUENCE: 40

Glu Val Gln Leu Gln Glu Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Lys Gly Glu Arg Gly Phe Asp Tyr Trp Gly Gln Gly Thr Thr
            100                 105                 110

Leu Thr Val Ser Ser
        115

<210> SEQ ID NO 41

<211> LENGTH: 319
<212> TYPE: DNA
<213> ORGANISM: Mus musculus

<400> SEQUENCE: 41

```
gaaaatgtgc tcacccagtc tccagcaatc atgtctgcat ctctagggga gaaggtcacc    60
atgagctgca gggccagctc aagtgtaaat tacatgtact ggtaccagca gaagtcagat   120
gcctccccca aactatggat ttattacaca tccaacctgg ctcctggagt cccagctcgc   180
ttcagtggca gtgggtctgg gaactcttat tctctcacaa tcagcagcat ggagggtgaa   240
gatgctgcca cttattactg ccagcagttt actagttccc catccacgtt cggtgctggg   300
accaagctgg agctgaaac                                                319
```

<210> SEQ ID NO 42
<211> LENGTH: 106
<212> TYPE: PRT
<213> ORGANISM: Mus musculus

<400> SEQUENCE: 42

```
Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Ser Thr
                85                  90                  95

Phe Gly Ala Gly Thr Lys Leu Glu Leu Lys
            100                 105
```

<210> SEQ ID NO 43
<211> LENGTH: 8
<212> TYPE: PRT
<213> ORGANISM: Mus musculus

<400> SEQUENCE: 43

```
Gly Tyr Thr Phe Thr Asp Tyr Asn
1               5
```

<210> SEQ ID NO 44
<211> LENGTH: 8
<212> TYPE: PRT
<213> ORGANISM: Mus musculus

<400> SEQUENCE: 44

```
Ile Asn Pro Asn Asn Gly Gly Thr
1               5
```

<210> SEQ ID NO 45
<211> LENGTH: 10
<212> TYPE: PRT
<213> ORGANISM: Mus musculus

<400> SEQUENCE: 45

```
Ala Arg Lys Gly Glu Arg Gly Phe Asp Tyr
1               5                   10
```

<210> SEQ ID NO 46
<211> LENGTH: 5
<212> TYPE: PRT
<213> ORGANISM: Mus musculus

<400> SEQUENCE: 46

Ser Ser Val Asn Tyr
1               5

<210> SEQ ID NO 47
<211> LENGTH: 56
<212> TYPE: PRT
<213> ORGANISM: Mus musculus

<400> SEQUENCE: 47

Met Tyr Trp Tyr Gln Gln Lys Ser Asp Ala Ser Pro Lys Leu Trp Ile
1               5                   10                  15

Tyr Tyr Thr Ser Asn Leu Ala Pro Gly Val Pro Ala Arg Phe Ser Gly
            20                  25                  30

Ser Gly Ser Gly Asn Ser Tyr Ser Leu Thr Ile Ser Ser Met Glu Gly
        35                  40                  45

Glu Asp Ala Ala Thr Tyr Tyr Cys
    50                  55

<210> SEQ ID NO 48
<211> LENGTH: 8
<212> TYPE: PRT
<213> ORGANISM: Mus musculus

<400> SEQUENCE: 48

Gln Phe Thr Ser Ser Pro Ser Thr
1               5

<210> SEQ ID NO 49
<211> LENGTH: 349
<212> TYPE: DNA
<213> ORGANISM: Mus musculus

<400> SEQUENCE: 49
gaggtgcagc tgcaggagtc tgggggaggc ttagtgaagc ctggagggtc cctgaaactc      60
tcctgtgcag cctctggatt cactttcagt gactatggaa tgcactgggt tcgtcaggct     120
ccagagaagg gactggagtg ggttgcatac attagtagtg gcagtagtac cgtctactgt     180
gcagacacag tgaagggccg attcaccatc tccagagaca tgccaagaa cacccctgttc     240 ctgcaaatga ccagtctgag gtctgaggac acggccatgt attactgtgc aaggcgctgg     300
ggctactttg actactgggg ccaaggcacc actctcacag tctcctcag               349

<210> SEQ ID NO 50
<211> LENGTH: 116
<212> TYPE: PRT
<213> ORGANISM: Mus musculus

<400> SEQUENCE: 50

Glu Val Gln Leu Gln Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

```
Ala Tyr Ile Ser Ser Gly Ser Ser Thr Val Tyr Cys Ala Asp Thr Val
        50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Trp Gly Tyr Phe Asp Tyr Trp Gly Gln Gly Thr Thr Leu
            100                 105                 110

Thr Val Ser Ser
        115

<210> SEQ ID NO 51
<211> LENGTH: 322
<212> TYPE: DNA
<213> ORGANISM: Mus musculus

<400> SEQUENCE: 51
gacatcaaga tgacccagtc tccatcttcc atgtatgcat ctctaggaga gagagtcact      60
ttcacttgca aggcgagtca ggacattaat agcttttttaa gctggttcca gcagaaacca     120
gggaaatctc ctaagaccct gatctatcgt gcaaacagat tggtagatgg ggtcccatca     180
aggttcagtg gcagtggatc tgggcaagat tattctctca ccatcaccag cctggagttt     240
gaagatatgg gaatttatta ttgtctacag tatgatgagt ttccgtacac gttcggaggg     300
gggaccaagc tggaaataaa ac                                              322

<210> SEQ ID NO 52
<211> LENGTH: 107
<212> TYPE: PRT
<213> ORGANISM: Mus musculus

<400> SEQUENCE: 52

Asp Ile Lys Met Thr Gln Ser Pro Ser Ser Met Tyr Ala Ser Leu Gly
1               5                   10                  15

Glu Arg Val Thr Phe Thr Cys Lys Ala Ser Gln Asp Ile Asn Ser Phe
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Thr Ser Leu Glu Phe
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 53
<211> LENGTH: 8
<212> TYPE: PRT
<213> ORGANISM: Mus musculus

<400> SEQUENCE: 53

Gly Phe Thr Phe Ser Asp Tyr Gly
1               5

<210> SEQ ID NO 54
<211> LENGTH: 8
```

```
<212> TYPE: PRT
<213> ORGANISM: Mus musculus

<400> SEQUENCE: 54

Ile Ser Ser Gly Ser Ser Thr Val
1               5

<210> SEQ ID NO 55
<211> LENGTH: 9
<212> TYPE: PRT
<213> ORGANISM: Mus musculus

<400> SEQUENCE: 55

Ala Arg Arg Trp Gly Tyr Phe Asp Tyr
1               5

<210> SEQ ID NO 56
<211> LENGTH: 6
<212> TYPE: PRT
<213> ORGANISM: Mus musculus

<400> SEQUENCE: 56

Gln Asp Ile Asn Ser Phe
1               5

<210> SEQ ID NO 57
<211> LENGTH: 56
<212> TYPE: PRT
<213> ORGANISM: Mus musculus

<400> SEQUENCE: 57

Leu Ser Trp Phe Gln Gln Lys Pro Gly Lys Ser Pro Lys Thr Leu Ile
1               5                   10                  15
Tyr Arg Ala Asn Arg Leu Val Asp Gly Val Pro Ser Arg Phe Ser Gly
            20                  25                  30
Ser Gly Ser Gly Gln Asp Tyr Ser Leu Thr Ile Thr Ser Leu Glu Phe
        35                  40                  45
Glu Asp Met Gly Ile Tyr Tyr Cys
    50                  55

<210> SEQ ID NO 58
<211> LENGTH: 9
<212> TYPE: PRT
<213> ORGANISM: Mus musculus

<400> SEQUENCE: 58

Leu Gln Tyr Asp Glu Phe Pro Tyr Thr
1               5

<210> SEQ ID NO 59
<211> LENGTH: 352
<212> TYPE: DNA
<213> ORGANISM: Mus musculus

<400> SEQUENCE: 59
gaggtgcagc tgcaggagtc tggacctgtg ctggtgaagc ctggggcttc agtgaagatg      60
tcctgtaagg cttctggata cacattcact gactactata tgaactgggt gaagcagagc     120
catggaaaga gccttgagtg gattggagtt attaatcctt acaacggtgg tactagctac     180
aaccagaagt tcaagggcaa ggccacattg actgttgaca gtcctccag cacagcctac      240 atggagctca acagcctgac atctgaggac tctgcagtct attactgtgc aagacggcga     300
```
ggctatgcta tggactactg gggtcaagga acctcagtca ccgtctcctc ag      352

<210> SEQ ID NO 60
<211> LENGTH: 117
<212> TYPE: PRT
<213> ORGANISM: Mus musculus

<400> SEQUENCE: 60

Glu Val Gln Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Arg Gly Tyr Ala Met Asp Tyr Trp Gly Gln Gly Thr Ser
            100                 105                 110

Val Thr Val Ser Ser
        115

<210> SEQ ID NO 61
<211> LENGTH: 322
<212> TYPE: DNA
<213> ORGANISM: Mus musculus

<400> SEQUENCE: 61
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcagctcct ggtctataat gcaaaaacct tagcagaagg tgtgccatca     180
aggttcagtg gcagtggatc aggcacacag ttttctctga agatcaacag cctgcagcct     240
gaagattttg ggagttatta ctgtcaacat cattatggta ctccgtacac gttcggaggg     300
gggaccaacc tggaaataaa ac                                              322

<210> SEQ ID NO 62
<211> LENGTH: 107
<212> TYPE: PRT
<213> ORGANISM: Mus musculus

<400> SEQUENCE: 62

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Tyr
                85                  90                  95

Thr Phe Gly Gly Gly Thr Asn Leu Glu Ile Lys
            100                 105

<210> SEQ ID NO 63
<211> LENGTH: 8
<212> TYPE: PRT
<213> ORGANISM: Mus musculus

<400> SEQUENCE: 63

Gly Tyr Thr Phe Thr Asp Tyr Tyr
1               5

<210> SEQ ID NO 64
<211> LENGTH: 8
<212> TYPE: PRT
<213> ORGANISM: Mus musculus

<400> SEQUENCE: 64

Ile Asn Pro Tyr Asn Gly Gly Thr
1               5

<210> SEQ ID NO 65
<211> LENGTH: 10
<212> TYPE: PRT
<213> ORGANISM: Mus musculus

<400> SEQUENCE: 65

Ala Arg Arg Arg Gly Tyr Ala Met Asp Tyr
1               5                   10

<210> SEQ ID NO 66
<211> LENGTH: 6
<212> TYPE: PRT
<213> ORGANISM: Mus musculus

<400> SEQUENCE: 66

Glu Asn Ile Tyr Ser Tyr
1               5

<210> SEQ ID NO 67
<211> LENGTH: 56
<212> TYPE: PRT
<213> ORGANISM: Mus musculus

<400> SEQUENCE: 67

Leu Ala Trp Tyr Gln Gln Lys Gln Gly Lys Ser Pro Gln Leu Leu Val
1               5                   10                  15

Tyr Asn Ala Lys Thr Leu Ala Glu Gly Val Pro Ser Arg Phe Ser Gly
            20                  25                  30

Ser Gly Ser Gly Thr Gln Phe Ser Leu Lys Ile Asn Ser Leu Gln Pro
        35                  40                  45

Glu Asp Phe Gly Ser Tyr Tyr Cys
    50                  55

<210> SEQ ID NO 68
<211> LENGTH: 8
<212> TYPE: PRT
<213> ORGANISM: Mus musculus

<400> SEQUENCE: 68

His His Tyr Gly Thr Pro Tyr Thr
1               5

<210> SEQ ID NO 69
<211> LENGTH: 352
<212> TYPE: DNA
<213> ORGANISM: Mus musculus

<400> SEQUENCE: 69

```
gaggtgcagc tgcaggagtc tggtggagga ttggtgcagc ctaaagggtc attgaaactc        60
tcatgtgcag cctctggatt cagcttcaat acctacgcca tgaactgggt ccgccaggct       120
ccaggaaagg gtttggaatg ggttgctcgc ataagaagta aaagtaataa ttatgcaaca       180
tattatgccg attcagtgaa agacagattc accatctcca gagatgattc agaaagcatg       240
ctctatctgc aaatgaacaa cttgaaaact gaggacacag ccatgtatta ctgtgtgaga       300
ctgggagcta tggactactg gggtcaagga acctcagtca ccgtctcctc ag              352
```

<210> SEQ ID NO 70
<211> LENGTH: 117
<212> TYPE: PRT
<213> ORGANISM: Mus musculus

<400> SEQUENCE: 70

Glu Val Gln Leu Gln Glu Ser Gly Gly Gly Leu Val Gln Pro Lys Gly
1               5                   10                  15

Ser Leu Lys Leu Ser Cys Ala Ala Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Thr Glu Asp Thr Ala Met Tyr
                85                  90                  95

Tyr Cys Val Arg Leu Gly Ala Met Asp Tyr Trp Gly Gln Gly Thr Ser
            100                 105                 110

Val Thr Val Ser Ser
        115

<210> SEQ ID NO 71
<211> LENGTH: 322
<212> TYPE: DNA
<213> ORGANISM: Mus musculus

<400> SEQUENCE: 71

```
gacattgtga tgacccagtc tcaaaaattc atgtccacat cagtaggaga cagggtcagc        60
gtcacctgca aggccagtca gaatgtgggt actaatgtag cctggtatca acagaaacca       120
gggcaatctc ctaaagcact gatttactcg gcatcctacc ggtacagtgg agtccctgat       180
cgcttcacag gcagtggatc tgggacagat ttcactctca ccatcagcaa tgtgcagtct       240
gaagacttgg cagagtattt ctgtcagcaa tataacagct atccgctcac gttcggtgct       300
gggaccaagc tggagctgaa ac                                                322
```

<210> SEQ ID NO 72
<211> LENGTH: 106
<212> TYPE: PRT
<213> ORGANISM: Mus musculus

<400> SEQUENCE: 72

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu
            100                 105

<210> SEQ ID NO 73
<211> LENGTH: 8
<212> TYPE: PRT
<213> ORGANISM: Mus musculus

<400> SEQUENCE: 73

Gly Phe Ser Phe Asn Thr Tyr Ala
1               5

<210> SEQ ID NO 74
<211> LENGTH: 10
<212> TYPE: PRT
<213> ORGANISM: Mus musculus

<400> SEQUENCE: 74

Ile Arg Ser Lys Ser Asn Asn Tyr Ala Thr
1               5                   10

<210> SEQ ID NO 75
<211> LENGTH: 8
<212> TYPE: PRT
<213> ORGANISM: Mus musculus

<400> SEQUENCE: 75

Val Arg Leu Gly Ala Met Asp Tyr
1               5

<210> SEQ ID NO 76
<211> LENGTH: 6
<212> TYPE: PRT
<213> ORGANISM: Mus musculus

<400> SEQUENCE: 76

Gln Asn Val Gly Thr Asn
1               5

<210> SEQ ID NO 77
<211> LENGTH: 56
<212> TYPE: PRT
<213> ORGANISM: Mus musculus

<400> SEQUENCE: 77

Val Ala Trp Tyr Gln Gln Lys Pro Gly Gln Ser Pro Lys Ala Leu Ile
1               5                   10                  15

Tyr Ser Ala Ser Tyr Arg Tyr Ser Gly Val Pro Asp Arg Phe Thr Gly
            20                  25                  30

Ser Gly Ser Gly Thr Asp Phe Thr Leu Thr Ile Ser Asn Val Gln Ser
        35                  40                  45

Glu Asp Leu Ala Glu Tyr Phe Cys
    50                  55

<210> SEQ ID NO 78
<211> LENGTH: 8
<212> TYPE: PRT
<213> ORGANISM: Mus musculus

<400> SEQUENCE: 78

Gln Tyr Asn Ser Tyr Pro Leu Thr
1               5

<210> SEQ ID NO 79
<211> LENGTH: 358
<212> TYPE: DNA
<213> ORGANISM: Mus musculus

<400> SEQUENCE: 79
gaggtgcagc tgcaggagtc tggacctgtg ctggtgaagc ctggggcttc agtgaagatg    60
tcctgtaagg cttctggata cacattcact gactactata tgaactgggt gaagcagagc   120
catggaaaga gccttgagtg gattggagtt attaatcctt acaacggtgg tactagctac   180
aaccagaagt tcaagggcaa ggccacattg actgttgaca gtcctccag cacagcctac   240 atggagctca acagcctgac atctgaggac tctgcagtct attactgtgc atctttacga   300
cgccggactg actactttga ctactggggc caaggcacca ctctcacagt ctcctcag    358

<210> SEQ ID NO 80
<211> LENGTH: 119
<212> TYPE: PRT
<213> ORGANISM: Mus musculus

<400> SEQUENCE: 80

Glu Val Gln Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Ser Leu Arg Arg Arg Thr Asp Tyr Phe Asp Tyr Trp Gly Gln Gly
            100                 105                 110

Thr Thr Leu Thr Val Ser Ser
        115

<210> SEQ ID NO 81
<211> LENGTH: 321
<212> TYPE: DNA
<213> ORGANISM: Mus musculus

<400> SEQUENCE: 81
gacattgtga tgacccagtc tcacaaattc atgtccacat cagtaggaga cagggtcagc    60

```
atcacctgca aggccagtca ggatgtgggt actgctgtag cctggtatca acagaaacca    120
gggcaatctc ctaaactact gatttactgg gcatccaccc ggcacactgg agtccctgat    180
cgcttcacag gcagtggatc tgggacagat ttcactctca ccattagcaa tgtgcagtct    240
gaagacttgg cagattattt ctgtcagcaa tatagcagct atcctctcac gttcggtgct    300
gggaccaagc tggagctgaa a                                              321
```

<210> SEQ ID NO 82
<211> LENGTH: 107
<212> TYPE: PRT
<213> ORGANISM: Mus musculus

<400> SEQUENCE: 82

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 83
<211> LENGTH: 8
<212> TYPE: PRT
<213> ORGANISM: Mus musculus

<400> SEQUENCE: 83

Gly Tyr Thr Phe Thr Asp Tyr Tyr
1               5

<210> SEQ ID NO 84
<211> LENGTH: 8
<212> TYPE: PRT
<213> ORGANISM: Mus musculus

<400> SEQUENCE: 84

Ile Asn Pro Tyr Asn Gly Gly Thr
1               5

<210> SEQ ID NO 85
<211> LENGTH: 12
<212> TYPE: PRT
<213> ORGANISM: Mus musculus

<400> SEQUENCE: 85

Ala Ser Leu Arg Arg Arg Thr Asp Tyr Phe Asp Tyr
1               5                   10

<210> SEQ ID NO 86
<211> LENGTH: 6
<212> TYPE: PRT
<213> ORGANISM: Mus musculus

<400> SEQUENCE: 86

Gln Asp Val Gly Thr Ala
1               5

<210> SEQ ID NO 87
<211> LENGTH: 56
<212> TYPE: PRT
<213> ORGANISM: Mus musculus

<400> SEQUENCE: 87

Val Ala Trp Tyr Gln Gln Lys Pro Gly Gln Ser Pro Lys Leu Leu Ile
1               5                   10                  15

Tyr Trp Ala Ser Thr Arg His Thr Gly Val Pro Asp Arg Phe Thr Gly
            20                  25                  30

Ser Gly Ser Gly Thr Asp Phe Thr Leu Thr Ile Ser Asn Val Gln Ser
        35                  40                  45

Glu Asp Leu Ala Asp Tyr Phe Cys
    50                  55

<210> SEQ ID NO 88
<211> LENGTH: 8
<212> TYPE: PRT
<213> ORGANISM: Mus musculus

<400> SEQUENCE: 88

Gln Tyr Ser Ser Tyr Pro Leu Thr
1               5

<210> SEQ ID NO 89
<211> LENGTH: 355
<212> TYPE: DNA
<213> ORGANISM: Mus musculus

<400> SEQUENCE: 89
gaggtgcagc tgcaggagtc tggcgctgag ttggtgaaac ctggagcttc agtgaagata      60
tcctgcaagg tttctggcta caccttcact gaccatacta ttcactggat gaagcagagg     120
cctgaacagg gcctggaatg gattggatat atttatccta gagatggtag tactaagtac     180
aatgagaagt tcaagggcaa ggccacattg actgcagaca atcctccag cacagcctac      240 atgcagctca acagcctgac atctgaggac tctgcagtct atttctgtgc aagaccgtat     300
gattacgcct ggtttgctta ctggggccaa gggactctgg tcactgtctc tgcag          355

<210> SEQ ID NO 90
<211> LENGTH: 118
<212> TYPE: PRT
<213> ORGANISM: Mus musculus

<400> SEQUENCE: 90

Glu Val Gln Leu Gln Glu Ser Gly Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

```
Met Gln Leu Asn Ser Leu Thr Ser Glu Asp Ser Ala Val Tyr Phe Cys
                85                  90                  95

Ala Arg Pro Tyr Asp Tyr Ala Trp Phe Ala Tyr Trp Gly Gln Gly Thr
            100                 105                 110

Leu Val Thr Val Ser Ala
            115

<210> SEQ ID NO 91
<211> LENGTH: 322
<212> TYPE: DNA
<213> ORGANISM: Mus musculus

<400> SEQUENCE: 91
gacatcttgc tgactcagtc tccagccatc ctgtctgtga gtccaggaga aagagtcagt    60
ttctcctgca gggccagtca gagcattggc acaagcatac actggtatca gcaaagaaca   120
aatggttctc caaggcttct cataaagtat gcttctgagt ctatctctgg gatcccttcc   180
aggtttagtg gcagtggatc aggacagat tttactctta gcatcaacag tgtggagtct   240
gaagatattg cagattatta ctgtcaacaa agtaatagct ggccattcac gttcggctcg   300
gggacaaagt tggaaataaa ac                                            322

<210> SEQ ID NO 92
<211> LENGTH: 107
<212> TYPE: PRT
<213> ORGANISM: Mus musculus

<400> SEQUENCE: 92

Asp Ile Leu Leu Thr Gln Ser Pro Ala Ile Leu Ser Val Ser Pro Gly
1               5                  10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro Phe
                85                  90                  95

Thr Phe Gly Ser Gly Thr Lys Leu Glu Ile Lys
            100                 105

<210> SEQ ID NO 93
<211> LENGTH: 8
<212> TYPE: PRT
<213> ORGANISM: Mus musculus

<400> SEQUENCE: 93

Gly Tyr Thr Phe Thr Asp His Thr
1               5

<210> SEQ ID NO 94
<211> LENGTH: 8
<212> TYPE: PRT
<213> ORGANISM: Mus musculus

<400> SEQUENCE: 94

Ile Tyr Pro Arg Asp Gly Ser Thr
1               5
```

<210> SEQ ID NO 95
<211> LENGTH: 11
<212> TYPE: PRT
<213> ORGANISM: Mus musculus

<400> SEQUENCE: 95

Ala Arg Pro Tyr Asp Tyr Ala Trp Phe Ala Tyr
1               5                   10

<210> SEQ ID NO 96
<211> LENGTH: 6
<212> TYPE: PRT
<213> ORGANISM: Mus musculus

<400> SEQUENCE: 96

Gln Ser Ile Gly Thr Ser
1               5

<210> SEQ ID NO 97
<211> LENGTH: 56
<212> TYPE: PRT
<213> ORGANISM: Mus musculus

<400> SEQUENCE: 97

Ile His Trp Tyr Gln Gln Arg Thr Asn Gly Ser Pro Arg Leu Leu Ile
1               5                   10                  15

Lys Tyr Ala Ser Glu Ser Ile Ser Gly Ile Pro Ser Arg Phe Ser Gly
            20                  25                  30

Ser Gly Ser Gly Thr Asp Phe Thr Leu Ser Ile Asn Ser Val Glu Ser
        35                  40                  45

Glu Asp Ile Ala Asp Tyr Tyr Cys
    50                  55

<210> SEQ ID NO 98
<211> LENGTH: 8
<212> TYPE: PRT
<213> ORGANISM: Mus musculus

<400> SEQUENCE: 98

Gln Ser Asn Ser Trp Pro Phe Thr
1               5

<210> SEQ ID NO 99
<211> LENGTH: 43
<212> TYPE: PRT
<213> ORGANISM: Homo sapiens

<400> SEQUENCE: 99

Met Asp Ala Glu Phe Arg His Asp Ser Gly Tyr Glu Val His His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala
        35                  40

<210> SEQ ID NO 100
<211> LENGTH: 147
<212> TYPE: PRT
<213> ORGANISM: Homo sapiens

<400> SEQUENCE: 100

```
Met Ala Ser His Arg Leu Leu Leu Cys Leu Ala Gly Leu Val Phe
 1               5                  10                  15

Val Ser Glu Ala Gly Pro Thr Gly Thr Gly Glu Ser Lys Cys Pro Leu
                20                  25                  30

Met Val Lys Val Leu Asp Ala Val Arg Gly Ser Pro Ala Ile Asn Val
            35                  40                  45

Ala Val His Val Phe Arg Lys Ala Ala Asp Asp Thr Trp Glu Pro Phe
50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
        130                 135                 140

Pro Lys Glu
145

<210> SEQ ID NO 101
<211> LENGTH: 127
<212> TYPE: PRT
<213> ORGANISM: Homo sapiens

<400> SEQUENCE: 101

Gly Pro Thr Gly Thr Gly Glu Ser Lys Cys Pro Leu Met Val Lys Val
 1               5                  10                  15

Leu Asp Ala Val Arg Gly Ser Pro Ala Ile Asn Val Ala Val His Val
                20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Glu Phe
50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
                100                 105                 110

Pro Tyr Ser Tyr Ser Thr Thr Ala Val Val Thr Asn Pro Lys Glu
            115                 120                 125

<210> SEQ ID NO 102
<211> LENGTH: 89
<212> TYPE: PRT
<213> ORGANISM: Homo sapiens

<400> SEQUENCE: 102

Met Gly Ile Leu Lys Leu Gln Val Phe Leu Ile Val Leu Ser Val Ala
 1               5                  10                  15

Leu Asn His Leu Lys Ala Thr Pro Ile Glu Ser His Gln Val Glu Lys
                20                  25                  30

Arg Lys Cys Asn Thr Ala Thr Cys Ala Thr Gln Arg Leu Ala Asn Phe
            35                  40                  45
```

```
Leu Val His Ser Cys Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70              75                      80

Arg Glu Pro Leu Asn Tyr Leu Pro Leu
                85
```

AMYLOID PROTOFIBRIL ANTIBODIES AND METHODS OF USE THEREOF

CROSS-REFERENCE TO RELATED APPLICATIONS

This application is a 35 U.S.C. § 371 US national stage application of International Patent Application No. PCT/US2014/058880, filed Oct. 2, 2014 and incorporated herein by reference in its entirety, which claims the benefit of U.S. Provisional Patent Application No. 61/885,593, filed Oct. 2, 2013 and incorporated herein by reference in its entirety.

STATEMENT REGARDING FEDERALLY SPONSORED RESEARCH OR DEVELOPMENT

Not Applicable.

INCORPORATION OF SEQUENCE LISTING

The sequence listing that is contained in the file named "49248_153657_ST25.txt", which is 52,291 bytes (measured in operating system MS-Windows), created on Mar. 31, 2016, is filed herewith by electronic submission and incorporated herein by reference in its entirety.

BACKGROUND OF THE INVENTION

Aggregation and deposition of misfolded proteins, known as amyloid, is a pathophysiological hallmark of approximately 20 human disorders collectively known as amyloid diseases (1-3). Human Islet Amyloid Poly Peptide (hIAPP) is a natively unstructured pancreatic endocrine hormone that regulates food intake and fat storage. It is co-secreted with insulin from pancreatic β-cells in response to glucose intake. In Type 2 diabetes mellitus (T2DM), hIAPP forms amyloid fibrils in the islets of Langerhans. Under the conditions of T2DM, hIAPP amyloid deposits in the Islets are toxic to β-cells. Several human and animal studies show that amyloid forms before β-cell deficiency and that the formation of oligomers and intracellular aggregates induces β-cell death (4, 5). In both type 1 (T1DM) and T2DM, IAPP release diminishes in parallel with the decrease in insulin release and conversely, IAPP levels are elevated in conditions of insulin resistance (high insulin secretion).

Most oral diabetes drugs lower blood glucose by stimulating the pancreas to release more insulin. Unfortunately, increased release of insulin is accompanied by increased release of hIAPP, which results in enhanced amyloid deposition, in turn leading to β-cell death and loss of natural insulin production. Therefore, these drugs do not cure the underlying cause of reduced insulin secretion. Rather, they manage hyperglycemia initially by stimulating insulin release, but in effect worsen the underlying problem and become progressively ineffective as β-cells die. This gradual loss of β-cells results in conversion of T2DM patients to iatrogenic T1DM patients (T2-T1DM) who require exogenous insulin supplements for blood glucose maintenance. In fact, drugs like Rosiglitazone and Metformin that work by improving insulin sensitivity and thereby reduce insulin demand have been shown to reduce the prevalence and severity of islet amyloid in transgenic mice. Several animal and human studies show that amyloid forms before β-cell deficiency and that formation of intracellular aggregates induces β-cell death. Amyloid fibrils and their pre-fibrillar aggregates exhibit toxicity in cell culture-based assays and it is thought that prevention of aggregation of pathogenic amyloid peptides might prevent disease progression.

Calnuc or Nucleobindin 1 (NUCB1) is a 55 kDa protein, which was first reported to be a growth and differentiation factor associated with lupus syndrome (Kanai et al., Immunol. Lett., 32, 43-48, 1992). Calnuc acquires its name from its DNA-binding and calcium binding ability. The NUCB1 (i.e. Calnuc) domain structure comprises, from N-terminus to C-terminus, a signal sequence at its N-terminus followed by a DNA binding domain of basic residues, an N-terminal proximal EF hand domain comprising a helix-loop-helix motif, an intervening acidic region, a second C-terminal proximal EF hand domain comprising a helix-loop-helix motif, and a leucine zipper domain (Miura et al., Biochem. Biophys. Res. Commun., 187, 375-380, 1992). Both the DNA binding domain and leucine zipper are crucial for binding of NUCB1 to DNA.

Recent studies have suggested that overexpression of NUCB1 down-regulates the mRNA production of Amyloid precursor protein (APP) and inhibits its biosynthesis (Lin et al., J. Neurochem., 100, 1505-14, 2007). Aggregation of Aβ isoforms generated from the sequential proteolytic cleavage of APP by β-(Beta Amyloid Cleaving Enzyme-1) and γ-secretase has been well characterized in Alzheimer's disease. In addition, abnormal calcium homeostasis has also been observed in the brains of demented patients. One study indicated that: i) NUCB1 binds to APP in a calcium dependent manner where binding is inhibited by Ca+2; ii) NUCB1 co-localizes with APP in vivo; iii) NUCB1 regulates APP protein levels by affecting APP synthesis; and that iv) the expression level of NUCB1 is decreased in the brains of Alzheimer's disease patients by 50% (Lin et al., J. Neurochem., 100, 1505-14, 2007). Nonetheless, Lin et al., (J. Neurochem., 100, 1505-14, 2007) did not indicate that NUCB1 could disaggregate amyloid fibrils or inhibit amyloid fibril formation.

It has also been shown that both: (i) $Ca^{2+}$-free soluble NUCB1 (sNUCB1) comprising an EF hand loop 1 domain, an intervening acidic region, an EF hand loop 2 domain; and, (ii) engineered sNUCB1 (tetramutant) comprising mutations in the EF-hand loop domains can inhibit the aggregation of both hIAPP and Aβ42 and decrease their toxicity in cell viability assays (WO 2010/009330). $Ca^{2+}$-free soluble sNUCB1 and the sNUCB1 (tetramutant) were also shown to disaggregate existing amyloid fibrils (WO 2010/009330). Various sNUCB1 mutants comprising an EF hand loop 1 domain, an intervening acidic region, an EF hand loop 2 domain but lacking sNUCB1 C-terminal residues 408-461 (sNUCB1(G408Ter), 401-461 (sNUCB1(Q401Ter)), and 333-461 (sNUCB1(W333Ter)) were also shown to inhibit aggregation of hIAPP (WO 2010/009330).

Using several amyloidogenic peptides, including hIAPP, engineered soluble forms of expressed Nucleobindin-1 (sNUCB1), a ubiquitous $Ca^{2+}$-binding protein, can inhibit amyloid formation and even disaggregate preformed fibrils (10). The mechanism of action of sNUCB1 is novel. The sNUCB1 protein apparently "caps" toxic protofibrillar species, reduces their toxicity, and prevents them from growing into mature fibrils. The sNUCB1-"capped" protofibrils are stable and can be isolated. The sNUCB1 binds to protofibrils that originate from amyloidogenic peptides, but it does not bind to the peptides themselves (10).

Conformation-specific antibodies have proven to be a powerful tool for detecting generic epitopes common to fibrils and are potentially therapeutic agents (6, 7, US Pat. Appl. Pub. No. 20100209422). Together, these antibodies have been useful in basic research to detect specific structural states of amyloidogenic proteins, and to shed light on the pathway of protein aggregation that leads to amyloid fibril formation. For example, the A11 antibody has been reported to specifically recognize a generic epitope common to prefibrillar oligomers of Aβ42 and not fibrils, monomers or natively folded Alzheimer's precursor proteins (8). In Alzheimer's Disease brain tissue, A11 stains punctate deposits but not diffuse plaques, indicating that diffuse deposits do not contain prefibrillar oligomers. These studies show the power of conformation-specific antibodies in teasing apart structural subtleties related to the molecular pathophysiology of amyloid disease.

SUMMARY

Stabilized conformation-specific antibodies ("scsAb") that recognize amyloid protofibrils, methods for raising the antibodies, methods of producing the antibodies, and the use of such antibodies in treatment and diagnosis of amyloid disease are provided herein. The "stabilized conformation-specific antibodies" (or "scsAb") provided herein recognize stabilized amyloid protofibrillar intermediates. In certain embodiments, the scsAb are sequence independent in that they are capable of binding distinct amyloid protofibrils comprising distinct amyloidogenic peptides. In certain embodiments, the scsAb are monoclonal antibodies (mAbs) raised against protofibrils using NUCB1-capped protofibrillar species as immunogens. The scsAb provided herein thus include, but are not limited to, antibodies made by any of the methods provided herein, antibodies constructed from any of the antibody sequences provided herein, and antibodies obtained or otherwise derived from any of the hybridoma cell lines provided herein. The use of the scsAb: i) as laboratory reagents in methods of detecting specific conformations of protofibrils comprised of amyloidogenic peptides; ii) in methods of detecting the presence of pre-fibrillar amyloid peptide species that may serve as biomarkers for amyloid diseases in patients; and/or iii) in methods of treating human or animal subjects against amyloid diseases is also provided herein. Also provided herein is the use of NUCB1-capped protofibrils as immunotherapeutic agents and as diagnostic agents. The use of detectably labelled and unlabelled NUCB1-capped amyloid protofibrils as agents for the detection of anti-amyloid protofibril antibodies in a subject, a subject sample, or any sample suspected of containing an anti-amyloid protofibril antibody is also provided herein.

Methods for obtaining an antibody that comprise exposing a host organism or an antibody display library to a NUCB1-capped amyloid protofibril, and selecting an antibody from said host or said library that specifically binds at least one amyloid protofibril are provided herein. In certain embodiments, the antibody does not specifically bind an isolated amyloid peptide monomer that is not assembled in an amyloid protofibril. In certain embodiments, the antibody specifically binds to two or more distinct amyloid protofibrils that are each comprised of distinct amyloid peptide monomers. In certain embodiments, the antibody is selected from the group consisting of a monoclonal antibody, a synthetic antibody, a chimeric antibody, a human antibody, an affinity matured antibody, a bispecific antibody, and a humanized antibody. In certain embodiments, the antibody is isolated by forming a hybridoma cell line with a cell from the host organism that produces the antibody and a myeloma cell line. In certain embodiments, the amyloid protofibril comprises an amyloid peptide selected from the group consisting of hIAPP, β23, and Aβ42. Also provided are antibodies obtained by the method of any one of aforementioned methods.

Isolated antibodies comprising at least one variable light chain (VL) region and/or at least one variable heavy chain (VH) region that specifically bind at least two distinct amyloid protofibrils that are each comprised of distinct amyloid peptide monomers are also provided.

A monoclonal antibody selected from the group consisting of 5a8.b11, 4a8.e11, 4b1.h9, 3f2.e10, 5c9.a2, and 7b6.b12 is also provided.

Antibodies comprising at least one heavy chain hypervariable region (HVR) selected from the group consisting of SEQ ID NO: 43, 44, 45, 53, 54, 55, 63, 64, 65, 73, 74, 75, 83, 84, 85, 93, 94, and 95, wherein the antibody specifically binds to an amyloid protofibril. In certain embodiments, the antibody further comprises at least one light chain hypervariable region (HVR) region selected from the group consisting of SEQ ID NO: 46, residues 18 to 20 of SEQ ID NO: 47, 48, 56, residues 18 to 20 of SEQ ID NO: 57, 58, 66, residues 18 to 20 of SEQ ID NO: 67, 68, 76, residues 18 to 20 of SEQ ID NO: 77, 78, 86, residues 18 to 20 of SEQ ID NO: 87, 88, 96, residues 18 to 20 of SEQ ID NO: 97, and SEQ ID NO: 98. In certain embodiments, the antibody comprises a heavy chain variable region selected from the group consisting of SEQ ID NO: 40, 50, 60, 70, 80, and 90. In certain embodiments, the antibody comprises a light chain variable region selected from the group consisting of SEQ ID NO: 42, 52, 62, 72, 82, and 92. In certain embodiments, the antibody comprises at least one of the HVR-H1, HVR-H2, and/or HVR-H3 sequences of mAb 5a8.b11 selected from the group consisting of SEQ ID NO: 43, 44, and 45 and/or at least one of the HVR-L1, HVR-L2, and/or HVR-L3 sequences of mAb 5a8.b11 selected from the group consisting of SEQ ID NO:46, residues 18 to 20 of SEQ ID NO: 47, and SEQ ID NO: 48. In certain embodiments, the antibody comprises at least one of the HVR-H1, HVR-H2, and/or HVR-H3 sequences of mAb 4a8.e11 selected from the group consisting of SEQ ID NO: 53, 54, and 55 and/or at least one of the HVR-L1, HVR-L2, and/or HVR-L3 sequences of mAb 4a8.e11 selected from the group consisting of SEQ ID NO: 56, residues 18 to 20 of SEQ ID NO: 57, and SEQ ID NO: 58. In certain embodiments, the antibody comprises at least one of the HVR-H1, HVR-H2, and/or HVR-H3 sequences of mAb 4b1.h9 selected from the group consisting of SEQ ID NO: 63, 64, and 65 and/or at least one of the HVR-L1, HVR-L2, and/or HVR-L3 sequences of mAb 4b1.h9 selected from the group consisting of SEQ ID NO: 66, residues 18 to 20 of SEQ ID NO: 67, and SEQ ID NO: 68. In certain embodiments, the antibody comprises at least one of the HVR-H1, HVR-H2, and/or HVR-H3 sequences of mAb 3f2.e10 selected from the group consisting of SEQ ID NO: 73, 74, and 75 and/or at least one of the HVR-L1, HVR-L2, and/or HVR-L3 sequences of mAb 3f2.e10 selected from the group consisting of SEQ ID NO: 76, residues 18 to 20 of SEQ ID NO: 77, and SEQ ID NO: 78. In certain embodiments, the antibody comprises at least one of the HVR-H1, HVR-H2, and/or HVR-H3 sequences of mAb 5c9.a2 selected from the group consisting of SEQ ID NO: 83, 84, and 85 and/or at least one of the HVR-L1, HVR-L2, and/or HVR-L3 sequences of mAb 5c9.a2 selected from the group consisting of SEQ ID NO: 86, residues 18 to 20 of SEQ ID NO: 87, and SEQ ID NO: 88. In certain embodiments, the antibody comprises at least one of the HVR-H1, HVR-H2, and/or HVR-H3 sequences of mAb 7b6.b12 selected from the group consisting of SEQ ID NO: 93, 94, and 95 and/or at least one of the HVR-L1, HVR-L2, and/or HVR-L3 sequences of mAb 7b6.b12 selected from the group consisting of SEQ ID NO:96, residues 18 to 20 of SEQ ID NO: 97, and SEQ ID NO: 98. In certain embodiments, the antibody comprises a VH region comprising the HVR H1, HVR H2, and HVR H3 of SEQ ID NO: 43, SEQ ID NO: 44, and SEQ ID NO: 45, respectively, and a VL region comprising the HVR L1, HVR L2, and HVR L3 sequences of SEQ ID NO: 46, residues 18 to 20 of SEQ ID NO: 47, and SEQ ID NO: 48, respectively. In certain embodiments, the antibody comprises a VH region comprising the HVR H1, HVRH2, and HVR H3 of SEQ ID NO: 53, SEQ ID NO: 54, and SEQ ID NO: 55, respectively, and a VL region comprising the HVR L1, HVR L2, and HVR L3 sequences of SEQ ID NO: 56, residues 18 to 20 of SEQ ID NO: 57, and SEQ ID NO: 58, respectively. In certain embodiments, the antibody comprises a VH region comprising the HVR H1, HVRH2, and HVR H3 of SEQ ID NO: 63, SEQ ID NO: 64, and SEQ ID NO: 65, respectively, and a VL region comprising the HVR L1, HVR L2, and HVR L3 sequences of SEQ ID NO: 66, residues 18 to 20 of SEQ ID NO: 67, and SEQ ID NO: 68, respectively. In certain embodiments, the antibody comprises a VH region comprising the HVR H1, HVRH2, and HVR H3 of SEQ ID NO: 73, SEQ ID NO: 74, and SEQ ID NO: 75, respectively, and a VL region comprising the HVR L1, HVR L2, and HVR L3 sequences of SEQ ID NO: 76, residues 18 to 20 of SEQ ID NO: 77, and SEQ ID NO: 78, respectively. In certain embodiments, the antibody comprises a VH region comprising the HVR H1, HVRH2, and HVR H3 of SEQ ID NO: 83, SEQ ID NO: 84, and SEQ ID NO: 85, respectively, and a VL region comprising the HVR L1, HVR L2, and HVR L3 sequences of SEQ ID NO: 86, residues 18 to 20 of SEQ ID NO: 87, and SEQ ID NO: 88, respectively. In certain embodiments, the antibody comprises a VH region comprising the HVR H1, HVRH2, and HVR H3 of SEQ ID NO: 93, SEQ ID NO: 94, and SEQ ID NO: 95, respectively, and a VL region comprising the HVR L1, HVR L2, and HVR L3 sequences of SEQ ID NO: 96, residues 18 to 20 of SEQ ID NO: 97, and SEQ ID NO: 98, respectively. Any of the aforementioned antibodies or other antibodies provided herein can also comprise at least one of any of the aforementioned HVR H1, HVRH2, HVR H3, HVR L1, HVR L2, and/or HVR L3 sequences wherein one, two, or three amino acids are substituted with a different amino acid. In certain embodiments, these amino acid substitutions in at least one of the HVR H1, HVRH2, HVR H3, HVR L1, HVR L2, and/or HVR L3 sequences are conservative amino acid substitutions.

Also provided herein are antibodies that specifically bind the same epitope as any of the aforementioned antibodies. In certain embodiments, an isolated antibody that binds the same epitope as a reference monoclonal antibody selected from the group consisting of 5a8.b11, 4a8.e11, 4b1.h9, 3f2.e10, 5c9.a2, and 7b6.b12 is provided. In certain embodiments, an isolated antibody that binds the same epitope as a reference monoclonal antibody that comprises the VH and VL regions of a monoclonal antibody selected from the group consisting of 5a8.b11, 4a8.e11, 4b1.h9, 3f2.e10, 5c9.a2, and 7b6.b12 is provided. In certain of any of the aforementioned embodiments, the epitope is an epitope found in at least one or at least two amyloid protofibrils or in at least one or at least two NUCB1-capped amyloid protofibrils, wherein the two amyloid protofibrils each comprise a distinct amyloid protein monomer. In any of the aforementioned embodiments, the distinct amyloid protein monomer can be selected from the group consisting of IAPP, transthyretin (TTR), mutant transthyretin (TTR), and Aβ42.

Also provided herein are antibodies that competitively inhibit binding of any of the aforementioned antibodies to at least one amyloid protofibril or that competitively inhibits binding to at least one NUCB1-capped amyloid protofibril. In certain embodiments, antibodies that competitively inhibit binding of any of the aforementioned antibodies to at least two amyloid protofibrils or that competitively inhibits binding to at least two NUCB1-capped amyloid protofibrils, wherein the two amyloid protofibrils each comprise a distinct amyloid protein monomer, are provided. In certain embodiments, an isolated antibody that competitively inhibits binding of a reference monoclonal antibody selected from the group consisting of 5a8.b11, 4a8.e11, 4b1.h9, 3f2.e10, 5c9.a2, and 7b6.b12 to at least one amyloid protofibril or that competitively inhibits binding of a reference monoclonal antibody selected from the group consisting of 5a8.b11, 4a8.e11, 4b1.h9, 3f2.e10, 5c9.a2, and 7b6.b12 to at least one NUCB1-capped amyloid protofibril is provided. In certain embodiments, an isolated antibody that competitively inhibits binding of a reference monoclonal antibody selected from the group consisting of 5a8.b11, 4a8.e11, 4b1.h9, 3f2.e10, 5c9.a2, and 7b6.b12 to at least two amyloid protofibrils or that competitively inhibits binding of a reference monoclonal antibody selected from the group consisting of 5a8.b11, 4a8.e11, 4b1.h9, 3f2.e10, 5c9.a2, and 7b6.b12 to at least two NUCB1-capped amyloid protofibril, wherein the two amyloid protofibrils each comprise a distinct amyloid protein monomer, is provided. In certain embodiments, an isolated antibody that competitively inhibits binding of a reference monoclonal antibody that comprises the VH and VL regions of a monoclonal antibody selected from the group consisting of 5a8.b11, 4a8.e11, 4b1.h9, 3f2.e10, 5c9.a2, and 7b6.b12 to at least one amyloid protofibril or that competitively inhibits binding of a reference monoclonal antibody that comprises the VH and VL regions of a monoclonal antibody selected from the group consisting of 5a8.b11, 4a8.e11, 4b1.h9, 3f2.e10, 5c9.a2, and 7b6.b12 to at least one NUCB1-capped amyloid protofibril is provided. In certain embodiments, an isolated antibody that competitively inhibits binding of a reference monoclonal antibody that comprises the VH and VL regions of a monoclonal antibody selected from the group consisting of 5a8.b11, 4a8.e11, 4b1.h9, 3f2.e10, 5c9.a2, and 7b6.b12 to at least two amyloid protofibrils or that competitively inhibits binding of a reference monoclonal antibody that comprises the VH and VL regions of a monoclonal antibody selected from the group consisting of 5a8.b11, 4a8.e11, 4b1.h9, 3f2.e10, 5c9.a2, and 7b6.b12 to at least two NUCB1-capped amyloid protofibrils, wherein the two amyloid protofibrils each comprise a distinct amyloid protein monomer, is provided. In any of the aforementioned embodiments, the distinct amyloid protein monomer can be selected from the group consisting of IAPP, TTR, mutant transthyretin (TTR), and Aβ42.

Also provided are compositions comprising any of the aforementioned antibodies and a carrier. Also provided are recombinant nucleic acid molecules comprising a nucleic acid encoding any of the aforementioned antibodies. In certain embodiments, the recombinant nucleic acid molecules can comprise a heterologous promoter that is operably linked to a nucleic acid encoding any of the aforementioned antibodies. In certain embodiments, a recombinant nucleic acid encoding a polypeptide comprising a variable heavy chain of any of the aforementioned antibodies, a nucleic acid encoding a polypeptide comprising a variable light chain of any of the aforementioned antibodies, or a nucleic acid encoding both the heavy and light chains of any of the aforementioned antibodies are provided. Also provided are cells comprising any of the aforementioned recombinant nucleic acids. Also provided are methods for producing an antibody comprising culturing any of the aforementioned cells under conditions that provide for the expression of said encoded antibody and harvesting said antibody from said cell or from the medium in which the cell was cultured. In certain embodiments, methods for producing any of the aforementioned antibodies or fragments thereof comprising culturing the aforementioned cells under conditions that provide for the expression of said encoded heavy chain hypervariable region (HVR), light chain hypervariable region (HVR) region, heavy chain variable region, or light chain variable region and harvesting said antibody or fragment thereof from said cell or from the medium in which the cell was cultured are provided.

Recombinant nucleic acid molecules that encode any of: (a) at least one heavy chain hypervariable region (HVR) selected from the group consisting of SEQ ID NO:43, 44, 45, 53, 54, 55, 63, 64, 65, 73, 74, 75, 83, 84, 85, 93, 94, and 95; (b) at least one light chain hypervariable region (HVR) region selected from the group consisting of SEQ ID NO:46, residues 18 to 20 of SEQ ID NO: 47, 48, 56, residues 18 to 20 of SEQ ID NO: 57, 58, 66, residues 18 to 20 of SEQ ID NO: 67, 68, 76, residues 18 to 20 of SEQ ID NO: 77, 78, 86, residues 18 to 20 of SEQ ID NO: 87, 88, 96, residues 18 to 20 of SEQ ID NO: 97, and SEQ ID NO:98; (c) a heavy chain variable region selected from the group consisting of SEQ ID NO: 40, 50, 60, 70, 80, and 90; (d) a light chain variable region selected from the group consisting of SEQ ID NO: 42, 52, 62, 72, 82, and 92; or (e) any combination of (a)-(d), wherein said sequence of (a), (b), (c), (d), or (e) is operably linked to at least one heterologous sequence selected from the group consisting of a promoter, coding sequence, or polyadenylation sequence are also provided. In certain embodiments, a recombinant nucleic acid encoding a polypeptide comprising a variable heavy chain of any of the aforementioned antibodies, a nucleic acid encoding a polypeptide comprising a variable light chain of any of the aforementioned antibodies, or a nucleic acid encoding both the heavy and light chains of any of the aforementioned antibodies are provided. Also provided are cells comprising any of the aforementioned recombinant nucleic acids. Also provided are methods for producing an antibody comprising culturing any of the aforementioned cells under conditions that provide for the expression of said encoded antibody and harvesting said antibody from said cell or from the medium in which the cell was cultured. In certain embodiments, methods for producing any of the aforementioned antibodies or fragments thereof comprising culturing the aforementioned cells under conditions that provide for the expression of said encoded heavy chain hypervariable region (HVR), light chain hypervariable region (HVR) region, heavy chain variable region, or light chain variable region and harvesting said antibody or fragment thereof from said cell or from the medium in which the cell was cultured are provided.

Methods for preventing or treating an amyloid disease that comprises administering to a subject in need thereof a therapeutically effective dose of any of the aforementioned antibodies are also provided. In certain embodiments, the amyloid disease is selected from the group consisting of Type 2 diabetes mellitus-associated amyloidosis, Alzheimer's disease (AD), Parkinson's disease (PD), Familial Amyloid Cardiomyopathy (FAC), Familial Amyloid Polyneuropathy (FAP), Non-V30M Familial Amyloid Polyneuropathy (FAP), Central Nervous System Selective Amyloidosis (CNSA), and Huntington's disease. In certain embodiments, the amyloid disease is Type 2 diabetes mellitus-associated amyloidosis and the antibody is selected from the group consisting of 5c9.a2, 5a8.b11, 4a8.e11, 4b1.h9, 3f2.e10, and 7b6.b12 or an antibody comprising light chain and heavy chain hypervariable (HVR) regions of 5c9.a2, 5a8.b11, 4a8.e11, 4b1.h9, 3f2.e10, or 7b6.b12. In certain embodiments, the disease is Alzheimer's disease (AD) and the antibody is selected from the group consisting of 5c9.a2, 5a8.b11, 4a8.e11, 4b1.h9, 3f2.e10, and 7b6.b12, an antibody comprising light chain and heavy chain hypervariable (HVR) regions of 5c9.a2, 5a8.b11, 4a8.e11, 4b1.h9, 3f2.e10, or 7b6.b12, or an antibody comprising the light chain and heavy chain \ regions of 5c9.a2, 5a8.b11, 4a8.e11, 4b1.h9, 3f2.e10, or 7b6.b12. In certain embodiments, the amyloid disease is selected from the group consisting of Familial Amyloid Cardiomyopathy (FAC), Familial Amyloid Polyneuropathy (FAP), non-V30M Familial Amyloid Polyneuropathy (FAP), Central and Nervous System Selective Amyloidosis (CNSA) and the antibody is an antibody that binds the same epitope as a 5c9.a2 reference monoclonal antibody.

Methods for monitoring amyloid disease in a subject that comprise exposing a subject sample to any of the aforementioned antibodies and determining levels of immunoreactive material in the subject, wherein an increase in immunoreactive material of said subject sample to said antibody relative to a control sample indicates an increase in amyloid protofibril accumulation in said subject and amyloid disease predisposition, presence, and/or progression are also provided. In certain embodiments, the amyloid protofibril is amyloid beta 42 (Aβ42) and the antibody comprises light chain and heavy chain hypervariable (HVR) regions of 5c9.a2, 5a8.b11, 4a8.e11, 4b1.h9, 3f2.e10, or 7b6.b12 or is an antibody is selected from the group consisting of 5c9.a2, 5a8.b11, 4a8.e11, 4b1.h9, 3f2.e10, and 7b6.b12. In certain embodiments of the methods, the amyloid protofibril comprises wild type or mutant transthyretin (TTR) monomers and the antibody binds the same epitope as a 5c9.a2 reference monoclonal antibody.

Methods for detecting an amyloid protofibril comprising exposing a sample suspected of containing an amyloid protofibril to any of the aforementioned antibodies and determining levels of immunoreactive material in the sample, wherein an increase in immunoreactive material of said sample to said antibody relative to a control sample indicates an increased concentration of said amyloid protofibril in said sample are provided. In certain embodiments, the amyloid protofibril is amyloid beta 42 (Aβ42) and the antibody comprises light chain and heavy chain hypervariable (HVR) regions of 5c9.a2, 5a8.b11, 4a8.e11, 4b1.h9, 3f2.e10, or 7b6.b12 or is an antibody is selected from the group consisting of 5c9.a2, 5a8.b11, 4a8.e11, 4b1.h9, 3f2.e10, and 7b6.b12. In certain embodiments of the methods, the amyloid protofibril comprises wild type or mutant transthyretin (TTR) monomers and the antibody binds the same epitope as a 5c9.a2 reference monoclonal antibody.

Kits comprising pharmaceutical or veterinary compositions comprising any of the aforementioned scsAb are also provided herein. Also provided are kits comprising a labelled or unlabeled scsAb and optionally one or more reagents that are useful for detecting and/or diagnosing an amyloid disease. Such kits can be for use in treating, detecting, or diagnosing an amyloid associated disease. In certain embodiments, the kit can be used for treating, detecting, or diagnosing an amyloid-associated disease selected from the group consisting of Alzheimer's, Parkinson's, Huntington's, Prion diseases, Type 2 Diabetes Mellitus, Dialysis-related amyloidosis, Amyotrophic lateral sclerosis, Pick's Disease, Senile systemic amyloidosis, Machado-Joseph Disease, Gelsolin Amyloid Disease, Primary systemic amyloidosis, Secondary systemic amyloidosis, Familial non-neuropathic amyloidosis, Familial subepithelial corneal amyloid, Hereditary renal amyloidosis, Pituitary-gland amyloidosis, Injection-localized amyloidosis, Atrial amyloidosis, Familial British dementia, Hereditary cerebral amyloid angiopathy, Familial amyloid polyneuropathy III, Familial Amyloid Cardiomyopathy (FAC), Familial Amyloid Polyneuropathy (FAP), Non-V30M Familial Amyloid Polyneuropathy (FAP), Central Nervous System Selective Amyloidosis (CNSA), and Chronic obstructive pulmonary disease. In certain embodiments, a kit comprising: a pharmaceutical or veterinary composition comprising (i) a therapeutically effective amount of a scsAb, is provided. In certain embodiments, a kit comprising: (a) a pharmaceutical or veterinary composition comprising (i) a therapeutically effective amount of a scsAb; and (ii) a pharmaceutically acceptable carrier; and, (iii) one or more containers for the pharmaceutical or veterinary composition(s) or (b) a labelled or unlabeled scsAb and one or more reagents and/or apparati for detection of amyloid protofibrils and/or diagnosis of amyloid disease is provided. In other embodiments, the kit can further comprise a device or apparatus that provides for administration of the pharmaceutical or veterinary composition to a subject in need thereof or for detection or diagnosis of amyloid disease in the subject. In certain embodiments useful for detection or diagnosis of amyloid disease, such components could comprise any type of solid matrix wherein a scsAb is covalently or non-covalently coupled. In still other embodiments, the kit can further comprise instructions for use in treating, detecting, or diagnosing an amyloid associated disease. In certain embodiments of such kits provided herein, the composition is a pharmaceutical composition and the subject is a human. In other embodiments of such kits provided herein, the composition is a veterinary composition and the subject is an animal other than a human. When the composition is a veterinary composition, the animal can be a non-human primate, horse, cow, pig, dog, or cat.

Methods of treating subjects suffering from amyloidosis with therapeutically effective amounts of any of the aforementioned pharmaceutical or veterinary compositions comprising any of the aforementioned scsAb also provided herein. In certain embodiments, the subject is a human suffering from amyloidosis of the brain. In such subjects, amyloidosis of the brain can comprise an accumulation of amyloid beta fibrils. In still other embodiments, the subject is a human suffering from amyloidosis of the pancreas. In such human subjects, the amyloidosis of the pancreas can comprise an accumulation of amylin fibrils. In certain embodiments where the subject is a human, the human can be suffering from an amyloid associated disease selected from the group consisting of Alzheimer's, Parkinson's, Huntington's, Prion diseases, Type 2 Diabetes Mellitus, Dialysis-related amyloidosis, Amyotrophic lateral sclerosis, Pick's Disease, Senile systemic amyloidosis, Machado-Joseph Disease, Gelsolin Amyloid Disease, Primary systemic amyloidosis, Secondary systemic amyloidosis, Familial non-neuropathic amyloidosis, Familial subepithelial corneal amyloid, Hereditary renal amyloidosis, Pituitary-gland amyloidosis, Injection-localized amyloidosis, Atrial amyloidosis, Familial British dementia, Hereditary cerebral amyloid angiopathy, Familial amyloid polyneuropathy III, Familial Amyloid Cardiomyopathy (FAC), Familial Amyloid Polyneuropathy (FAP), Non-V30M Familial Amyloid Polyneuropathy (FAP), Central Nervous System Selective Amyloidosis (CNSA), and Chronic obstructive pulmonary disease.

In other embodiments where the composition comprising a scsAb is a veterinary composition, the subject can be an animal that is not a human. Such animals can be a non-human primate, horse, cow, pig, dog, or cat. In certain embodiments, the animal is suffering from renal or hepatic amyloidosis.

In certain embodiments of the aforementioned methods of use, a therapeutically effective amount of a pharmaceutical composition is administered by parenteral injection, by injection into an organ, intrathecal injection, implantation of a pump, stereotactic delivery, implantation of a cannula, implantation of a three-dimensional implant, or implantation of microspheres.

Methods of treating subjects suffering from amyloidosis with scsAb are also provided. Also provided herein is the use of scsAb as therapeutic agents, as diagnostic agents, or as laboratory reagents.

Also provided herein are pharmaceutical or veterinary compositions comprising nucleic acids that encode any of the aforementioned scsAb. In certain embodiments, a pharmaceutical or veterinary composition comprising (i) a nucleic acid that encodes a scsAb, and a pharmaceutically acceptable or veterinary carriers is provided. Methods of making such pharmaceutical or veterinary compositions are provided. Methods of using therapeutically effective amounts of such pharmaceutical or veterinary compositions to treat a subject suffering from amyloidosis are also provided.

Methods for inhibiting amyloid fibril formation, comprising the step of contacting a cell comprising either a peptide capable of forming amyloid fibrils or an amyloid protofibril with an exogenously provided scsAb are also provided. In certain embodiments of these methods, the scsAb is provided to a cell comprising a peptide capable of forming amyloid fibrils or to a cell-free composition comprising a peptide capable of forming amyloid fibrils or an amyloid protofibril. In certain embodiments of these methods, the peptide is selected from the group consisting of hIAPP, α-synuclein, Aβ42, TTR, mutants of TTR, and NFTs of tau.

Also provided are isolated NUCB1-capped amyloid protofibrils that are covalently or non-covalently linked to a detectable label. In certain embodiments, the detectable label is selected from the group consisting of a magnetic resonance imaging (MRI) contrast agent, a radioisotope, a heterologous epitope, a fluorophore, a nanoparticle, and an enzyme. In certain embodiments, the amyloid protofibril comprises an amyloid peptide selected from the group consisting of hIAPP, β23, TTR, a TTR mutant, alpha-synuclein, and Aβ42. Also provided are methods for monitoring amyloid disease in a subject that comprises exposing the subject or a subject sample to a NUCB1-capped amyloid protofibril or to any of the aforementioned NUCB1-capped amyloid protofibrils that are detectably labelled and measuring binding of the NUCB1-capped amyloid protofibril to endogenous anti-amyloid protofibril antibodies in the subject or subject sample, wherein an increase in binding of the NUCB1-capped amyloid protofibril to endogenous anti-amyloid protofibril antibodies in the subject or in the subject sample relative to a control subject or control subject sample, respectively, indicates an increase in endogenous anti-amyloid protofibril antibodies in said subject and amyloid disease predisposition, presence, and/or progression. Also provided are methods for detecting an anti-amyloid protofibril antibody in a sample comprising exposing one or more samples suspected of containing an anti-protofibril antibody to a NUCB1-capped amyloid protofibril or to any of the aforementioned NUCB1-capped amyloid protofibrils that are detectably labelled and measuring binding of the NUCB1-capped amyloid protofibril to antibodies in the sample, wherein an increase in binding of the NUCB1-capped amyloid protofibril to said antibody in the sample relative to a control sample indicates the presence of an anti-amyloid protofibril in said sample.

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 2 shows the characteristics of amyloid intermediates compared with NUCB1-capped protofibril antigen (i.e. immunogen used herein).

FIGS. 4A and B show that NUCB1-capped protofibrils can be isolated and used as antigen for the development of protofibril-specific antibodies. (A) Purification of NUCB1-capped protofibrils by size-exclusion chromatography (left) and detection of NUCB1 or hIAPP in peak fractions (right). (B) The protocol for the development and screening of monoclonal antibodies involves the immunization of mice with the Peak 1 fraction, hybridoma fusion and screening of resultant hybridoma clones.

FIGS. 6A, B, C show that the conformation-specific monoclonal antibody 5a8.b11 stains pyramidal cells in Familial Alzheimer's Disease (FAD) human brain tissue. (A) Human cortex tissue from either normal healthy controls or patients with FAD were stained with no primary antibody, anti-Aβ42, mAb 3b10.e9, or mAb 5a8.b11. The results show staining of FAD cortex with anti-Aβ42, and mAb 5a8.b11, but not with mAb 3b10.e9 or secondary antibody alone. (B) Representative pyramidal cells from FAD cortex stained with no primary antibody, anti-Aβ42, mAb3b10.e9, or mAb 5a8.b11 shows positive staining with anti-Aβ42 and mAb 5a8.b11. (C) Quantification of the relative staining of pyramidal cells (n=8) shows significant staining with Aβ42, and mAb 5a8.b11 compares with control (P<0.01).

FIG. 7 shows an alignment of the sequence of the light and heavy chains of certain scsAb. The aligned light chain sequences are from 5a8.b11 (SEQ ID NO:40), 4a8.e11 (SEQ ID NO:50), 4b1.h9 (SEQ ID NO:60), 3f2.e10 (SEQ ID NO:70), 5c9.a2 (SEQ ID NO:80), and 7b6.b12 (SEQ ID NO:90). The aligned heavy chain sequences are from 5a8.b11 (SEQ ID NO: 42), 4a8.e11 (SEQ ID NO:52), 4b1.h9 (SEQ ID NO:62), 3f2.e10 (SEQ ID NO:72), 5c9.a2 (SEQ ID NO:82), and 7b6.b12 (SEQ ID NO:92).

FIG. 9 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 5a8.b11. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 5a8.b11 are respectively provided as SEQ ID NO:39-48 in Table 5.

FIG. 10 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 4a8.e11. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 4a8.e11 are respectively provided as SEQ ID NO:49-58 in Table 5.

FIG. 11 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 4b1.h9. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 4b1.h9 are respectively provided as SEQ ID NO:59-68 in Table 5.

FIG. 12 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 3f2.e10. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 3f2.e10 are respectively provided as SEQ ID NO:69-78 in Table 5.

FIG. 13 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 5c9.a2. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 5c9.a2 are respectively provided as SEQ ID NO:79-88 in Table 5.

FIG. 14 shows the heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), HVR-L3 (CDR3), and framework regions (FWR; FR1, FR2, FR3, FR4) of the heavy and light chains of monoclonal antibody 7b6.b12. The heavy chain DNA, heavy chain protein, light chain (kappa) DNA, light chain (kappa) protein, HVR H1 (CDR1), HVR H2 (CDR2), HVR-H3 (CDR3), HVR-L1 (CDR1), HVR-L2 ("2"), and HVR-L3 (CDR3) sequences of monoclonal antibody 7b6.b12 are respectively provided as SEQ ID NO:89-98 in Table 5.

FIGS. 15 A, B, and C show the raw experimental data for an experiment where the indicated stabilized conformation specific mAbs delayed $A\beta_{1-42}$ aggregation.

DETAILED DESCRIPTION

Figure 1:
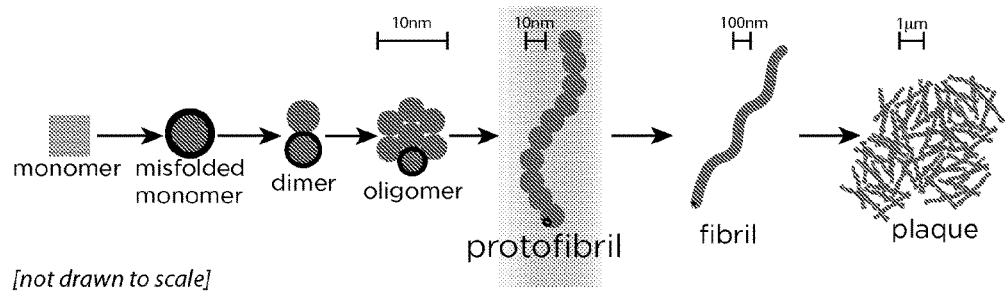
FIG. 1 shows the progressive aggregation of misfolded proteins that leads to fibril formation. The protofibril (sometimes called pre-fibrillar species) is an intermediate on the fibril formation pathway.

In view of the foregoing, it will be seen that the several advantages of the invention are achieved and attained.

Definitions

As used herein, the phrase "Stabilized Conformation-Specific Antibody" or "scsAb" refers to any antibody that binds to an amyloid protofibril but exhibits negligible binding to an amyloid peptide monomer of the amyloid protofibril.

As used herein, the terms "specific binding" or "specifically binding", in the context of an antibody binding to an amyloid protofibril or to a NUCB1-capped amyloid protofibril, refers to binding of an Fab or monovalent portion of that antibody to an antigen (e.g. an amyloid protofibril or a NUCB1-capped amyloid protofibril) with an affinity constant (Kd) of less than about $1\times10^{-6}$ M (molar). In certain embodiments, an antibody that exhibits specific binding to an antigen will have a Kd of less than about $1\times10^{-7}$, $1\times10^{-8}$, $1\times10^{-9}$, or less than about $1\times10^{-1}\cdot$M (molar).

An antibody or fragment, variant, or derivative thereof is said to competitively inhibit binding of a reference antibody or antigen binding fragment thereof to a given epitope if it binds to that epitope and blocks, to some degree, binding of the reference antibody or antigen binding fragment to the epitope. Competitive inhibition can be determined by any method known in the art including, but not limited to, competition ELISA assays. In certain embodiments, an antibody can be said to competitively inhibit binding of the reference antibody to a given epitope if the antibody reduces binding of the reference antibody by at least 90%, at least 80%, at least 70%, at least 60%, or at least 50% when the antibody is provided at equimolar or higher concentration relative to the reference antibody.

As used herein, the phrase "negligible binding", in the context of an antibody binding to an amyloid peptide monomer, refers to binding of an Fab portion of an antibody to an antigen (e.g. amyloid peptide monomer) with an affinity constant of more than about $1\times10^{-5}$.

As used herein, the term "antibody" refers to any of a polyclonal antibody, a monoclonal antibody, humanized antibodies, non-human species specific antibodies, synthetic antibodies, single-chain antibodies, a chimeric antibodies, human antibodies, affinity matured antibodies, bispecific antibodies, as well as fragments of such molecules that comprise at least one complementarity-determining region.

As used herein, the phrase "affinity matured antibody" refers to an antibody comprising one or more alterations in one or more hypervariable regions (HVRs) that provide for an improvement in the affinity of the antibody for an antigen in comparison to an unaltered parent antibody that lacks those alteration(s). Methods for obtaining affinity matured antibodies include, but are not limited to, techniques described in Marks et al. Bio/Technology 10:779-783 (1992), Barbas et al., Proc Nat. Acad. Sci, USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

As used herein, the phrase "amyloid protofibril" refers to any amyloid fibril precursor to an amyloid fibril.

As used herein, the term "prevent", when used in the context of an amyloid disease, refers to any delay in the onset of symptoms associated with a given amyloid disease in comparison to a subject that has not received the agent.

As used herein, the term "treat", when used in the context of an amyloid disease, refers to any delay in the progression of symptoms associated with a given amyloid disease in comparison to a subject that has not received the agent.

As used herein, the phrase "therapeutically effective dose" refers to a dose of an agent that provides for an improvement in either the onset of symptoms or the progression of symptoms associated with a given disease in comparison to a subject that has not received the agent.

As used herein, the phrase "hypervariable region," or "HVR," refer to the regions of an antibody variable domain that exhibit sequence hypervariability and/or that form structurally defined loops. The VH chain of an antibody can typically comprise HVR-H1, HVR-H2, and HVR-H3 regions while the VL chain of an antibody can typically comprise HVR-L1, HVR-L2, and HVR-L3 regions. The phrase "HVR" thus encompasses, but is not limited to, the Kabat Complementarity Determining Regions (CDRs) that are based on sequence variability (Kabat et al., Sequences of Proteins of Immunological Interest, 5th Ed. Public Health Service, National Institutes of Health, Bethesda, Md. (1991)). The phrase "HVR" also encompasses, but is not limited to, regions defined by the location of the structural loops (Chothia and Lesk, J. Mol. Biol. 196:901-917 (1987)).

As used herein, the "Framework" or "FWR" regions (amino acid residues) are variable domain residues that are not HVR residues. The FWR residues include residues that separate the HVR-H1, HVR-H2, and HVR-H3 regions while the VL can typically comprise HVR-L1, HVR-L2, and HVR-L3 regions.

As used herein the phrase "bispecific antibody" refers to a monoclonal antibody that specifically binds at least two different antigens. In the context of the scsAb provided herein, one of the binding specificities is for one or more amyloid protofibrils and the other binding specificity is for any other antigen. Such bispecific scsAb can also be a humanized or human antibody. Methods for obtaining affinity matured antibodies include, but are not limited to, techniques described in WO 93/08829, Traunecker et al., EMBO J., 10: 3655 (1991), WO 94/04690, Hollinger et al., Shalaby et al., J. Exp. Med., 175: 217-225 (1992), Proc. Natl. Acad. Sci. USA, 90:6444-6448 (1993), and Gruber et al., J. Immunol., 152:5368 (1994).

As used herein, the phrase "sNUCB1" refers to any natural or non-naturally occurring form of a NUCB1 protein that is capable of capping an amyloid protofibril.

As used herein, the terms "polypeptide" and "peptide" are interchangeable.

As used herein, the phrase "conservative amino acid substitutions" refers to one or more changes in an amino acid sequence where one or more amino acid(s) are replaced with another amino acid(s), the size, charge, and/or polarity of which is similar to that of the native amino acid. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Conservative amino acid changes can in certain instances be made by substituting one amino acid within one of these groups with another amino acid within the same group.

As used herein, the term "corresponding", when used in the context of comparing, aligning, or identifying equivalent amino acids in one polypeptide sequence with another polypeptide sequence, refers to the comparison or alignment that will yield the highest percent identity when aligned with the other polypeptide sequence.

As used herein, the phrase "non-conservative amino acid substitutions" refers to one or more changes in an amino acid sequence where one or more amino acid(s) are replaced with another amino acid(s), the size, charge, and/or polarity of which is dissimilar to that of the native amino acid. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine. Non-conservative amino acid changes can be made by substituting one amino acid that is within one of these groups with another amino acid within a distinct group.

As used herein, the phrase "operably linked" refers to the joining of nucleic acid sequences or protein sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the desired protein. Nucleic acid sequences that can be operably linked may be, for example, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences). Nucleic acids encoding protein coding regions can also be operably linked via in-frame fusions to other nucleic acids encoding protein coding regions that provide various functions including, but not limited to, sub-cellular targeting, extracellular targeting, stabilization, epitope tags, effector molecules, and the like.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description of the Embodiments

The aggregation of hydrophobic peptides and proteins into amyloid fibrils is a characteristic pathological feature observed in ~30 different "protein-folding" diseases including Alzheimer's disease (AD), Parkinson's disease (PD), and Type 2 diabetes mellitus (DM). Whereas monomeric forms of amyloidogenic peptides/proteins often have necessary biological functions, amyloid fibrils and their prefibrillar aggregates (often called "protofibrils") cause cell toxicity. A schematic diagram of the amyloid fibril formation process is provided in FIG. 1. Characteristics of various amyloid fibril intermediates are compared to NUCB1-capped protofibril antigens in FIG. 2.

Amyloid protofibrils display conformational epitopes such as cross-beta secondary structures that are common to immature amyloid protofibrils, but are not found on native monomer peptides or even on mature fibrils. Because they recognize secondary structure conformations and not primary structure, certain stabilized conformation specific antibodies (scsAb) raised against NUCB1-capped IAPP immunogen recognize other amyloid protofibrils in addition to the NUCB1-capped IAPP immunogen to which they were raised, such as protofibrils derived from Aβ42 or transthyretin (TTR). Evidence suggests that preventing aggregation of pathogenic amyloid peptides might prevent disease progression. The development of effective treatments for amyloid disease has been hampered by a lack of assays and biomarkers to detect amyloid protofibrils.

Provided herein are various methods for obtaining stabilized conformation specific antibodies (scsAb) and antibodies obtained therefrom. In general, these methods comprise exposing an immuno-competent host to an amyloid protofibril that has been capped with a soluble (i.e. mature) NUCB1 protein and isolating antibodies from the host. Also provided herein are methods whereby the antibodies are further characterized as well as methods whereby various synthetic, chimeric, humanized, human, or other versions of the antibodies are prepared.

Amyloid protofibrils capped with NUCB1 can be comprised of any one of a variety of amyloid peptides. Exemplary amyloid peptides include, but are not limited to, Amyloid β23 and Amyloid Aβ42, tau, α-Synuclein, Huntingtin, mutant isoforms of the wt PrP protein, Amylin or hIAPP, β2-microglobulin, Superoxide dismutase, TTR (Transthyretin), Ataxin-3, Gelsolin, Immunoglobulin (Ig) light chain, Serum Amyloid A, Lysozyme, Lactotransferrin, Fibrinogen, Prolactin, insulin, Atrial natriuretic factor, BriL, Cystatin-c, Apolipoprotein A1, and α1-antichymotrypsin. In certain embodiments, the amyloid peptide is selected from the group consisting of hIAPP, β23, and Aβ42. Exemplary methods for obtaining amyloid protofibril that has been capped with a soluble (i.e. mature) NUCB1 protein have been described (10). In brief, methods for obtaining an amyloid protofibril immunogen can comprise: co-incubating an amyloid peptide with a soluble NUCB1 protein under conditions that provide for binding of the NUCB1 protein to an amyloid peptide protofibril comprising the amyloid peptide to obtain a NUCB1-capped amyloid protofibril; and, purifying the NUCB1-capped amyloid protofibril. In certain embodiments, the co-incubation comprises mixing the amyloid peptide with about an equimolar amount of the NUCB1 protein. In certain embodiments, the soluble NUCB1 protein can comprise an N-terminal deletion of about 31 to about 232 N-terminal amino acids of a NUCB1 protein or a mature form of the protein. In certain embodiments where a soluble wild type NUCB1 protein is used, capping of the protofibril is achieved by incubation of the amyloid peptide and NUCB1 protein in a $Ca^{+2}$ free buffer. Various NUCB1 proteins that can be used to cap protofibrils are provided herewith as SEQ ID NO:1-4. However, it is also anticipated that in certain embodiments, NUCB1 variant proteins comprising mutations in the EF-hand domains, or otherwise lacking the EF-hand domains, can be used to cap protofibrils in the presence of calcium. Such "calcium independent" NUCB1 proteins include, but are not limited to, proteins disclosed in WO 2010/009330, which is incorporated herein by reference in its entirety. Conditions for incubating various amyloid peptides with both wild type and calcium independent forms of NUCB1 under conditions that provide for formation of capped protofibrils are also disclosed WO 2010/009330. Exemplary and non-limiting conditions for obtaining NUCB1 capped A1340 or Aβ42 protofibrils can comprise adding soluble NUCB1 to Aβ fibrillization reactions where the Aβ40 or Aβ42 monomers are at concentration of about 32 micromolar to about 150 micromolar in about 20 mM to about 100 mM Tris buffer at about pH 7.3-7.5 at about 25 degrees C., where NUCB1 is at an equimolar or lower concentration to the Aβ40 or Aβ42 monomers. In certain embodiments, the Aβ42 monomers are at concentration of about 32 or 64 micromolar in the fibrillization reaction. Exemplary and non-limiting conditions for obtaining NUCB1 capped hIAPP can comprise adding soluble NUCB1 to hIAPP fibrillization reactions where the hIAPP monomers are at concentration of about 32 micromolar in about 15 mM to about 100 mM Tris buffer at about pH 7.3-7.5 at about 25 degrees C., where NUCB1 is at an equimolar or lower concentration to the hIAPP monomers. In certain embodiments, preformed fibrils comprising any of the aforementioned amyloid peptides may be added to nucleate a fibrillization reaction. In certain embodiments where a calcium independent form of NUCB1 is used to cap the protofibrils, calcium ions may be present at a concentration of up to at least about of 5 mM. Exemplary and non-limiting conditions for capping protofibrils with calcium independent forms of NUCB1 can comprise a pH of at pH 8.0 and 25 degrees C. in a buffer containing 50 mM Tris and 150 mM NaCl.

Purification of the NUCB1-capped protofibril can be accomplished by any method that provides for separation or enrichment of the capped protofibril from the reaction mixture. Depending upon the relative amounts of reactants (i.e. amyloid peptide monomers and NUCB1 protein) used, it is anticipated that NUCB1-capped amyloid protofibrils can be separated from, or substantially enriched over, unreacted NUCB1, amyloid peptide monomers, and uncapped protofibrils present in the reaction mix. Exemplary and non-limiting methods for effecting purification of NUCB1-capped amyloid protofibrils include size-exclusion chromatography, ion-exchange chromatography, hydrophobic interaction chromatography, and combinations thereof. In certain embodiments, purifying can comprise subjecting the coincubated mixture in step (a) to size-exclusion chromatography (SEC) on a fast performance liquid chromatography (FPLC) device and harvesting a fraction comprising the NUCB1-capped amyloid protofibrils.

The scsAb antibodies provided herein can be obtained by using the NUCB1-capped amyloid protofibrils as an immunogen. Monospecific antibodies showing specificity to a conformational epitope of a target of choice can be purified from mammalian antisera containing antibodies reactive against this region, or can be prepared as monoclonal antibodies. Murine monoclonal antibodies can be prepared using the technique of Kohler and Milstein (1975, Nature 256: 495-497). Hybridoma cells are produced by mixing the splenic lymphocytes with an appropriate fusion partner, preferably myeloma cells, under conditions which will allow the formation of stable hybridomas. The splenic antibody producing cells and myeloma cells are fused, selected, and screened for antibody production. Hybridoma cells from antibody positive wells are cloned by a technique such as the soft agar technique of MacPherson (1973, Soft Agar Techniques, in Tissue Culture Methods and Applications, Kruse and Paterson, Eds, Academic Press). Monoclonal antibodies are produced in vivo by injecting respective hydridoma cells into pristine primed mice, collecting ascite fluid after an interval of time, and prepared by techniques well known in the art. Methods for obtaining fully human monoclonal antibodies from transgenic mice that have been engineered to produce specific human antibodies in response to immunization include those disclosed by Green et al., Nature Genet. 7:13, 1994; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N.Y. Acad. Sci. 764:525-35, and US Patent Applic. Pub No. 20120117669, which is specifically incorporated herein by reference in its entirety. To obtain such transgenic mice, elements of the human heavy and light chain locus are introduced into strains of mice derived from embryonic stem cell lines that contain targeted disruptions of the endogenous murine heavy chain and light chain loci (Bruggemann et al., Curr. Opin. Biotechnol. 8:455-58 (1997)). Various dereplication, competition, and/or blocking techniques employing unbound NUCB1 can be used when screening the mAb to identify those desired clones that bind an amyloid protofibril as opposed to those undesired mAb that bind the NUCB1 protein.

The scsAb provided herein can also be obtained by using NUCB1-capped amyloid protofibrils as probes of antibody display libraries comprising one or more recombinant antibodies or fragments thereof. Exemplary and non-limiting antibody display methods that can be used to obtain the scsAb include, but are not limited to, those disclosed in US Pat. Applic. Pub. No. 20090155810 and 20130040861, which are both specifically incorporated herein by reference in their entireties. Additional methods for selection of antibody fragments from libraries using enrichment technologies, including but not limited to phage display, ribosome display (Hanes and Pluckthun, 1997, Proc. Nat. Acad. Sci. 94: 4937-4942), bacterial display (Georgiou, et al., 1997, Nature Biotechnology 15: 29-34) and/or yeast display (Kieke, et al., 1997, Protein Engineering 10: 1303-1310) can be used to select single chain antibodies which specifically bind to target NUCB1-capped amyloid protofibrils. Single-chain antibodies are selected from a library of single chain antibodies produced directly utilizing filamentous phage technology. Applicable phage display technology that can be used to obtain scsAb is disclosed in U.S. Pat. Nos. 5,565,332; 5,733,743; 5,871,907; 5,872,215; 5,885,793; 5,962,255; 6,140,471; 6,225,447; 6,291650; 6,492,160; 6,521,404; 6,544,731; 6,555,313; 6,582,915; 6,593,081, as well as other U.S. family members, or applications which rely on priority filing GB 9206318, filed 24 May 1992; (see also Vaughn, et al. 1996, Nature Biotechnology 14: 309-314). Various de-replication, competition, and/or blocking techniques employing unbound NUCB1 can be used when screening the antibody library to identify those desired clones that bind the amyloid protofibril as opposed to the undesired clones that bind the NUCB1 protein.

The scsAb antibodies provided herein can comprise a whole antibody, an antibody fragment, or an amyloid protofibril binding portion thereof that exhibits binding to amyloid protofibrils. In certain embodiments, the scsAb exhibits specific binding to amyloid protofibrils and/or to amyloid fibrils. In certain embodiments, the scsAb exhibits negligible binding to an amyloid peptide monomer of the amyloid protofibril. In certain embodiments, the scsAb can be a sequence-independent scsAB that exhibits binding to two or more distinct amyloid protofibrils where each distinct protofibril is comprised of distinct amyloid peptide monomers. In certain embodiments, the scsAb will exhibit binding to an amyloid protofibril that is distinct from the NUCB1-capped amyloid protofibril used to immunize a host or to screen a library, where each distinct amyloid protofibril is comprised of distinct amyloid peptide monomers. In non-limiting and exemplary embodiments, a NUCB1-capped hIAPP protofibril can be used to immunize a host or to screen a library and then select an antibody that specifically binds one or more amyloid protofibrils and/or amyloid fibrils comprising amyloid peptides selected from the group consisting of hIAPP, Aβ42, and β23. In certain embodiments, a scsAb can exhibit binding to one or more protofibrils selected from the group consisting of an hIAPP, Aβ42, and a β23 protofibril. ELISA, RIA, or other immunoassay analyses can be used to determine which mAbs are sequence-independent and conformation-dependent scsAb depending on their reactivity to amyloid fibrils, prefibrillar oligomers (i.e. protofibrils), or amyloid peptide monomers.

The scsAb provided herein include, but not be limited to, any specific binding member, immunoglobulin class and/or isotype (e.g., IgG.sub.1, IgG.sub.2, IgG.sub.3, IgG.sub.4, IgM, IgA, IgD, IgE and IgM); and biologically relevant fragment or specific binding member thereof, including but not limited to Fab, F(ab')2, Fv, and scFv (single chain or related entity). In certain embodiments, an scsAb will be a glycoprotein comprising at least two heavy (H) chains and two light (L) chains inter-connected by disulfide bonds, or an antigen binding portion thereof. In certain embodiments, an scsAb heavy chain is comprised of a heavy chain variable region (VH) and a heavy chain constant region (CH1, CH2 and CH3). In certain embodiments, an scsAb light chain is comprised of a light chain variable region (VL) and a light chain constant region (CL). In certain embodiments, variable regions of both the scsAb heavy and light chains can comprise framework regions (FWR) and hypervariable regions (HVR). In certain embodiments, the four FWR regions are relatively conserved while HVR regions (HVR1, HVR2 and HVR3) represent hypervariable complementarity determining regions and are arranged from NH.sub.2 terminus to the COOH terminus as follows: FWR1, HVR1, FWR2, HVR2, FWR3, HVR3, FWR4. Thus, a light chain variable region can comprise FWR1, HVR-L1, FWR2, HVR-L2, FWR3, HVR-L33, FWR4 in certain embodiments. Similarly, a heavy chain variable region can comprise FWR1, HVR-H1, FWR2, HVR-H2, FWR3, HVR-H3, FWR4 in certain embodiments. In certain embodiments, the variable regions of the scsAb heavy and light chains contain a binding domain that specifically binds a conformational or other epitope present in an amyloid protofibril while, depending of the isotype, the constant region(s) may mediate the binding of the immunoglobulin to host tissues or factors. The scsAb provided herein can also comprise a chimeric antibody, humanized antibodies, a recombinant antibody, a human antibody, an affinity matured antibody, a bispecific antibody, or a fragments thereof. The scsAb can be derived from natural sources, or they may be partly or wholly synthetically produced. The scsAb fragments provided herein can comprise a binding domain such as Fab, scFv, Fv, dAb, Fd, or diabodies, that recognizes a conformational or other epitope of an amyloid protofibril. Such scsAb fragments thus include, but are not limited to, (i) a Fab fragment (i.e. a monovalent fragment consisting of the VL, VH, CL and CH domains); (ii) a F(ab')2 fragment (i.e. a bivalent fragment comprising two Fab fragments linked by a disulfide bridge at the hinge region); (iii) a Fd fragment consisting of the VH and CH domains; (iv) a Fv fragment consisting of the VL and VH domains of a single arm of an antibody (v) a dAb fragment, which comprises a VH domain; (vi) a hypervariable region (HVR) or one, two, or three HVR regions joined by framework regions; (vii) a scAb, an antibody fragment containing VH and VL as well as either CL or CH; and (viii) artificial antibodies based upon protein scaffolds, including but not limited to fibronectin type III polypeptide antibodies (U.S. Pat. No. 6,703,199 and PCT International Application Publication No. WO 02/32925). Furthermore, although the two domains of the scsAb Fv fragment, VL and VH, are typically coded for by separate genes, they can also be joined, using recombinant methods, by a synthetic linker that enables them to be made as a single protein chain in which the VL and VH regions pair to form monovalent molecules (known as single chain Fv (scFv)).

In certain embodiments, the scsAb can be a "chimeric antibody" that is a monoclonal antibody constructed from the variable regions derived from the immunized host, and constant regions derived from the intended treatment subject source (for a review, see Morrison and 01, 1989, Advances in Immunology, 44: 65-92). Non-limiting examples of immunized hosts include rodents, goats, pigs, non-human primates and the like. Non-limiting examples of treatment subjects can include humans, horses, cows, pigs, dogs, and cats. An exemplary and non-limiting embodiment is a chimeric antibody wherein a heavy and light DNA sequences (e.g. SEQ ID NO: 39, 49, 59, 69, 79, and 89 for heavy chain and SEQ ID NO: 41, 51, 61, 71, 81, and 91 for light chain), from the rodent (e.g., mouse) antibody are operably linked with constant regions of a human antibody and cloned into a mammalian expression vector. Non-limiting examples of treatment subjects can include humans, horses, cows, pigs, Dogs, and cats. A light and heavy chain chimeric antibody expression vectors can be cotransfected into a recipient cell line and selected for expression of the chimeric polypeptides and expanded. This cell line can be cultured to produce both the light chain and heavy chain of a chimeric antibody.

Also provided herein are "humanized" versions of any murine monoclonal scsAb obtained by the methods provided herein or otherwise disclosed herein. Humanization of the murine monoclonal scsAb comprises replacing at least some of amino acid residues in constant regions which differ from those in the corresponding human constant region sequences by site directed mutagenesis of individual residues and/or by grafting of entire complementarity determining regions. Humanization of mAb sequences has been described (Jones et al., 1986, Nature 321: 522-526; Riechmann et al. (1988) Nature 332:323-327). Humanization of murine monoclonal scsAb can also be achieved by methods including, but not limited to, "reshaping" (see Verhoeyen, et al., 1988, Science 239: 1534-1536), "hyperchimerization" (see Queen, et al., 1991, Proc. Natl. Acad. Sci. 88:2869-2873) or "veneering" (Mark, et al., 1994, Derivation of Therapeutically Active Humanized and Veneered anti-CD18 Antibodies Metcalf end Dalton, eds. Cellular Adhesion Molecular Definition to Therapeutic Potential. New York: Plenum Press, 291-312). In certain embodiments, sequence comparisons between rodent and human sequences can be used to identify specific amino acid substitutions from a rodent to a human consensus that will preserve antigen binding while reducing immunogenicity. Methods for constructing a humanized antibody through use of sequence comparisons include, but are not limited to techniques disclosed by Sims et al. (1993) J. Immunol. 151:2296; Chothia et al. (1987) J. Mol. Biol. 196:901; Carter et al. (1992) Proc. Natl. Acad. Sci. USA, 89:4285; and Presta et al. (1993) J. Immunol., 151:2623. In certain embodiments, the antigen binding sites from both the light and heavy chain are effectively removed from the scsAb rodent expressing antibody clone and sub-cloned (or "grafted") into an expression vector coding for the framework region of the human antibody. A non-limiting and exemplary embodiment of a humanized scsAb antibody may be expressed wherein the hypervariable regions HVR-L1, HVR-L2, and HVR-L3 regions of the variable light chain region are set forth in SEQ ID NOs: 46-48, 56-58, 66-68, 76-78, 86-88, and 96-98, and the hypervariable regions HVR-H1, HVR-H2, and HVR-H3 regions of the variable heavy chain region are set forth in SEQ ID NOS: 43-45, 53-55, 63-65, 73-75, 83-85, and 93-95, all provided in Table 5. In certain embodiments, a "humanized antibody" provided herein is effectively an antibody constructed with only murine HVRs from a murine monoclonal scsAb, with the remainder of the variable region where the constant region is derived from a human source.

Fully human scsAb monoclonal antibodies are also provided herein. Such methods include, but are not limited to, in vitro immunization of human B-cells with NucB1-capped amyloid protofibrils, fusion of spleen cells from NucB1-capped amyloid protofibril immunized transgenic mice carrying inserted human immunoglobulin genes, isolation from human immunoglobulin V region phage libraries probed with NucB1-capped amyloid protofibrils, or similar modifications of other procedures as known in the art or provided herein wherein a NucB1-capped amyloid protofibril is used as an antigen or an immunogen. Exemplary phage display techniques are disclosed in US Pat. Applic. Pub. No. 20090155810, which is specifically incorporated herein by reference in its entirety.

The scsAb provided herein that exhibit specific binding to amyloid protofibrils can thus comprise any of the VL or VH regions provided herein. A summary of the VL and VH sequences is provided in Table 1.

TABLE 1

VL and VH Sequences of exemplary scsAb.

| Chain | Relative Protofibril binding activity[1] | mAb Source | SEQ ID NO:[2] |
|---|---|---|---|
| VH | Aβ42 > hIAPP > β43 | 5a8.b11 | 40 |
| VH | hIAPP > Aβ42 > β43 | 4a8.e11 | 50 |
| VH | hIAPP > Aβ42 > β43 | 4b1.h9 | 60 |
| VH | β43 > Aβ42 > hIAPP | 3f2.e10 | 70 |
| VH | β43 > hIAPP > Aβ42 | 5c9.a2 | 80 |
| VH | β43 > hIAPP > Aβ42 | 7b6.b12 | 90 |
| VL | Aβ42 > hIAPP > β43 | 5a8.b11 | 42 |
| VL | hIAPP > Aβ42 > β43 | 4a8.e11 | 52 |
| VL | hIAPP > Aβ42 > β43 | 4b1.h9 | 62 |
| VL | β43 > Aβ42 > hIAPP | 3f2.e10 | 72 |
| VL | β43 > hIAPP > Aβ42 | 5c9.a2 | 82 |
| VL | β43 > hIAPP > Aβ42 | 7b6.b12 | 92 |

Figure 5:
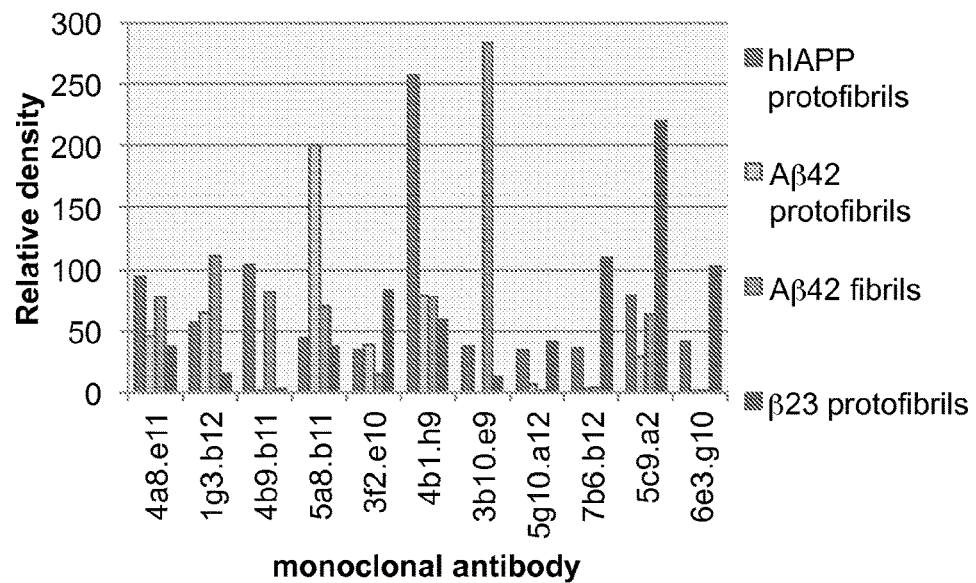
FIG. 5 shows a bar graph of the quantified density from dot blot analysis of the antigenic reactivity of eleven selected conformation-specific, sequence-independent mAbs. For each indicated mAb on the X-axis, immunoreactivity is shown against hIAPP protofibrils (leftmost column in each group of four columns), Aβ42 protofibrils (column second from left in each group of four columns), Aβ42 fibrils (column second from right in each group of four columns), and β23 protofibrils (rightmost column in each group of four columns).
Figure 8:
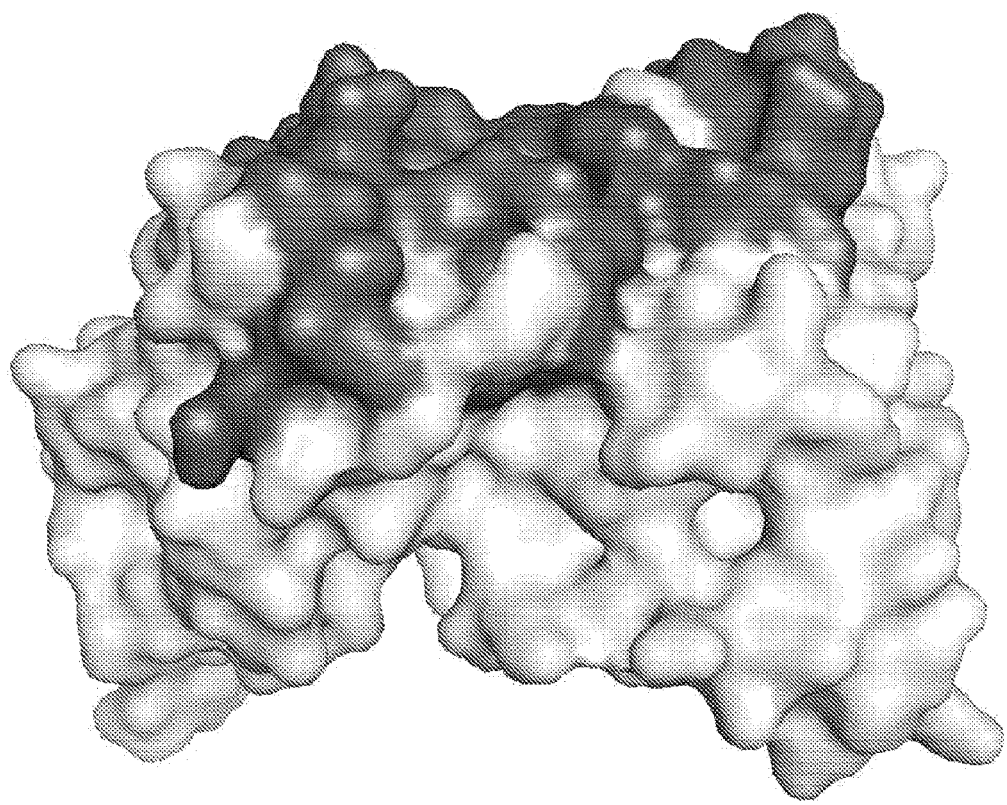
FIG. 8 shows a model of the Fv fragment (heavy and light chains) of the scs mAb 5a8.b11. Variable regions of the Fv fragment are shown in dark grey and the constant regions are shown in white.

[1]From FIG. 5 for intact mAb from the indicated source comprising both the VH and VL of that source.
[2]Table 5

TABLE 2

HVR-L and HVR-H Sequences of exemplary scsAb.

| HVR Region | mAb Source | SEQ ID NO:[1] |
|---|---|---|
| HVR-L1 | 5a8.b11 | 46 |
| HVR-L2 | 5a8.b11 | residues 18 to 20 of SEQ ID NO: 47 |
| HVR-L3 | 5a8.b11 | 48 |
| HVR-H1 | 5a8.b11 | 43 |
| HVR-H2 | 5a8.b11 | 44 |
| HVR-H3 | 5a8.b11 | 45 |
| HVR-L1 | 4a8.e11 | 56 |
| HVR-L2 | 4a8.e11 | residues 18 to 20 of SEQ ID NO: 57 |
| HVR-L3 | 4a8.e11 | 58 |
| HVR-H1 | 4a8.e11 | 53 |
| HVR-H2 | 4a8.e11 | 54 |
| HVR-H3 | 4a8.e11 | 55 |
| HVR-L1 | 4b1.h9 | 66 |
| HVR-L2 | 4b1.h9 | residues 18 to 20 of SEQ ID NO: 67 |
| HVR-L3 | 4b1.h9 | 68 |
| HVR-H1 | 4b1.h9 | 63 |
| HVR-H2 | 4b1.h9 | 64 |
| HVR-H3 | 4b1.h9 | 65 |
| HVR-L1 | 3f2.e10 | 76 |
| HVR-L2 | 3f2.e10 | residues 18 to 20 of SEQ ID NO: 77 |
| HVR-L3 | 3f2.e10 | 78 |
| HVR-H1 | 3f2.e10 | 73 |
| HVR-H2 | 3f2.e10 | 74 |
| HVR-H3 | 3f2.e10 | 75 |
| HVR-L1 | 5c9.a2 | 86 |
| HVR-L2 | 5c9.a2 | residues 18 to 20 of SEQ ID NO: 87 |
| HVR-L3 | 5c9.a2 | 88 |
| HVR-H1 | 5c9.a2 | 83 |
| HVR-H2 | 5c9.a2 | 84 |
| HVR-H3 | 5c9.a2 | 85 |
| HVR-L1 | 7b6.b12 | 96 |
| HVR-L2 | 7b6.b12 | residues 18 to 20 of SEQ ID NO: 97 |
| HVR-L3 | 7b6.b12 | 98 |
| HVR-H1 | 7b6.b12 | 93 |
| HVR-H2 | 7b6.b12 | 94 |
| HVR-H3 | 7b6.b12 | 95 |

[1]Table 5

Any of the amino acid sequences provided in Table 1 or Table 2 can thus be used in methods described herein and in other patent applications to obtain scsAb that exhibit specific binding to amyloid protofibrils. Also provided herein are amino acid sequence variants of the sequences provided in Table 1 or 2 wherein one, two, three or more amino acid residues are substituted with a conserved amino acid. In certain embodiments, generalized methods for constructing or otherwise obtaining antibodies that are disclosed in US Patent Application Publication Numbers 20130046078, 20130030159, and 20120219557, each of which is incorporated herein by reference in their entireties, are used in combination with the sequences provided herein in Table 1, Table 2, or elsewhere to construct a scsAb.

The scsAb provided herein can be used as agents for inhibiting amyloidogenesis. The scsAb provided herein can also be used in pharmaceutical preparations and methods for treating the amyloidogenic diseases where amyloid fibrils would otherwise accumulate. Such intermediate oligomers and protofibrils have been shown to cause cytotoxicity.

Isolated nucleic acids that encode the scsAb are also provided herein. Isolated nucleic acids that encode scsAb can further comprise an operably linked nucleic acid that encodes a signal peptide that provides for secretion in a host cell. Such signal peptides are typically selected based on their ability to support secretion in a selected host cell. Operable linkage of the nucleic acid encoding the scsAb with signal peptides that provide for secretion of the scsAb in mammalian, insect, yeast, or bacterial cells is thus provided. Isolated nucleic acids that encode scsAb can also further comprise an operably linked nucleic acid that encodes an epitope tag or effector molecule. In certain embodiments, both a light chain and a heavy chain of any scsAb provided herein can be expressed in a cell. Co expression of the heavy chain and light chain of the scsAb can be achieved with recombinant nucleic acids where nucleic acid sequences encoding each chain are operably linked to distinct promoter sequences. Co expression of the heavy chain and light chain of the scsAb can also be achieved with recombinant nucleic acids where nucleic acid sequences encoding each chain are operably linked to a single promoter sequence. In certain embodiments where the nucleic acid sequences encoding each chain are operably linked to a single promoter sequence, the heavy and light chain sequences can yield a single chain antibody. In other embodiments where the nucleic acid sequences encoding each chain are operably linked to a single promoter sequence, an internal ribosome entry site (IRES) can be operably linked to the coding region that is proximal to the 3' end of the transcription unit that encodes the two chains. In other embodiments where the nucleic acid sequences encoding each chain are operably linked to a single promoter sequence, a prtoteoltyic cleavage site can be operably linked between the coding regions for the two chains.

Isolated nucleic acids provided herein also comprise a variety of distinct nucleic acid sequences that encode scsAb due to the degeneracy of the genetic code. Such nucleic acids can be derived either by mutagenesis of naturally occurring NUCB1 nucleic acid sequences or by de novo synthesis. Embodiments where the codons of the isolated nucleic acid are changed to reflect the A+T content of a host organism are also provided herein.

The invention also provides cells that comprise nucleic acids that encode scsAb. It is understood that this terms refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation techniques. As used herein, the terms "transformation" includes any method whereby an exogenous nucleic acid is introduced into a cell. Transformation methods thus include, but are not limited to, calcium phosphate or calcium chloride co-precipitation, DEAE-dextran-mediated transfection, lipofection, particle mediated delivery, or electroporation.

To obtain transformed cells, a gene that encodes a selectable marker is generally introduced into the host cells along with the gene of interest. For prokaryotic cells, selectable markers include, but are not limited to, genes that confer resistance to antibiotics, genes that confer the ability to grow in the absence of otherwise required nutrients and the like. For eukaryotic cells, selectable markers that confer resistance to drugs including, but not limited to, G418, hygromycin, zeocin and methotrexate can be used.

Further provided are vectors comprising any of the nucleic acids encoding scsAb provided herein or host cells engineered to express those nucleic acids. In specific embodiments, the vectors comprise a nucleotide sequence which regulates the expression of the protein encoded by the nucleic acid of the invention. For example, the nucleotide sequence encoding the protein of the invention can be operably linked to an inducible promoter.

Host cells comprising the nucleic acids and vectors of the invention are also provided. In certain embodiments, the vector or nucleic acid is integrated into the host cell genome; in other embodiments, the vector or nucleic acid is extra-chromosomal. A host cell can be a mammalian cell, a yeast cell, and insect cell or a bacterial cell. The bacterial host cell can be an *E. coli* cell.

The recombinant expression vectors of the invention can comprise a nucleotide sequence encoding a scsAb in a form suitable for expression in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, ribosome binding sites, transcriptional terminators, and other expression control elements (e.g., polyadenylation signals). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of scsAb desired, etc. The expression vectors of the invention can be introduced into host cells to thereby produce scsAb encoded by nucleic acids as described herein.

In practicing any of the above referenced methods involving administration of the scsAb to a subject, a variety of pharmaceutical or veterinary compositions comprising these active agents can be administered by a variety of techniques. Such pharmaceutical or veterinary compositions may be formulated in various ways known in the art for administration purposes. To prepare the pharmaceutical or veterinary scsAb compositions, an effective amount of the scsAb as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, by intrathecal injection, targeted organ injection, intranasally or by inhalation). Representative examples of pharmaceutically acceptable carriers and delivery vehicles include, but are not limited to, saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween™, Pluronics™, or PEG. The pharmacologic compositions described herein may further be prepared in unitary dosage form suitable for administration orally, percutaneously, by parenteral injection (including subcutaneous, intramuscular, intravenous and intradermal), by intrathecal injection, targeted organ injection, topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

Supplementary active compounds can also be incorporated into the pharmaceutical or veterinary compositions disclosed herein. Compositions, formulations, and methods of delivering protein therapeutics to subjects are described by Pawar et al., Expert Opin Biol Ther. August 4(8):1203-12, 2004, which is incorporated herein by reference in its entirety.

Given that certain amyloid based diseases are associated with certain organs, it is further contemplated that pharmaceutical compositions for use in treating those diseases will be tailored to use in the affected organs. Embodiments for treatment of amyloidosis of the brain associated with amyloid beta fibrils will comprise pharmaceutically acceptable carriers and formulations suited for delivery to the brains of subjects suffering from such disease. In certain embodiments, the scsAb will be combined with a polymer. This polymer can provide for sustained and/or controlled release of the scsAb. Polymers suitable for delivery of scsAb to the brain and other organs include, but are not limited to, alginates, chitosan, collagen, fibrins, methoxy poly(ethylene glycol), polyanhydrides, poly(e-caprolactone), poly(ethylene oxide), poly(lactic acid), poly-lactide-co-glycolide (PLGA), poly(ortho esters), polyethylene vinyl-co-acetate (EVAc), polyethylene glycol (PEG), polyester-PEG triblock copolymers, polyphosphazenes, poly[(sebacic-co-(ricinoleic acid)], ricinoleic acid, silicone, and combinations thereof. Formulation of polymers with pharmaceutically active proteins into microspheres and three-dimensional implants that are suitable for delivery of pharmaceutically active polymers to the Central Nervous System is described by Whittlesey and Shea in Exp Neurol. 190:1-16, 2004, which is hereby incorporated by reference in its entirety. Descriptions of polymeric formulations appropriate for delivery of pharmaceutically active agents, including peptides and proteins, to various organs is also described by in Chitkara Macromol Biosci. 8; 6(12):977-90, 2006, which is hereby incorporated by reference in its entirety. Therapeutically effective amounts of a pharmaceutical composition comprising the scsAb can be administered by parenteral injection, by injection into an organ, implantation of a pump, stereotactic delivery, implantation of a cannula, implantation of a three-dimensional implant, or implantation of microspheres.

Methods of using the scsAb to detect or diagnose the predisposition, presence, and/or progression of amyloid disease in a subject are also provided herein. Such methods of detection or diagnosis can be used to identify pre-disease states, clinical pathological diagnosis, and post-mortem diagnoses of an amyloid disease. The scsAb and related methods can also be used to monitor progress of amyloid disease before, during, and/or after therapeutic intervention to evaluate treatment efficacy. In general, a decrease in scsAb immunoreactive material in comparison to material from a control is correlated with a decrease in predisposition, presence, and/or progression of amyloid disease in a subject. An increase in scsAb immunoreactive material in comparison to material from a control is correlated with a decrease in predisposition, presence, and/or progression of amyloid disease in a subject. In this context, a control can be any or all of a reference sample(s) taken from a subject or subjects that do not have an amyloid disease, a reference sample(s) taken from a subject or subjects that have an amyloid disease, and/or a sample taken from a subject at any point in time. Useful control or reference samples from a subject can include, but not limited to, samples taken before, during, or after therapeutic intervention. Diseases that are detectable or diagnosable with scsAb provided herein are listed in Table 3. In certain embodiments, an exemplary scsAb selected from the group consisting of 4a8.e11, 5a8.b11, 4b1.h9, 5c9.a2, 3f2.e10, 5g10.a12, and 1g3.b12 is used to detect or diagnose the predisposition, presence, and/or progression of Amyloid β42 and/or Alzheimer's disease. In certain embodiments, an exemplary scsAb selected from the group consisting of 4a8.e11, 5a8.b11, 4b1.h9, 5c9.a2, 3f2.e10, 5g10.a12, 4b9.b11, 3b10.e9, 7b6.b12, 1g3.b12, and 6e3.g10 is used to detect or diagnose the predisposition, presence, and/or progression of hIAPP and/or Type 2 Diabetes Mellitus associated amyloid disease.

In certain embodiments, detection or diagnosis can be achieved by introducing an unlabeled or suitably labelled scsAb into a subject and detecting amyloid protofibrils therein. Labeling of scsAb with imageable agents is provided herein. As used herein, an imageable agent can comprise any composition that can be attached to an antibody that provides for direct visualization, an electromagnetic signal, a radioactive signal and/or a signal detectable by magnetic resonance imaging, positron emission tomography or computerized axial tomography. Such imageable agents used to label scsAb include, but not limited to, gadolinium, indium-Ill, iodine-123, iodine 124, iodine-125, iodine 131, carbon-11, fluorine-18, copper-64 and technetium-99 and fluorophores such as rhodamine, fluorochromes (e.g., NIR fluorochromes such as Cy5™, Cy5.5™, Cy7™ or Licor NIR™, Alexa Fluor® 680, Alexa Fluor® 700, Alexa Fluor® 750, IRDye38™, IRDye78™, IRDyeδO™, indocyanine green, LaJolla Blue™, and Licor NIR™ is provided herein. Methods for in vivo imaging of antigens in subjects that can be adapted for use with the scsAb include, but are not limited to methods, disclosed in US20120253160 or US20110311448. Kits comprising such scsAb and optionally other reagents, instructions, or other materials useful for performing such "in vivo" or "in vitro" detection or diagnosis of amyloid disease are also provided.

In certain embodiments, detection or diagnosis can be achieved by subjecting a sample obtained from a subject to any assay that uses a scsAb to detect amyloid protofibrils. Such samples can comprise tissue and/or fluids obtained from the subject. Tissue samples used in such assays include, but are not limited to, tissue samples obtained from the brain, nervous system, liver, heart, lung, and the like. Fluid samples used in such assays include, but are not limited to, blood, plasma, interstitial fluid, cerebrospinal fluid, urine, and the like. Any method of immunodetection may be used to detect scsAb amyloid protofibrils in the sample. Such assays can comprise use of a labelled or unlabeled scsAb. Labelled scsAb used include, but are not limited to, scsAb labelled with enzymes, radioactive isotopes, fluorogenic reporters, electrochemiluminescent reporters, DNA reporters, and the like. Unlabelled scsAb can be used in immunodection assays based on surface plasmon resonance, electrode resistance, or other measurements. The immunodetection method can be any of: (i) a completive homogenous immunoassay; (ii) a one site non-competitive immunoassay; or, (iii) a two site non-competitive immunoassay.

Also provided herein are NUCB1-capped amyloid protofibrils, NUCB1-capped amyloid protofibrils that are covalently or non-covalently linked to a detectable label, and their use in detecting the presence of antibodies that specifically bind to amyloid protofibrils. In certain embodiments, the presence of such anti-amyloid protofibril antibodies in a subject or subject sample is diagnostic for amyloid disease predisposition, presence, and/or progression. The presence of amyloid beta fibril-reactive IgGs and amyloid beta conformer-reactive IgGs that exhibit minimal binding to amyloid beta monomers in donor plasma samples has been shown (O'Nuallain et al., J Clin Immunol. 2010 May; 30 Suppl 1:S37-42; O'Nuallain et al., Biochemistry. 2008 Nov. 25; 47(47):12254-6). In certain embodiments, detectable labels linked to NUCB1-capped amyloid protofibrils can comprise an imageable agent. Labeling of NUCB1-capped amyloid protofibrils with imageable agents is provided herein. These imageable agents can comprise any composition that can be attached to an NUCB1-capped amyloid protofibril that provides for direct visualization, an electromagnetic signal, a radioactive signal and/or a signal detectable by magnetic resonance imaging, positron emission tomography or computerized axial tomography. Such imageable agents used to label NUCB1-capped amyloid protofibrils include, but not limited to, gadolinium, indium-Ill, iodine-123, iodine 124, iodine-125, iodine 131, carbon-11, fluorine-18, copper-64 and technetium-99 and fluorophores such as rhodamine, fluorochromes (e.g., NIR fluorochromes such as Cy5™, Cy5.5™, Cy7™ or Licor NIR™, Alexa Fluor® 680, Alexa Fluor® 700, Alexa Fluor® 750, IRDye38™, IRDye78™, IRDyeδO™, indocyanine green, LaJolla Blue™, and Licor NIR™. Methods for in vivo imaging of antigens in subjects that can be adapted for use with the NUCB1-capped amyloid protofibrils include, but are not limited to methods, disclosed in Agdeppa and Spilker, AAPS J. June 2009; 11(2): 286-299; and US Patent Application Public. Nos. US20040223909 and US20070189967. Kits comprising such NUCB1-capped amyloid protofibril and optionally other reagents, instructions, or other materials useful for performing such "in vivo" or "in vitro" detection or diagnosis of amyloid disease are also provided.

Methods of treating subjects afflicted by amyloidosis with pharmaceutical or veterinary compositions comprising the scsAb are also provided herein.

The use of scsAb in treatment of certain specific amyloid associated diseases is provided. In one embodiment, the use of scsAb to treat type 2 diabetes associated with accumulation of amylin fibrils is provided. Such treatments would comprise administration of therapeutically effective amount of a scsAb to a subject suffering from amylin fibril-mediated type 2 diabetes. In certain embodiments, treatment of type 2 diabetes is effected preferably targeting delivery of scsAb to the pancreas or regions within the pancreas with accumulations of amylin fibrils.

In other embodiments, the use of scsAb to treat Alzheimer's disease, dementia, memory loss or other manifestations of CNS disease associated with accumulation of amyloid beta 42 (Aβ42) fibrils and/or amyloid beta 40 fibrils in the CNS is provided. In certain embodiments, such treatments would comprise administration of therapeutically effective amount of a scsAb to a subject suffering from amyloid beta 42 (Aβ42) fibril related neurological disorders comprising Alzheimer's disease, dementia, memory loss, and the like. In certain embodiments, it is anticipated that a scsAb would be delivered directly to the CNS by injection. In still other embodiments, a scsAb would be delivered directly to certain regions of the CNS by stereotactic techniques.

In addition to methods of treatments that provide for slowing the progression of Alzheimer's disease in afflicted subjects, the scsAb can be used in methods whereby Alzheimer's disease symptoms are at least partially reversed. In certain embodiments, the methods can comprise treatments that result in a reduction in the severity of disease. Such reductions in disease severity can be measured according to a clinical scale. Clinical scales used to establish reductions in disease severity include, but are not limited to, the Global Deterioration Scale (Reisberg et al., Am J Psychiatry. 1982 September; 139(9):1136-9), the Clinical Dementia Rating, the Functional Assessment Staging procedure, and the like (Reisberg et al., Int Psychogeriatr. 2007 Jun.; 19(3):421-56).

In certain embodiments, the scsAb provided herein are used to treat or mitigate the effects of an amyloid disease selected from the group consisting of Familial Amyloid Cardiomyopathy (FAC), Familial Amyloid Polyneuropathy (FAP), non-V30M Familial Amyloid Polyneuropathy (FAP), Central and Nervous System Selective Amyloidosis (CNSA). In the Familial Amyloidosis diseases FAP (Polyneuropathy) and FAC (cardiomyopathy), data supports a mechanism of amyloid formation whereby genetically dominant mutant TTR tetramers are less stable and dissociate into monomers which then undergo a conformational re-arrangement and re-assembly into fibrils at moderately acidic pH. The TTR gene is located on human chromosome 18q12.1 and spans 4 exons and 5 introns (also murine chromosome 18). There are 304 Single Nucleotide Polymorphisms (SNPs) identified in human populations and 80 confirmed pathogenic that lead to the clinical phenotype of TTR amyloidosis with the most prevalent being V122I, T60A and V30M (most common). Other mutations associated with TTR amyloidosis include, but are not limited to, the L111M, A25T and D18G mutations in TTR. These mutations are numbered according to the residue number in the mature TTR protein (SEQ ID NO: 101) or other allelic variants thereof. Studies have shown that the V30M mutation pre-disposes to FAP and other mutations such as V 122I favor the development of FAC. The drug Tafamidis™ is approved (ex USA) to treat FAP and Phase 3 trials in FAC are ongoing. Rather than targeting amyloid directly it stabilizes the tetrameric form of TTR, preventing the amyloidogenic TTR monomers from forming (Bulawa et al. Proc Natl Acad Sci USA. 2012 Jun. 12; 109(24):9629-34; Ruberg F L and Berk J L. Circulation. 2012; 124:1286-1300; Scott L J. Drugs. 2014 Jul. 15; Merlini et al., Cardiovasc Transl Res. 2013 Dec.; 6(6):1011-20. doi: 10.1007/s12265-013-9512-x). In certain embodiments, such treatments would comprise administration of therapeutically effective amount of a scsAb to a subject suffering from an amyloid disease selected from the group consisting of Familial Amyloid Cardiomyopathy (FAC), Familial Amyloid Polyneuropathy (FAP), non-V30M Familial Amyloid Polyneuropathy (FAP), Central and Nervous System Selective Amyloidosis (CNSA). Antibodies provided herein that can be used in such treatments include, but are not limited to, an antibody that binds the same epitope as a 5c9.a2 reference monoclonal antibody, an antibody that competitively inhibits binding of a 5c9.a2 reference monoclonal antibody to an amyloid protofibril, an antibody that competitively inhibits binding of a 5c9.a2 reference monoclonal antibody to a NUCB1-capped amyloid protofibril, and an antibody comprising a variable heavy chain region (VH) comprising the HVR-H1, HVR-H2, and HVR-H3 sequences of SEQ ID NO: 83, 84, and 85, respectively, and a variable light chain region (VL) comprising the HVR-L1, HVR-L2, and HVR-L3 sequences of SEQ ID NO:86, residues 18 to 20 Of SEQ ID NO: 87, and SEQ ID NO: 88, respectively. Any of the aforementioned antibodies or other antibodies used can also comprise at least one of any of the aforementioned HVR H1, HVRH2, HVR H3, HVR L1, HVR L2, and/or HVR L3 sequences wherein one, two, or three amino acids are substituted with a different amino acid. In certain embodiments, these amino acid substitutions in at least one of the HVR H1, HVRH2, HVR H3, HVR L1, HVR L2, and/or HVR L3 sequences are conservative amino acid substitutions Depending on the type and severity of the amyloid disease, about 1 microgram/kg to 100 mg/kg of each scsAb is an initial candidate dosage for administration to the subject, whether, for example, by one or more separate administrations, or by continuous infusion. In certain embodiments, a daily dosage can range from about 1 microgram/kg to about 100 mg/kg or more. For repeated administrations over several days or longer, depending on the condition, the treatment is sustained until the amyloid disease is treated, as measured by the methods described above.

A list of the amyloid disease of humans that can be treated with a scsAb or with nucleic acids encoding the scsAb is provided below. These amyloid diseases can also be detected or diagnosed by the use of scsAb and related methods provided herein. In certain embodiments, a scsAb that was raised against, or that recognizes, an amyloid protofibril comprising the amyloid peptide involved in the amyloid disease is used to detect, diagnose, or treat the amyloid disease. In certain embodiments, a scsAb that recognizes more than one amyloid protofibril is used to detect, diagnose, or treat the amyloid disease. Thus, a scsAb that was raised against an amyloid protofibril comprising an amyloid peptide other than the amyloid peptide involved in the disease can be used to detect, diagnose, or treat the amyloid disease in certain embodiments when that scsAb recognizes both the amyloid protofibril that it was raised against and a distinct amyloid peptide protofibril. In certain embodiments, an exemplary scsAb selected from the group consisting of 4a8.e11, 5a8.b11, 4b1.h9, 5c9.a2, 3f2.e10, 5g10.a12, and 1g3.b12 is used to treat Alzheimer's disease. In certain embodiments, an exemplary scsAb selected from the group consisting of 4a8.e11, 5a8.b11, 4b1.h9, 5c9.a2, 3f2.e10, 5g10.a12, 4b9.b11, 3b10.e9, 7b6.b12, 1g3.b12, and 6e3.g10 is used to treat Type 2 Diabetes Mellitus associated amyloid disease.

TABLE 3

Amyloid associated diseases that are detectable, diagnosable, or treatable with scsAb.

| Disease | Amyloid peptide Monomer(s) Involved | Clinical Feature | GenBank Accession (protein) |
|---|---|---|---|
| Alzheimer's | Amyloid β and tau | Progressive dementia | Tau: S66627 APP: P05067 |
| Parkinson's | α-Synuclein | Movement Disorder | AAS83394 |
| Huntington's | Huntingtin | Dementia, motor and psychiatric problems | P42858 |
| Prion Diseases | Mutant isoforms of the wt PrP protein | dementia, ataxia, insomnia, paraplegia, paresthesias, and deviant behavior. | AAB35416 |
| Type 2 Diabetes Mellitus | Amylin or hIAPP | Amyloid deposits if amylin causing loss of Islet of Langerhans | P10997 |
| Dialysis-related amyloidosis (DRA) | $β_2$-microglobulin | Numbness or tingling associated with muscle weakness, in fingers and hands | NP_004039 |
| Amyotrophic lateral sclerosis | Superoxide dismutase | Movement Disorder | P00441 |
| Pick's Disease | tau | Atrophy of the frontal and temporal lobes of the brain | AAI14949 |

TABLE 3-continued

Amyloid associated diseases that are detectable, diagnosable, or treatable with scsAb.

| Disease | Amyloid peptide Monomer(s) Involved | Clinical Feature | GenBank Accession (protein) |
|---|---|---|---|
| Senile systemic amyloidosis | TTR (Transthyretin) | Peripheral Neuropathy | NP_000362 (SEQ ID NO: 100) |
| Familial Amyloid Cardiomyopathy (FAC) | V122I mutant of mature TTR | Cardiomyopathy | |
| Familial Amyloid Polyneuropathy (FAP) | V30M mutant of mature TTR (Transthyretin) | Peripheral Neuropathy | |
| Non-V30M Familial Amyloid Polyneuropathy (FAP) | Mutant TTR (Transthyretin) | Peripheral Neuropathy +/1 cardiomyopathy | |
| Central Nervous System Selective Amyloidoses (CNSA) | Highly destabilized A25T and D18G mutants of mature TTR (Transthyretin) | Central Nervous System disorders | |
| Machado-Joseph Disease | Ataxin-3 | Lack of muscle control | NP_001019802 |
| Gelsolin Amyloid Disease | Gelsolin | Severe ataxia with neuropathy | NP_000168 |
| Primary systemic amyloidosis | Immunoglobulin (Ig) light chain | Cutaneous findings as evidence of underlying plasma cell dyserasia | CAA6153 CAA6155 CAA6157 |
| Secondary systemic amyloidosis | Serum Amyloid A | Chronic inflammatory condition like rheumatoid | NP_000322 |
| Familial non-neuropathic amyloidosis | Lysozyme | Arthritis, sarcoidosis, crohn's disease etc | CAA32175 |
| Familial subepithelial corneal amyloid | Lactotransferrin | Severe photophobia, tearing and an ocular foreign body sensation | NP_002334 |
| Hereditary renal amyloidosis | Fibrinogen | Sicca syndrome and renal disease | NP_000499 |
| Pituitary-gland amyloidosis | Prolactin | Mass arising from the pituitary gland with suprasellar extension | NP_000939 |
| Injection-localized amyloidosis | insulin | Histological analysis of the injection sites demonstrated foreign body type granulomas surround areas of amyloidogenesis | AAN39451 |
| Atrial amyloidosis | Atrial natriuretic factor | Isolated atrial Amyloid deposits, highly prevalent in elderly people with long-standing congestive heart failure | NP_006163 |
| Familial British dementia | BriL | Autosomal dominant condition characterized by dementia, progressive spastic tetraparesis and cerebellar ataxis | NP_001020466 |
| Hereditary cerebral amyloid angiopathy | Cystatin-c | Repeated hemorrhages leading to paralysis | CAA36497 CAA43856 |

TABLE 3-continued

Amyloid associated diseases that are detectable, diagnosable, or treatable with scsAb.

| Disease | Amyloid peptide Monomer(s) Involved | Clinical Feature | GenBank Accession (protein) |
|---|---|---|---|
| Familial amyloid polyneuropathy III | Apolipoprotein A1 | Peripheral polyneuropathies including multiple cranial nerves, corneal dystrophy and skin changes | NP_000030 |
| Chronic obstructive pulmonary disease | α1-antichymotrypsin | Cough, sputum production | NP_001076 |

Amyloidosis in various non-human animals can be treated with veterinary compositions comprising a scsAb, or nucleic acids encoding the same. These amyloid diseases that occur in non-human animals can also be detected or diagnosed by the use of scsAb and related methods provided herein. Veterinary amyloidoses including but not limited to those of the hepatic or renal system can be treated with the veterinary compositions of the invention. Veterinary amyloidoses including but not limited to those resulting of formation of serum amyloid A fibrils or AA fibrils can be treated with the veterinary compositions of the invention. It is further anticipated that veterinary subjects including but not limited to non-human primates, cattle, pigs, horses, goats, sheep, and companion animals such as cats and dogs suffering from amyloidosis can be treated with the veterinary compositions comprising scsAb. The use of scsAb that comprise constant light and constant heavy chain regions patterned after the constant light and constant heavy chain regions of endogenous antibodies of the subject to be treated is also provided. In certain embodiments, such scsAb would thus comprise constant light and constant heavy chain regions patterned after those of cattle, pigs, horses, goats, sheep, and companion animals such as cats and dogs.

Pharmaceutical compositions comprising nucleic acids that encode the scsAb of the invention are also provided. In certain embodiments, such nucleic acids would comprise lentiviral vectors that could be introduced into the brains or other afflicted organs of subjects suffering from amyloidosis. Delivery of potentially therapeutic proteins to the brains of afflicted subjects has been described (J Neurosis. 2003 Mar. 15; 23(6):1992-6).

In certain embodiments provided herein, the kits comprising a pharmaceutical or veterinary composition with a therapeutically effective amount of a scsAb and a pharmaceutically acceptable carrier as well as one or more containers are provided. Also provided are kits comprising a labelled or unlabeled scsAb and optionally one or more reagents that are useful for detecting and/or diagnosing an amyloid disease.

The composition(s) of the kit may be provided as a liquid solution or as a dried powder. In certain embodiments, the composition(s) are provided in a liquid solution. The liquid solution that can be an aqueous solution. When the composition(s) provided is (are) a dry powder, the powder can be reconstituted by the addition of a suitable solvent that may also be provided.

The container will generally include a vial into which the pharmaceutical or veterinary composition or a labelled or unlabeled scsAb may be placed, and preferably suitably aliquot TED. The kits of the present invention will also typically include a means for containing the recombinant protein, recombinant vector and/or cells in a container in close confinement for commercial sale. Such containers may include injection or blow-molded plastic containers into which the desired vials are retained.

The kit can also comprise a device or a component of a device for performing the therapeutic, detection, or diagnostic methods provided herein. Devices, or components of devices, include, but are not limited to, syringes and other implements useful for delivery of the composition to the blood stream, a specific organ, or the CNS. In certain embodiments useful for detection or diagnosis of amyloid disease, such components could comprise any type of solid matrix wherein a scsAb is covalently or non-covalently coupled. Such solid matrices to which scsAb are coupled include, but are not limited to, microtiter plates, beads, microfluidic devices, and the like. In certain embodiments, the compositions of the invention can be provided in unit dose form. In addition or in the alternative, the kits of the invention can provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration. Instructions can also be provided as a fixed, fully detachable, or partially detachable label that is associated with one or more containers in the kit. The instructions associated with the kit can provide directions for preparing the pharmaceutical or veterinary composition for administration and/or instructions for administration of the pharmaceutical or veterinary composition to a subject in need thereof. The instructions associated with the kit can provide directions for detecting or diagnosing amyloid disease in a subject.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1. Stabilization of Amyloid Protofibrils by NUCB1

Figure 3:
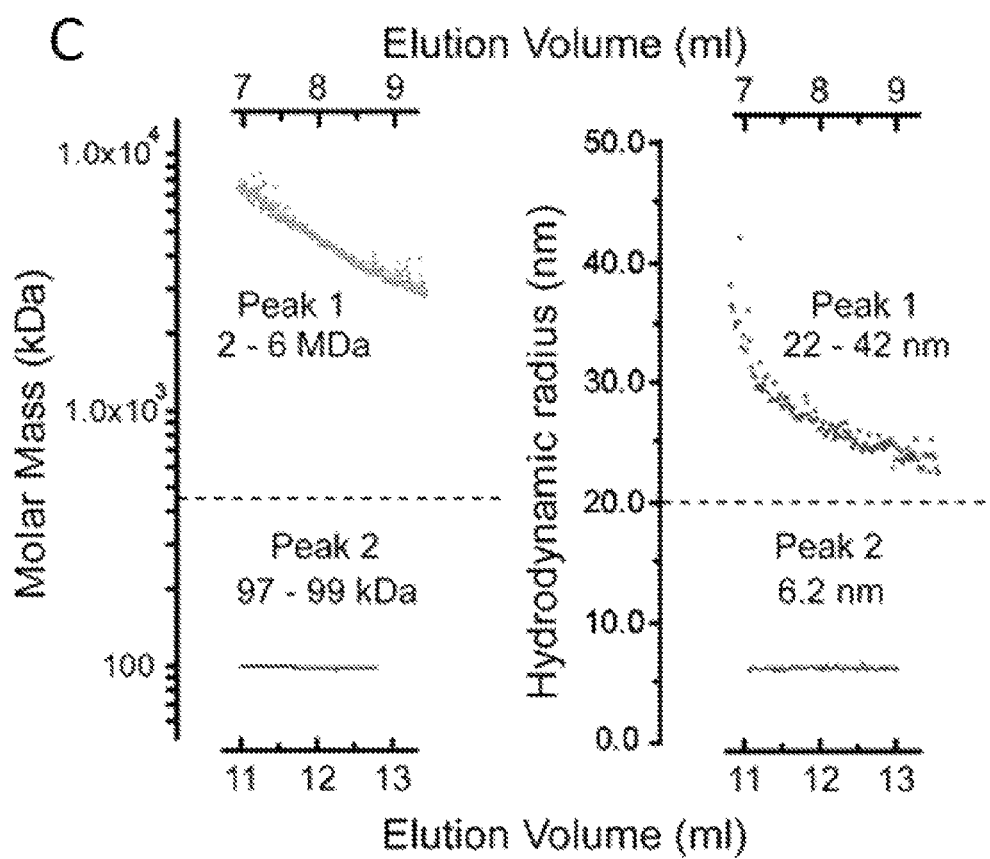
FIGS. 3A, B, C, D, E, and F show the isolation and purification of stable NUCB1-capped hIAPP protofibrils. (A) SEC was used to analyze the products of the 1:1 mixture of hIAPP and NUCB1. NUCB1 alone elutes at 12 ml (dotted curve) while the sample from 1:1 reaction mixture removed after 60 min gives an additional peak, Peak 1, eluting at 7.8 ml (solid curve). (B) Dot blot assay shows that NUCB1 is present in both peaks, hIAPP is only present in the Peak 1 fraction. (C) MALS analysis (left) of Peak 1 estimates the molecular mass in the range of 2-6 million Da and DLS (right) predicts hydrodynamic radii in the range of 22-42 nm. MALS and DLS analysis of Peak 2 predicts a molecular mass and hydrodynamic radii characteristic for a dimer of NUCB1. (D) TEM analysis of the Peak 1 fraction shows the presence of prefibrillar species. Inset: TEM image of fibrils alone. (E) AFM images show that sNUCB1 stabilized hIAPP prefibrillar species with the height of prefibrillar species varying from 1.0 to 2.0 nm. (F) AFM images show that sNUCB1(S44C)-[Nano-Au] caps the ends of prefibrillar species of hIAPP. Nano-Au clusters was confirmed by increase in height of the ends of these prefibrillar species.

Despite that observation that amyloid oligomers and protofibrils are believed to be the key culprits in amyloid-induced cell toxicity, the isolation and stabilization of these intermediates along the pathway of fibril formation has been a challenge. We have determined that NUCB1 offers a novel strategy to stabilize protofibrillar species of hIAPP (FIG. 3) (10). Using size-exclusion chromatography (SEC) on a fast performance liquid chromatography (FPLC) instrument, we were able to isolate a mixture of NUCB1-capped hIAPP protofibrils, which we characterized using a number of biophysical and imaging methods (FIG. 3) (10). NUCB1 and hIAPP were incubated together and then subjected to SEC. The SEC chromatogram shows two peaks, one at 7.6 ml (Peak 1) and another at 11.8 ml (Peak 2). Injection of a solution of NUCB1 alone onto the column generates a peak centered at 11.8 ml. Since hIAPP contains only one Tyr and no Trp residues, NUCB1 dominates the absorbance at 280 nm. Dot blot analysis shows that NUCB1 was present in both the Peak 1 and Peak 2 fractions, whereas hIAPP was present only in the Peak 1 fraction (FIG. 3B).

Multi-angle light scattering (MALS) and dynamic light scattering (DLS) analysis were used to estimate the average molecular mass and hydrodynamic radii of the eluting species (FIG. 3C). MALS analysis of Peak 1 gives an estimated molecular mass in the range of 2-6 million Da, while the DLS analysis yields hydrodynamic radii of 22-42 nm. The data suggest that NUCB1 binds to and stabilizes a high-molecular-mass prefibrillar hIAPP species. Analysis of Peak 2 shows a 97- to 99-kDa molecular mass species with a hydrodynamic radius of 6.2 nm, consistent with the value observed for a dimer of NUCB1.

Mechanistically, NUCB1 binds to and stabilizes a prefibrillar intermediate along hIAPP aggregation pathway by "capping" the ends of the growing protofibrils. Transmission electron microscopy (TEM) analysis of the Peak 1 fraction shows the presence of oligomeric and protofibrillar species (FIG. 3D). Atomic force microscopy (AFM) images show that NUCB1-stabilized hIAPP prefibrillar species have a height varying from 1.0 to 2.0 nm (FIG. 3E). TEM analysis shows the presence of electron dense prefibrillar species with Nano-Au labeled NUCB1(S44C) (FIG. 3F). AFM images show that NUCB1(S44C)-[Nano-Au] caps the ends of prefibrillar species of hIAPP.

Example 2. Immunization of Mice with NUCB1-Capped hIAPP Protofibrils and Recovery of scsAb To develop stabilized conformation-specific (scsAb) mAbs, purified NUCB1-capped hIAPP protofibrils from peak 1 were isolated with SEC and used as antigen in an immunization and myeloma fusion protocol (FIG. 4). These NUCB1-capped hIAPP protofibrils are stable for weeks and thus represent a novel antigen for conformation-specific mAb development. We used in-house low throughput dot-blot immunoreactivity screen to find clones that generically react with a collection of protofibril or fibril species. As hypothesized, it appears that several of the mAbs react with hIAPP, while others react with fibrils that originate from other amyloidogenic peptides, including Aβ42 and an artificial aggregating protein named β23. Aβ42 is the peptide that constitutes the amyloid plaques characteristic of Alzheimer's disease. We have so far identified eleven mAb-producing myeloma clones. The mAbs from 4 clones (4a8.e11, 5a8.b11, 4b1.h9, and 5c9.a2) detect protofibrils of hIAPP, Aβ42 and β23 as well as fibrils of Aβ42. Two clones (3f2.e10 and 5g10.a12) detect only protofibrils of hIAPP, Aβ42 and β23 while two of the clones (7b6.b12 and 6e3.g10) can detect protofibrils of only of hIAPP and β23. The mAbs from two clones (4b9.b11 and 3b10.e9) detect protofibrils of hIAPP and fibrils of Aβ42, and one clone (1g3.b12) can detect protofibrils of hIAPP and Aβ42 and fibrils of Aβ42. These data indicate that we have been successful in isolating conformation-specific, but sequence-independent mAbs using NUCB1-capped protofibrils.

Example 3. Staining of Human Brain Sections with scsAb

The scsAb mAb 5a8.b11, which exhibits preferential binding to Aβ42 protofibrils (FIG. 5), was used to stain human brain samples from subjects with familial Alzheimer's disease. Controls include tissue from normal subjects, a commercial antibody that reacts with anti-Aβ42 fibrils, a no antibody control, and another scsAb (mAb 3b10.e9) that reacts with hIAPP protofibrils but not with Aβ42 protofibrils (FIG. 5).

The staining results obtained with scsAb mAb 5a8.b11 can be distinguished from the control anti-Aβ42 antibody was a gift from Jan Näslund by way of Annica Rönnbäck at the Karolinska Institute, Sweden. This difference in the staining patterns because the new mAb is presumed to stain protofibrils and not fibrils. The scsAb mAb 5a8.b11 exhibits an intracellular staining pattern is very specific and does not stain the extracellular materials like the commercial anti-Aβ42 fibril antibody.

Example 4. Sequencing of the Variable Regions of the scsAb

To obtain sequences of the mAb heavy and light chains, mRNA was isolated from each hybridoma, and cDNA was synthesized using standard reverse transcriptase reaction protocols. All primers were as described by Tiller et al. J, Immunol Methods. 2009 Oct. 31; 350 (1-2):183-93. Primer sequences are provided as SEQ ID NO:5-38 in Table 5. First and the nested second PCRs were performed and separated on agarose gels. Bands were excised and cloned using the TOPO-Blunt™ kit (Invitrogen, Carlsbad, Calif., USA). Sequencing was performed using an M13-R sequencing primer.

Modeling of 5A8.B11 was performed using the "automated prediction of antibody structure" software on the world wide web (internet) site "biocomputing.it/pigs" (Marcatili et al., Bioinformatics (2008) 24 (17): 1953-1954) and using the "web antibody modeling" software on the http internet site "antibody.bath.ac.uk/". Structures were compared and the visualization was edited using MacPyMOL.

Example 5. Characterization of Stabilized Conformation-Specific, Sequence Independent mAbs The specificity of each candidate monoclonal Ab will be examined by ELISA, dot blot, and Western blot analysis of monomeric, prefibrillar oligomeric and fibrillar forms of hIAPP, Aβ42, the artificial β23 peptide, and other types of amyloid materials. ELISA analysis will indicate which mAbs are sequence-independent and conformation-dependent scsAb depending on their reactivity to fibrils, prefibrillar oligomers (i.e. protofibrils), or amyloid peptide monomers. Dot blot analysis will be used to confirm the antibody specificity. Western blot analysis will assess the reactivity of each mAb to low molecular weight oligomers.

Example 6. Determining Potential mAb Effects on-Pathway Aggregation Kinetics To determine if the sequence-independent and conformation-dependent mAbs have an effect on aggregation kinetics, we will use transmission electron microscopy (TEM) as a direct probe of amyloid fibril formation. In our experience, hIAPP alone aggregates within 7 min to form oligomers, which continue to grow and form higher-order intermediates, protofibrils, and protofilaments, which can be observed as early as about 13 min. The protofibrillar intermediates assemble and extend into mature amyloid fibrils within 60 min. Reaction mixtures with stoichiometric or lower concentrations of mAbs will be pre-incubated with hIAPP and analyzed using TEM. Samples will be withdrawn at 7 min and 13 min from reaction mixtures that contain varying amounts of mAb. These analyses will provide information about mAb effect on aggregation of hIAPP. For real-time aggregation kinetics, we will employ a conventional thioflavin-T fluorescence-binding assay. Aggregation of hIAPP alone starts with a nucleation phase of approximately 5 min under the conditions of our assay and extends into a growth/elongation phase between 5 and 20 min. The growth phase of the curve plateaus into a stationary phase where fibrils are in equilibrium with the soluble peptide. mAbs will be added to the assay and we will monitor changes in the kinetics of thioflavin-T fluorescence enhancement. These data will provide insight into the effect mAbs have on aggregation kinetics.

Example 7. Therapeutic Applications of the Conformation-Specific mAbs to Models of Amyloid Disease It is predicted that stabilized conformation-specific mAbs provided herein or obtained by methods provided herein can protect cells from toxic protofibrils/fibrils. Characterized scsAb will be used in cell-culture models of amyloidogenic diseases to screen for protective characteristics. This work can utilize multiple cell models in different ways. In models of T2DM, hIAPP will be applied to the rat insulinoma beta cell line, RIN5fm, in the presence of conformation-specific or control mAbs (10). In each model, cytotoxicity will be measured using standard methods to monitor the health of the cell, such as TUNEL staining to monitor nicked-ends in DNA, MTT assays to monitor mitochondrial health, and lactate dehydrogenase release assays to monitor membrane health. These studies are expected to yield information regarding the protective effects of monoclonal stabilized conformation-specific antibodies in models of aggregation disease. For the model of AD, rat neuronal PC12 cell line will be used. Aβ42 fibrils will be applied extracellularly in the presence of conformation-specific or control mAbs. Similarly, α-synuclein will be applied to SH-SY5Y cells in the presence of conformation-specific or control mAbs (9).

Previously discovered fibril-specific, conformation-dependent mAbs have been shown to detect amyloid deposits in pancreatic tissues of a mouse model of diabetes. In future work, using tissue sections from a similar mouse model, we will test whether the scsAb provided herein can detect islet amyloid deposits. We will also carry out tests to determine whether the scsAb raised against the capped hIAPP protofibrils can detect the presence of hIAPP protofibrils in serum samples and might therefore be used to validate hIAPP as a biomarker for T2DM progression.

Example 8. Inhibition of Fibril Formation

The kinetics of fibril formation in the absence or presence of antibodies was determined using a continuous Thioflavin T (ThT) assay. Recombinant $A\beta_{1-42}$ was isolated by size exclusion chromatography (SEC) in 20 mM sodium phosphate, 0.2 mM EDTA, pH 7.5. Buffer, 26 μM $rA\beta_{1-42}$ peptides alone, or 26 μM $rA\beta_{1-42}$ peptides and 65 nM antibodies were incubated in a 96-well black fluorescence plate in the presence of 10 μM ThT at 37° C., and shaken at 700 r.p.m. using a plate shaker. For the antibody containing samples, either a control anti-rhodopsin 1D4 antibody (Abcam, Inc. Cambridge, Mass., USA) or the test monoclonal antibodies 4A8.E11, 4B1.H9, 3F2.E10, 5A8.B11, 5C9.A2, or 7B6.B12 were used. Measurements were made at 5 minute intervals using a Flexstation™ II microplate reader (Molecular Devices, Sunnyvale, Calif., USA) with excitation and emission at 440 and 480 nm, respectively. Each experimental point is the mean of the fluorescence signal of five wells containing aliquots of the same solution. Raw experimental data is shown in FIG. 15.

The $T_{50}$ (time in minutes for 50% inhibition of fibril formation) was calculated using a sigmoidal 4-parameter curve fit with the following equation:

$$y = y_0 + a/1 + e^{-(x-x_0/b)}$$

TABLE 4

$T_{50}$ (time in minutes for 50% inhibition of fibril formation)

| | $T_{50}$ |
|---|---|
| Abeta alone | 23.8 |
| Abeta + control 1D4 | 25.9 |
| Abeta + 4A8.E11 | 37.9 |
| Abeta + 4B1.H9 | 60.7 |
| Abeta + 3F2.E10 | 42.6 |
| Abeta + 5A8.B11 | 40.3 |
| Abeta + 5C9.A2 | 43.2 |
| Abeta + 7B6.B12 | 40.2 |

Figure 16:
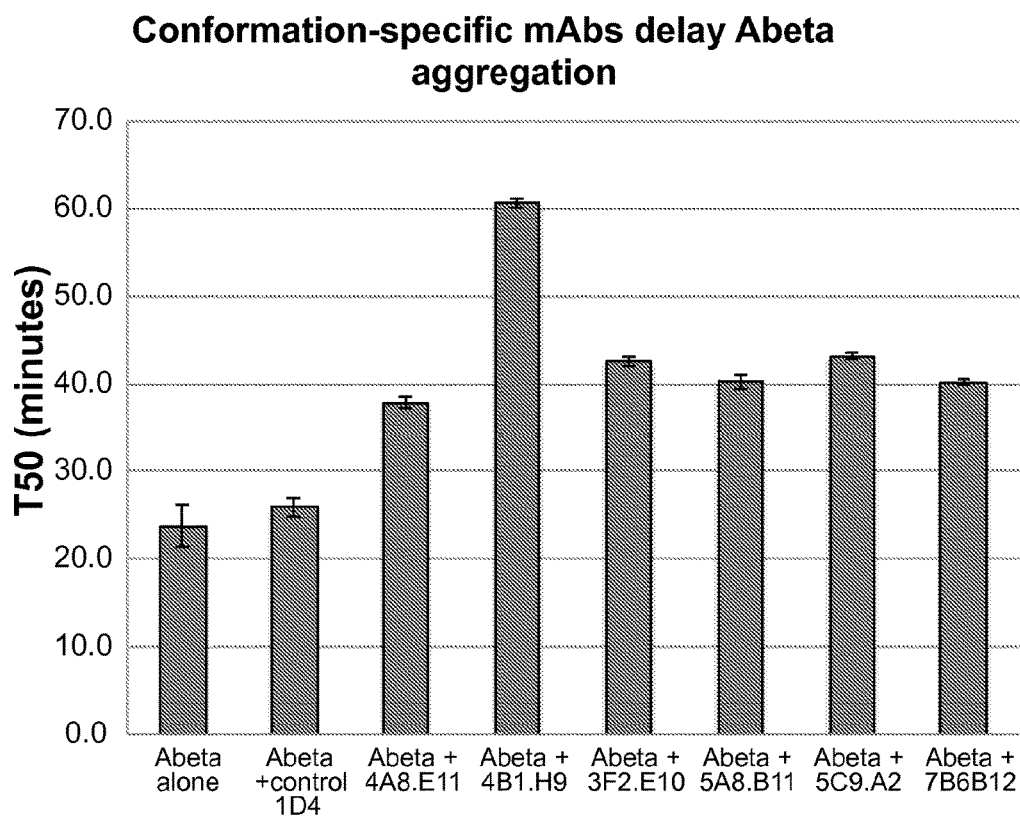
FIG. 16 shows a bar graph comparison the $T_{50}$ values for various control and test mAbs in the $A\beta_{1-42}$ aggregation assay.

A bar chart showing a comparison of the $T_{50}$ values of Table 4 is provided in FIG. 16. All of the stabilized conformation-specific mAbs (4A8.E11, 4B1.H9, 3F2.E10, 5A8.B11, 5C9.A2, or 7B6.B12) provided a significantly improved inhibition of fibril formation relative to the control anti-rhodopsin antibody 1D4. The most pronounced inhibition was observed for mAb 4B1.H9.

Figure 17:
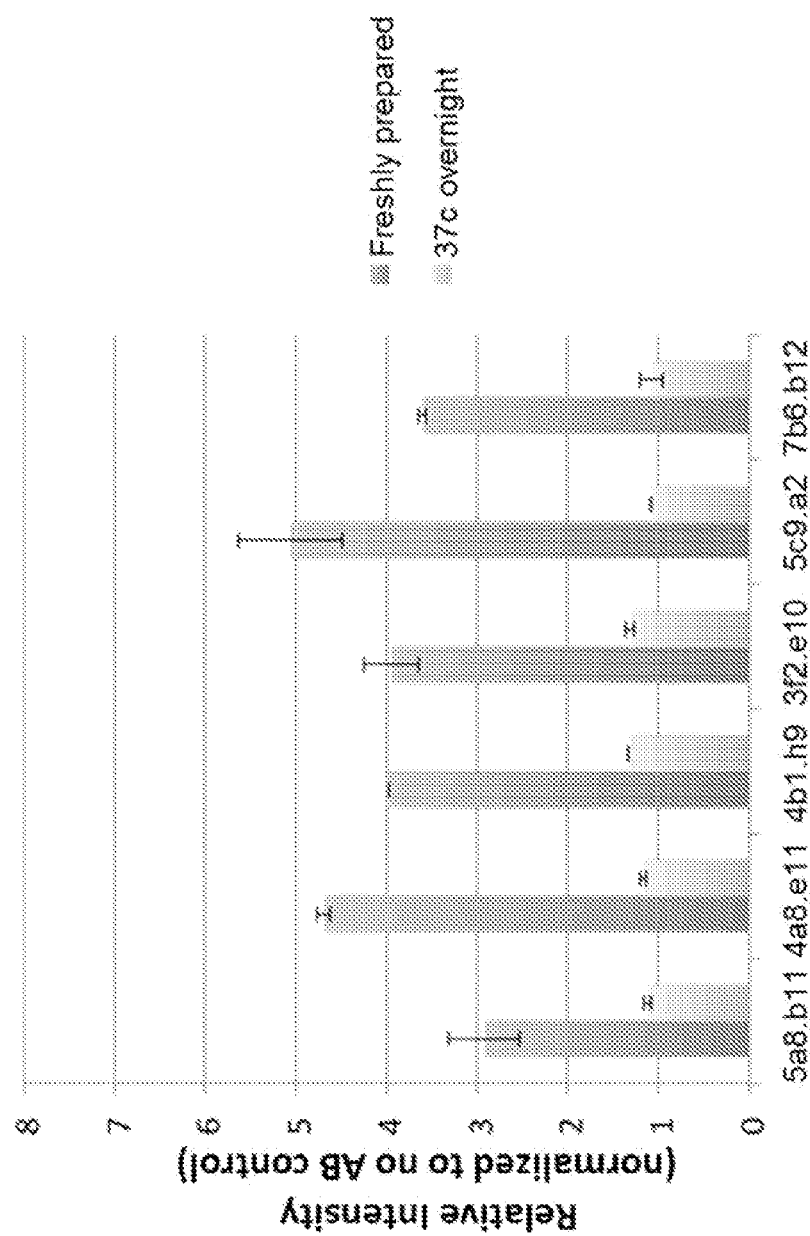
FIG. 17 shows a bar graph comparison of the relative binding of the indicated scsAb for both the freshly prepared Aβ42 preparations at 10 μM that were enriched for protofibrils and monomers (left-most bar for each indicated scsAb) or for a 37° C. overnight Aβ42 preparations at 10 μM that were enriched for fibrils (right-most bar for each indicated scsAb).

Example 9. Preferential Binding of scsAb to Freshly Prepared Aβ42 (Containing Protofibrils) Versus Fibril Preparations Sandwich ELISAs were performed on Aβ42 samples either freshly prepared or incubated with shaking overnight at 37° C. to enrich for monomers and protofibrils or fibrils, respectively. ScsAbs were used to coat Nunc Maxisorp™ plates followed by blocking overnight with 2% BSA. Aβ42 samples were then applied to the wells at either 10 μM or 0 μM concentrations. After washing, remaining Aβ42 was detected with Biosource cat#44-3449 rb-pAb anti-Beta Amyloid 42-biotin and the tertiary antibody was GE cat# NA934V anti rb IgG-HRP. ELISAs were then developed using Amplex Ultrared™ (Invitrogen, Carlsbad, Calif.). The data are normalized to the 0 μM Aβ42 negative control. The bar graph of FIG. 17 shows that all of the scsAb exhibit preferential binding of the freshly prepared Aβ42 samples that are enriched for monomers and protofibrils in comparison to the binding observed in the 37° C. overnight samples that are enriched for fibrils.

Example 10. Kinetic Experiments

The amyloid-β Aβ(M1-42) peptide (MDAEFRHDS-GYEVHHQKLVFFAEDVGSNKGAIIGLMVGGVVIA; SEQ ID NO: 99) was expressed in *Escherichia coli* and purified. Urea-solubilized inclusion bodies were diluted in 10 mM Tris/HCl pH 8.0 containing 1 mm EDTA (buffer A), added to DEAE-cellulose equilibrated in buffer A, and gently agitated for 20 min. The slurry was then centrifuged at 1000 rpm for 10 minutes and the supernatant was extracted. Subsequently, the resin was washed with buffer A containing 25 mM NaCl, followed by elution using buffer A containing 125 mM NaCl. Eluates were centrifuged through a 30 kDa molecular mass cut-off filter and concentrated by centrifugation through a 3 kDa molecular mass cut-off filter. Identical 1 ml aliquots were lyophilized and frozen at −20C.

For kinetic experiments, aliquots of the purified Aβ42 were resuspended in 6M guanidinium hydrochloride and subjected to gel filtration on a Superdex Peptide column in 20 mM sodium phosphate buffer, pH 8, with 200 µM EDTA. The monomer-containing peak was then lyophilized and subjected to a second round of resuspension in 6M guanidinium hydrochloride and gel filtration on a Superdex Peptide column in 20 mM sodium phosphate buffer, pH 8, with 200 µM EDTA. The latter part of the monomer peak was collected on ice and was typically found to have a concentration 30-50 µM. The monomer generated in this way was diluted to 6.604 and supplemented with 10 µM thioflavin T (ThT) from a 1 mM stock and then pipetted into multiple wells of a 96-well half-area plate of black polystyrene with a clear bottom and PEG coating (Corning 3881), 50 µL per well. Fluorescence measurements were made at regular intervals using FlexStation III (Molecular Devices) with excitation and emission at 440 and 480 nm, respectively. Each experimental point is the mean of the fluorescence signal of 6 wells containing aliquots of the same solution.

The sample mixtures (25 µL) were spotted onto a nitrocellulose membrane and allowed to dry at room temperature. After being blocked with 5% milk and TBST (TBS containing 0.05% tween-20) for 1 h at room temperature, the membrane was probed with anti-Aβ (6E10, 1:1000) or scsAbs (1:500) in TBST for 1 h at room temperature. The membranes were washed in TBST 3 times for 5 minutes each, followed by probing with a secondary anti-mouse IgG-HRP (1:10,000) in 5% milk TBST. The membranes were incubated with chemiluminescent substrate (Thermo Scientific) and exposed to HyBlot CL autoradiography film (Denville Scientific, Inc.). ImageJ (available on the internet at rsbweb.nih.gov/ij/index.html) was used to quantify the intensities of the dots.

Figure 18:
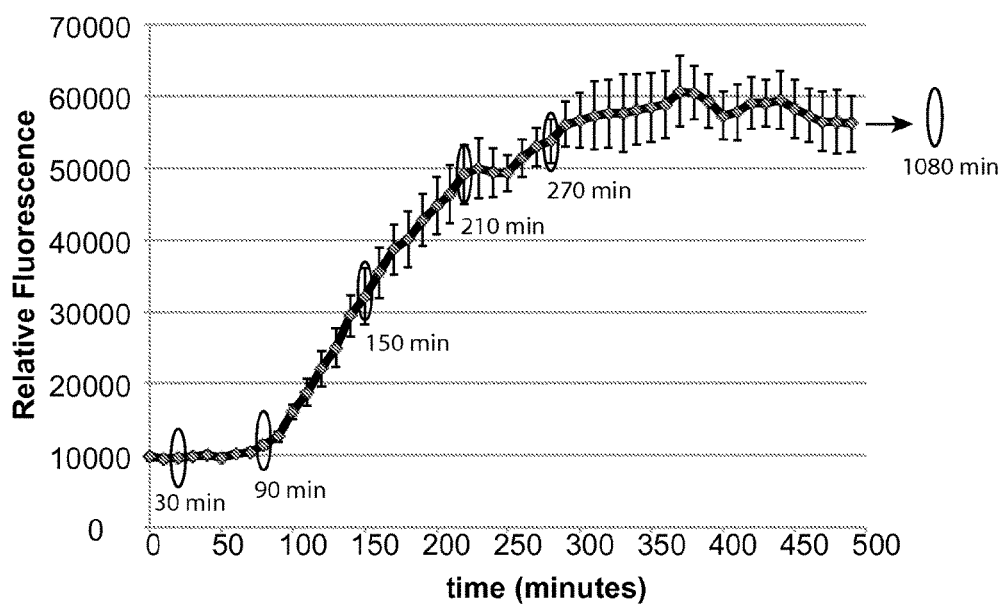
FIGS. 18A, B, C, D, and E show that scsAbs 4a8.e11, 3f2.e10, and 7b6.b12 detect $A\beta_{1-42}$ protofibrils. (A) $A\beta_{1-42}$ aggregation in a thioflavin T fluorescence assay guided sample collection (red circles) for a dot blot assay. (B) Samples from these time points were spotted on PVDF membranes and blotted with an anti-Aβ mAb to detect total $A\beta_{1-42}$, or with 4a8.e11, 3f2.e10, or 7b6.b12. (C) Bar graph showing quantitation of 4a8.e11 reactive material at indicated timepoints. (D) Bar graph showing quantitation of 3f2.e10 reactive material at indicated timepoints. (E) Bar graph showing quantitation of 7b6.b12 reactive material at indicated timepoints. The spots were quantified with ImageJ and normalized to total $A\beta_{1-42}$.
Figure 18:
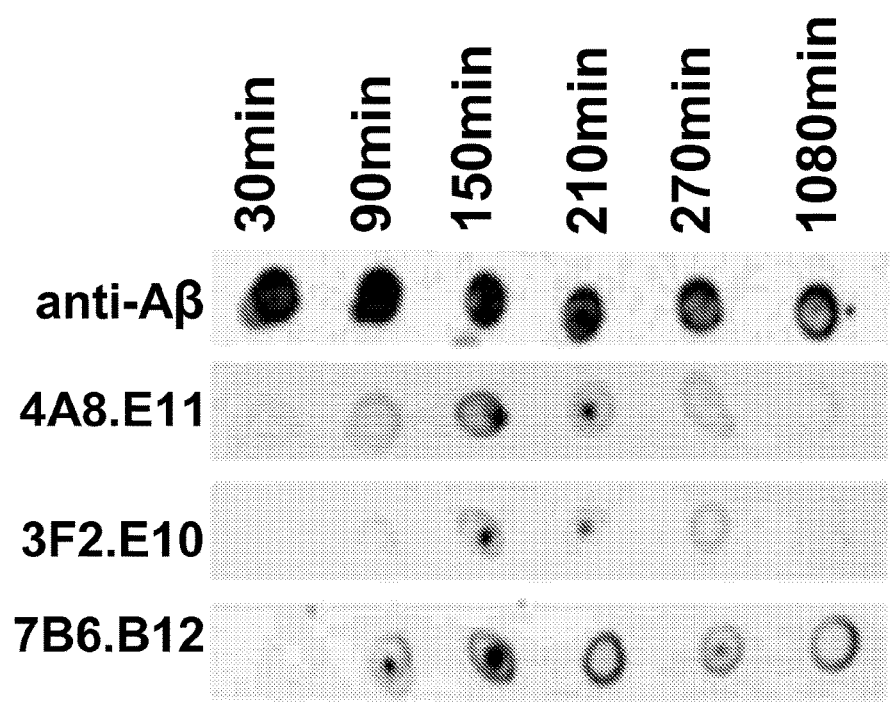

The data in FIGS. 18A, B, C, D, and E show that mAb 4a8.e11, 3f2.e10, and 7b6.b12 detect specific structures along the aggregation pathway of Aβ$_{1-42}$ and display different binding affinities. The 4a8.e11 mAb detects structures present as early as 30 minutes and preferentially detects structures at 150 minutes. The 3f2.e10 mAb detects structures present as early as 90 minutes and preferentially detects structures at 150 minutes. The 7b6.b12 mAb detects structures present as early as 90 minutes, preferentially detects structures at 150 minutes, and can detect structures present in the completed fibrillization time point of 1080 minutes.

Example 11. Binding of mAb 5c9.a2 to TTR Amyloid but not Native TTR Tetramers

Figure 19:
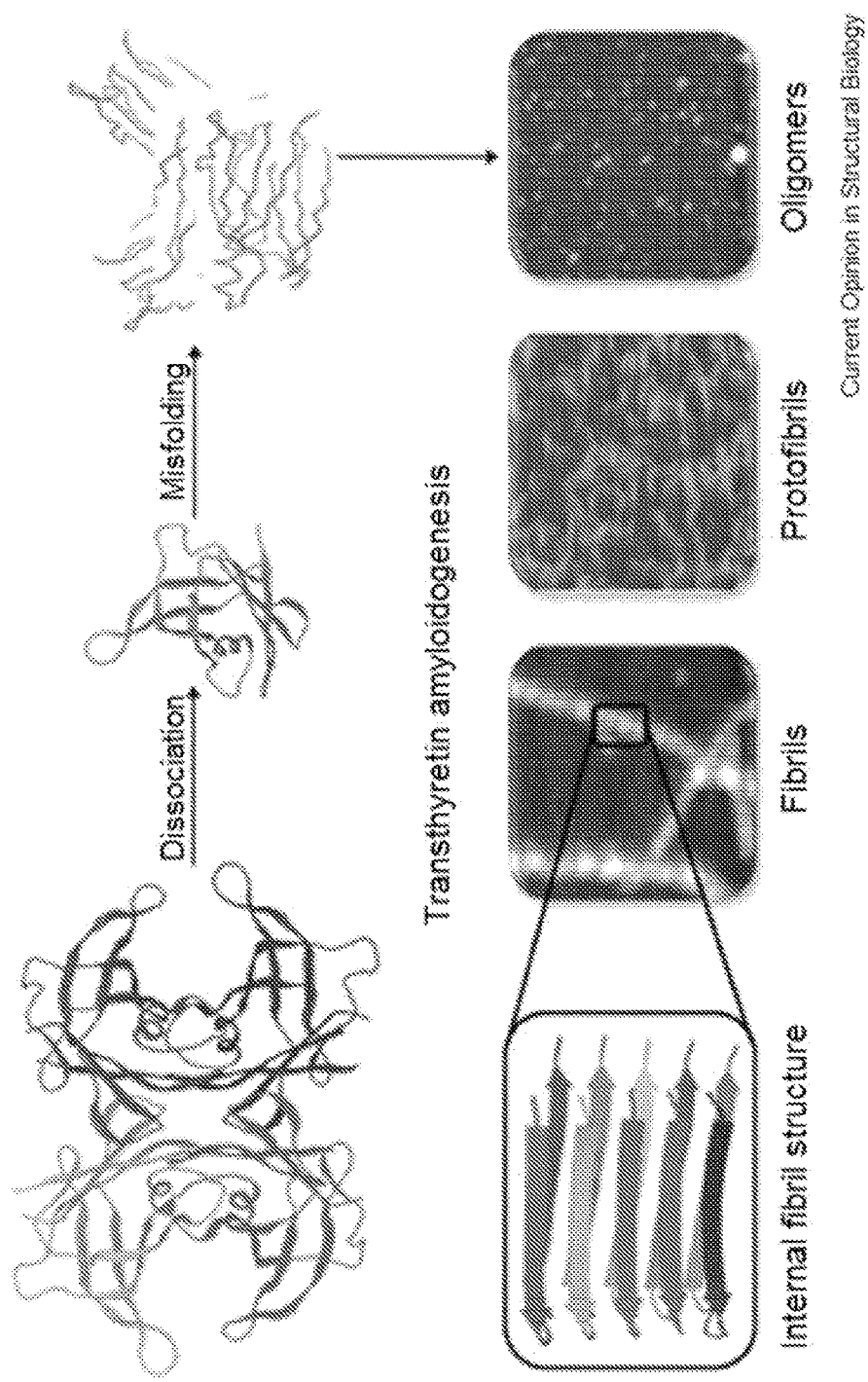
FIGS. 19 A, B, C, and D show that Tetrameric TTR can be converted to amyloid and TTR protofibrils that can be detected with anti-protofibril mAb 5C9.A2. (A.) The schematic shows how TTR tetramer can dissociate into monomers and then misfold into amyloidogenic species that can aggregate to form mature fibrils (adapted from Connelly, S. et al. Current Opinion in Structural Biology, 2010). (B) Acid treated wild-type human TTR dissociates from the native tetrameric species and self aggregates when amyloidogenic. (C) Fluoresence over time in the incubated mixture of acid-treated TTR. (D) Acid treated TTR was allowed to aggregate over time and samples were removed at the times indicated. The anti-protofibril mAb 5C9.A2, detects protofibril intermediates of TTR but not normally folded TTR tetramers.
Figure 19:
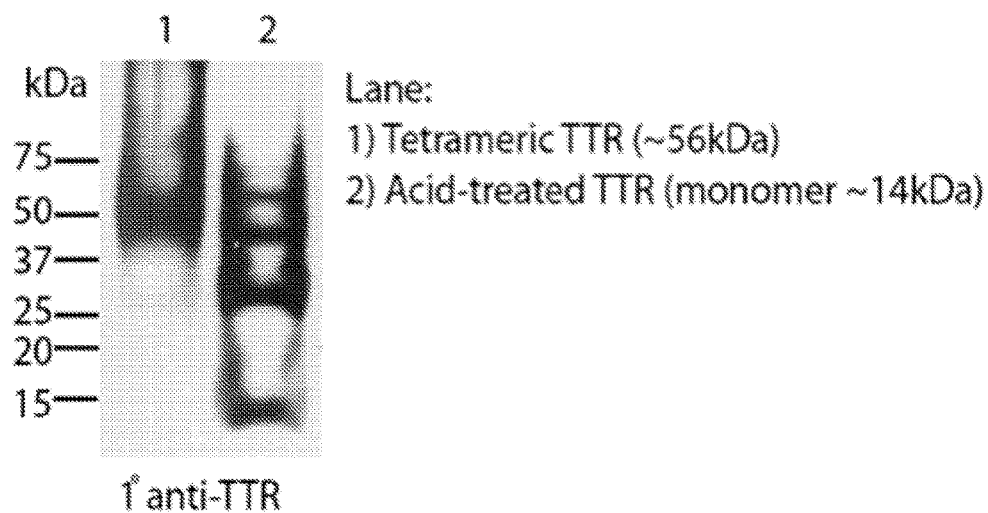
Figure 19:
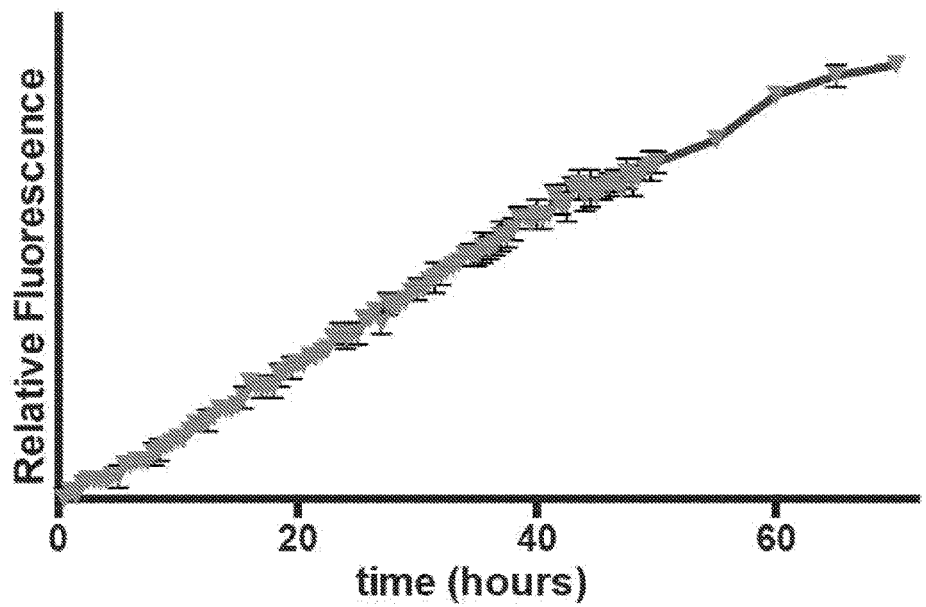
Figure 19:
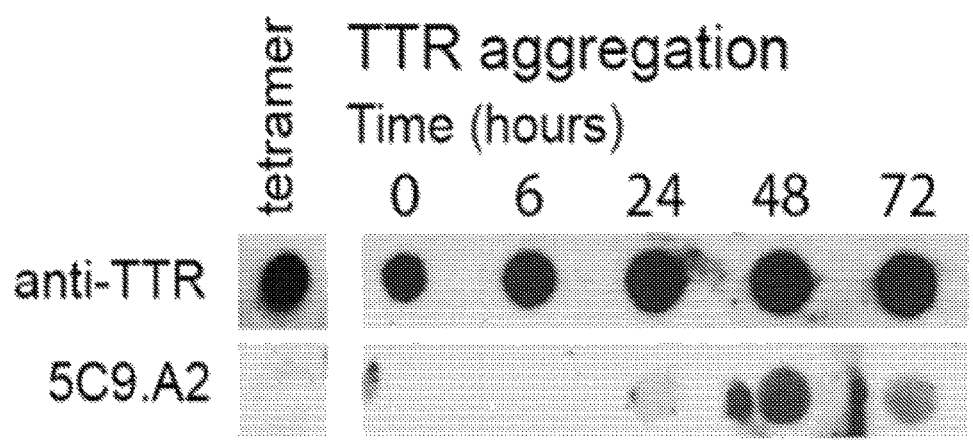

Acid treatment of human wildtype TTR was used to yield mis-folding and self-assembly into amyloid (FIG. 19A; Connelly, S. et al. Current Opinion in Structural Biology, 2010). Samples from the acid treated material were also subjected to native gel electrophoresis and shown to be dissociated into monomers and other species (17B). Human wildtype TTR was acid treated and monitored for amyloid formation by monitoring relative fluorescence (FIG. 19C). Acid treated TTR was allowed to aggregate over time and samples were removed at 0, 6, 24, 48, and 72 hours and reacted with a positive control antibody that binds TTR or the mAb 5c9.a2 (FIG. 19D). The anti-protofibril mAb, 5C9.A2, detected protofibril intermediates of TTR present at the 24 hr (lowest level)), 48 hr (highest level), and 72 hr (intermediate level) time points but not normally folded TTR tetramers (FIG. 19D).

Figure 20:
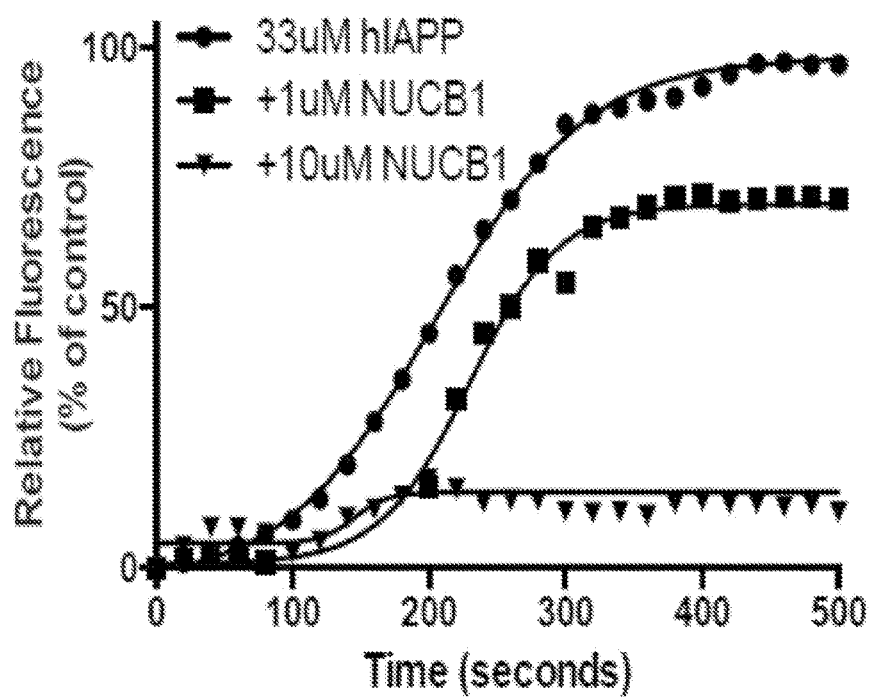
FIGS. 20A, B, and C show NUCB1 stabilization and purification of hIAPP amyloid structures. A) Thioflavin T was used to monitor aggregation kinetics of hAIPP alone (circles) or in the presence of 1 μM (squares) or 10 μM (inverted triangles) NUCB1. B) Preparations of NUCB1-capped hIAPP protofibrils were purified using gel-filtration chromatography resulting in two major protein peaks. C) Dot blot analysis of fractions taken from peak 1 or peak 2 were probed for NUCB1 or hIAPP.
Figure 20:
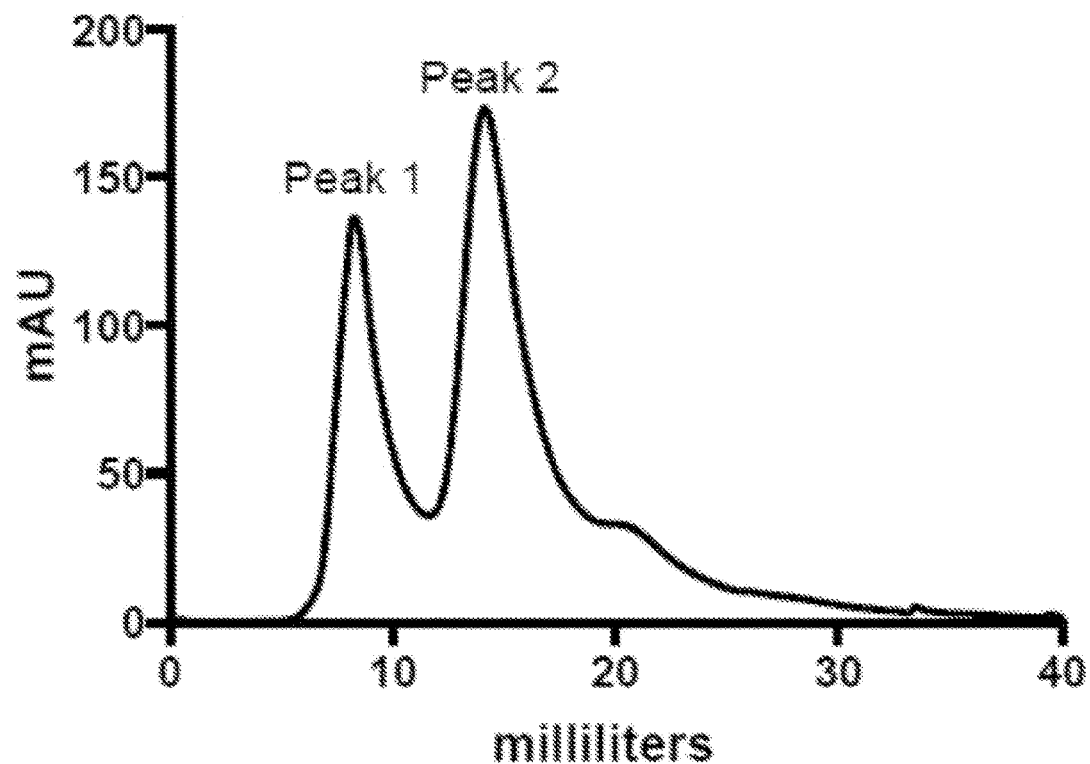
Figure 20:
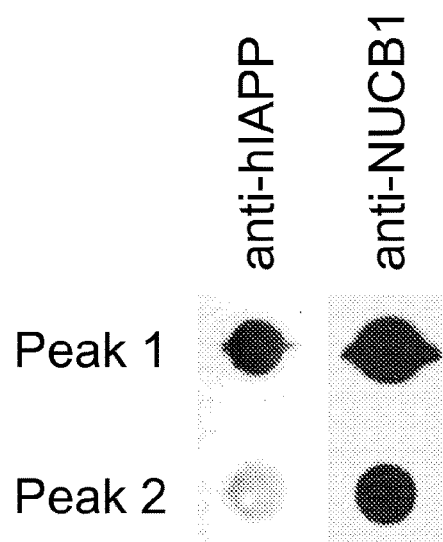

Example 12. Further Characterization of NUCB1 Interactions with Protofibrils and scsAb The effect of NUCB1 on the kinetics of amyloid aggregation was examined as follows. Enhancement in the fluorescence of Thioflavin T increases when it binds to amyloid. Thioflavin T fluorescence was used to monitor the kinetics of amyloid aggregation in the absence or presence of NUCB1 (FIG. 20A). Fluorescence measurements were performed on a Jobin-Yvon Horiba fluorescence spectrophotometer using an excitation wavelength of 450 nm and an emission wavelength of 485 nm. Reactions contained 10 µM Thioflavin T and were conducted at 25° C.

NUCB1-capped protofibrils were characterized by size-exclusion chromatography (FIG. 20B). NUCB1-capped hIAPP protofibrils were isolated using a Superose 6 10/30 GL SEC column (GE Healthcare, Piscataway, N.J.) equilibrated in 20 mM Tris-HCl, pH 7.5. Typically, a 500 uL solution of equimolar NUCB1 and hIAPP reacted under controlled conditions was applied to the column with 20 mM Tris-HCl, pH 7.5. The void volume peak was collected for subsequent immunization experiments.

Dot blot immunoblot assays were used to characterize the peak fractions of the NUCB1-capping procedure; FIG. 20C). Dot blot assays of peak fractions were performed with anti-NUCB1 or anti-hIAPP antibodies by blotting samples onto activated polyvinylidene fluoride membranes using a Bio-Dot SF microfiltration apparatus (Biorad). Membranes were then blocked with 5% Milk TBST or Pierce Protein-Free Blocking Buffer (PFBB, Thermo Scientific) for 1 hour at room temperature. Primary anti-NUCB1 or anti-hIAPP antibodies were applied in blocking buffer for 2 hours at room temperature and membranes were subsequently washed 3 times for 5 minutes each with TBS-Tween (20 mM Tris-HCl, pH 7.5, 150 mM NaCl, 0.05% Tween-20) at room temperature. The membranes were then incubated with horseradish-peroxidase-conjugated secondary antibody in blocking buffer for 1 hour at room temperature followed by 3 washes with TBS-Tween for 5 minutes each. The blots were developed using the SuperSignal West Pico Substrate (Thermo Scientific).

Figure 21:
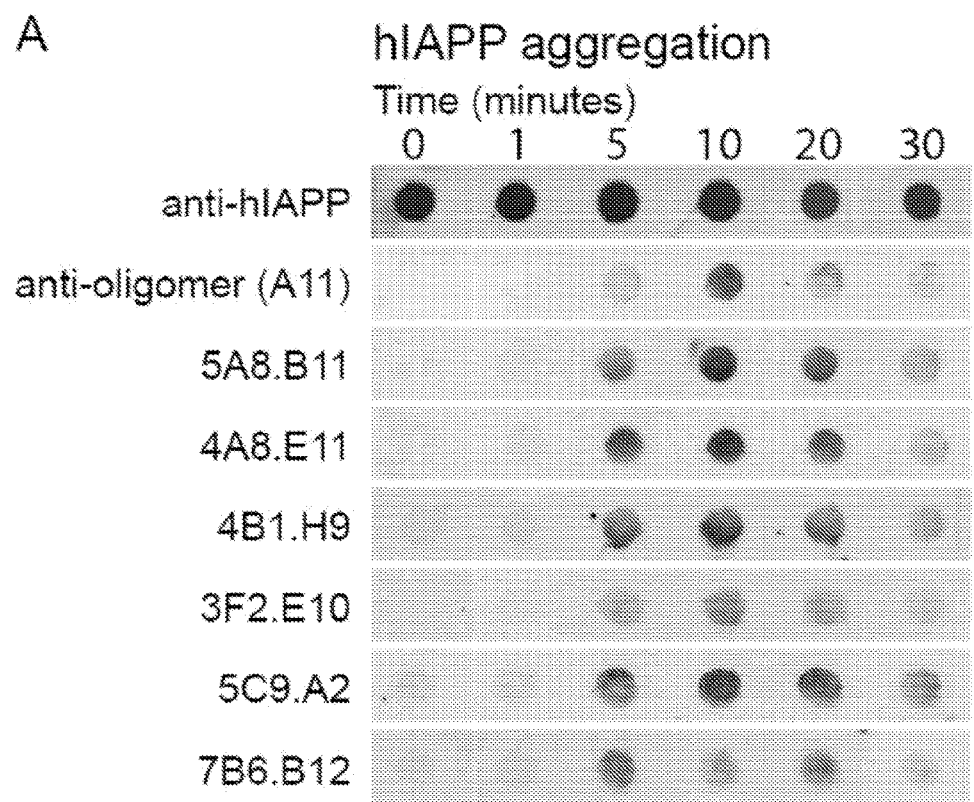
FIG. 21A, B. Selected monoclonal antibodies detect protofibril amyloid morphotypes. A) Time points during hIAPP aggregation were used to determine mAb specificity to discrete on-pathway structures. Similarly, time points during Aβ42 aggregation were probed with select mAbs.
Figure 21:
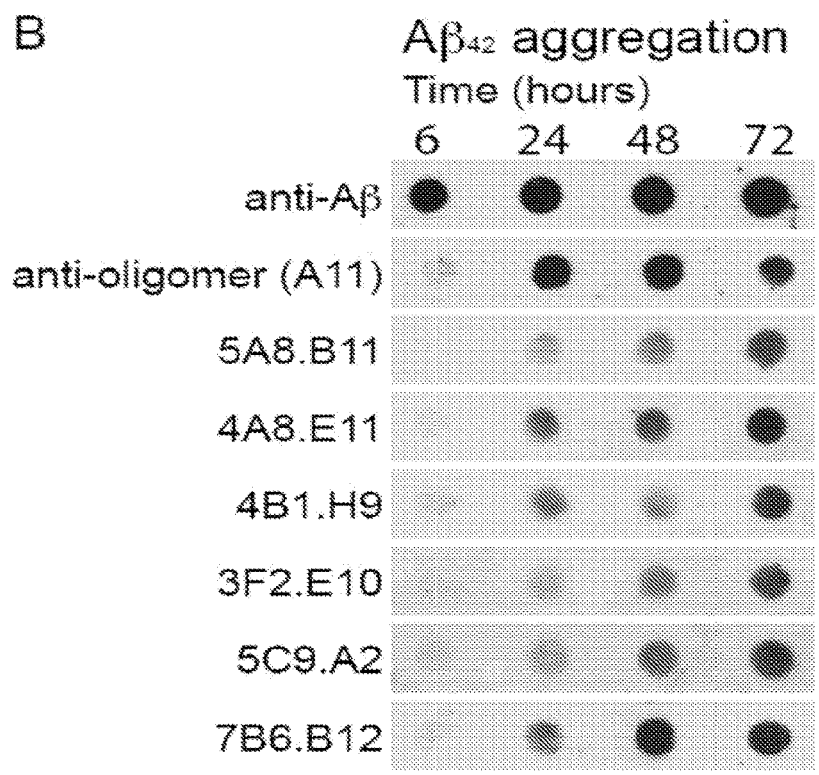

Amyloid aggregation time-course experiments were also performed (FIGS. 21A and 21B). The hIAPP aggregation experiments (FIG. 21A) were performed by diluting an hexafluoroisopropanol (HFIP) stock solution of hIAPP into 20 mM Tris-HCl, pH 7.5 at room temperature. Each time point was immediately spotted on an activated polyvinylidene fluoride membranes using a Bio-Dot SF microfiltration apparatus (Biorad) followed by microfiltration. Membranes were then blocked with Pierce Protein-Free Blocking Buffer (PFBB, Thermo Scientific) for 1 hour at room temperature and probed using the indicated antibodies (5A8.B11, 4A8.E11, 4B1.H9, 3F2.E10, 5C9.A2, and 7B6.B12). To assay Aβ42 aggregation over time (FIG. 21B), Aβ42 synthetic peptides were solubilized in HFIP for 1 hour at room temperature followed by a 10-minute sonication and drying with a steady stream of argon gas. Dried peptide was then solubilized in DMSO and stored at −80° C. Prepared peptide was diluted in 20 mM sodium phosphate, 0.2 mM EDTA and allowed to aggregate without stirring at 37° C. Each time point was collected, diluted in buffer, snap frozen in liquid nitrogen, and stored at −20° C. Subsequent dot blot analysis was performed as described above.

Enhancement in Thioflavin T fluorescence was used to monitor the kinetics of amyloid aggregation in the absence and presence of antibody (FIG. 22A). Fluorescence measurements were performed either on a Flexstation II$^{384}$ (Molecular Devices) using an excitation wavelength of 450 nm and an emission wavelength of 485 nm. Reactions contained 10 uM Thioflavin T and were conducted at 37° C.

Enzyme-linked immunosorbent (ELISA) assays were performed to determine the relative immunoreactivity of certain antibodies against prefibrillar and fibrillar Aβ42 species (FIG. 22B). The ELISAs were performed using Maxisorp™ 96-well plates (NUNC) coated for 16 h at 4° C. with 50 μl/well of antibody in coating buffer (0.2M carbonate buffer, pH 9.5). After rinsing three times with 100 μl ELISA wash buffer (0.1M sodium phosphate, 0.15M NaCl, 0.05% Tween 20) the wells were treated for 1 hour with 100 μl Protein Free Blocking Buffer of 2% BSA. The wells were then incubated for 2 h 50 μl of diluted in blocking buffer. After three washes the wells were incubated for 1 hour with 50 μl anti-Aβ antibody prepared in blocking buffer. After three washes the wells were incubated for 1 hour with 100 μl goat anti-rabbit IgG-HRP conjugate. After three washes 100 μl of freshly made Amplex Red™ (Invitrogen, Milan, Italy) substrate solution (5 μM Amplex UltraRed™ in 50 mM sodium citrate, pH 6.0 with the addition of $H_2O_2$) was added. After 45 minutes incubation at room temperature in the dark, HRP activity was detected by measuring fluorescence with a microplate reader set for excitation in the range of 530-560 nm and emission-detection at 590 nm.

Figure 22:
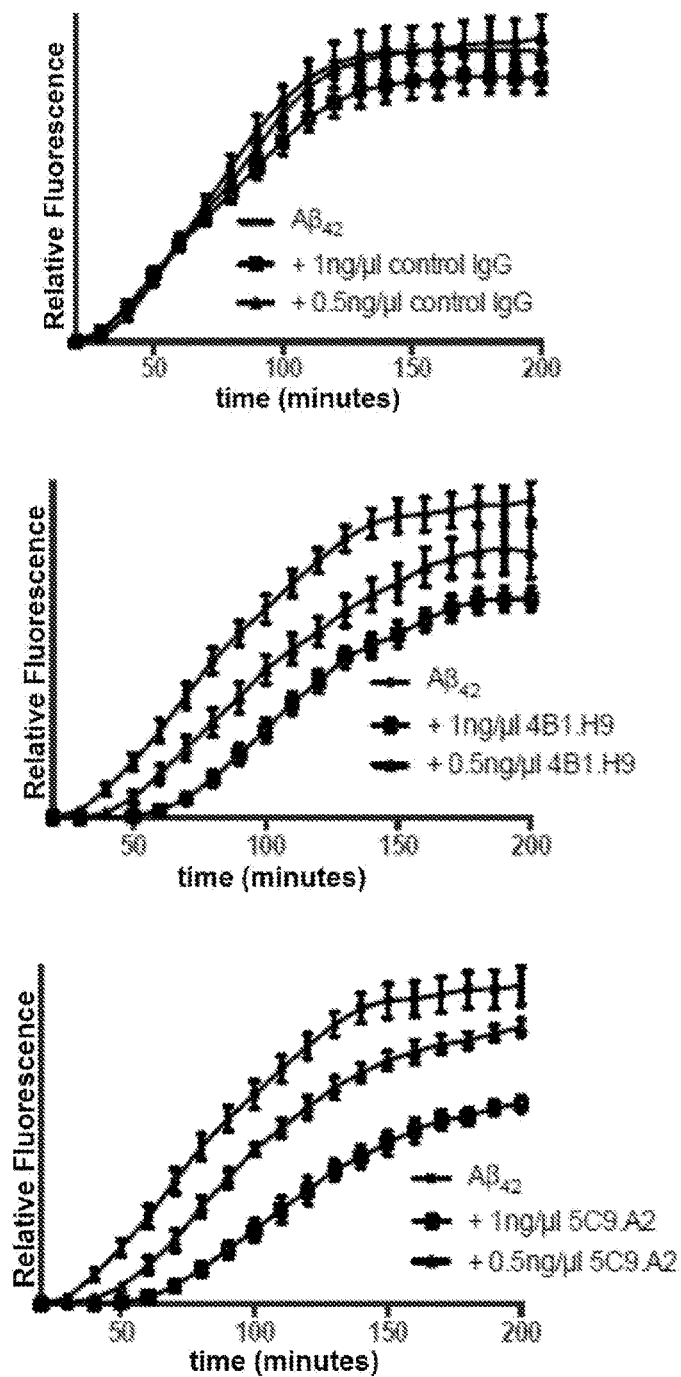
FIG. 22A, B, C, D, E. Use of anti-protofibril mAbs to detect Alzheimer's disease related to Aβ42. A) In a biophysical assay of Aβ42 fibril formation, mAbs 4B1.H9 and 5C9.A2 delay and reduce fibril formation in a dose-dependent manner. B) Sandwich ELISA analysis shows that pre-fibrillar preparations of Aβ42 but not fibrillar preparations can be captured by conformation-specific mAbs and, subsequently, Aβ42 concentration can be analyzed. C) Conformation-specific mAbs stain pyramidal cells in Familial Alzheimer's Disease (FAD) human brain tissue. Human cortex tissue from either normal healthy controls or patients with FAD were stained with, anti-Aβ42, 5A8.B11, 4A8.E11, 4B1.H9 or 5C9.A2. The results show staining (darkened areas) of plaques and pyramidal neurons for anti-Aβ42 antibody, but only pyramidal neurons with conformation-specific mAbs. D (Unaffected Control) and E (Alzheimer's Diseased) Immunofluorescence analysis of unaffected or diseased frontal cortex at either Layer 1 (left) or Layer III (right). Anti-Aβ42 antibody is shown in red and conformation-specific mAbs are in green in color photos. Certain immunofluorescent signals from the anti-Aβ42 antibody are indicated with arrowheads and certain immunofluorescent signals from the indicated conformation-specific mAbs are indicated with arrows.
Figure 22:
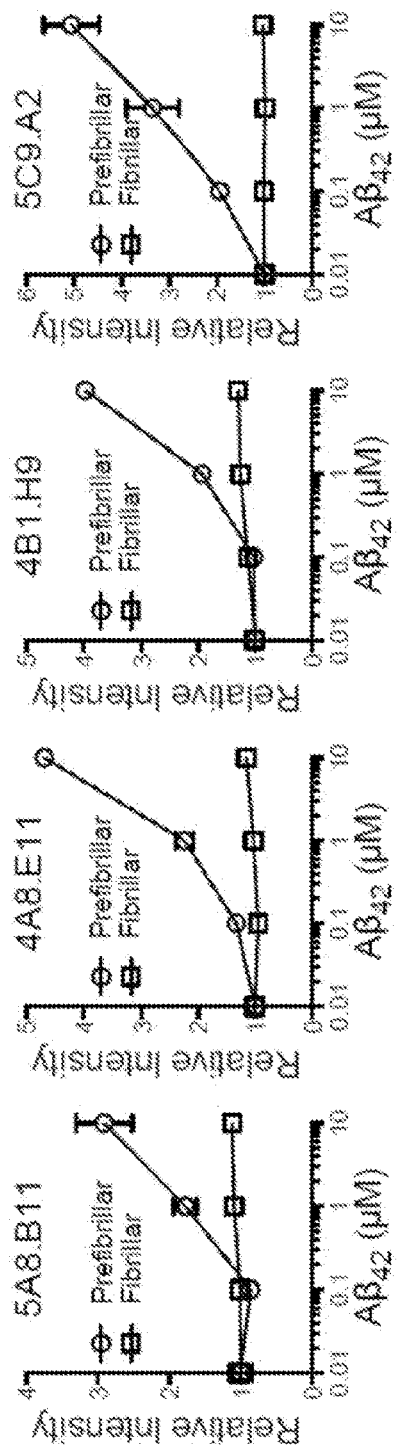
Figure 22:
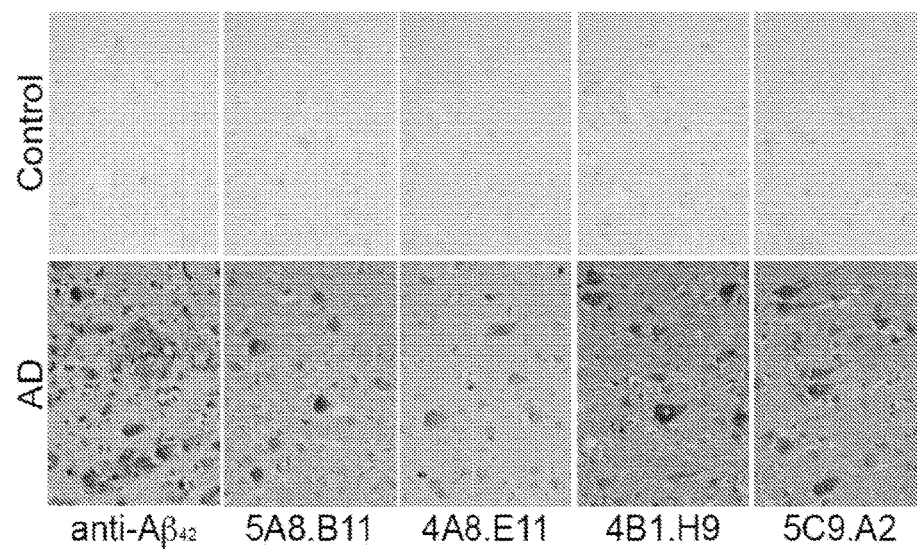
Figure 22:
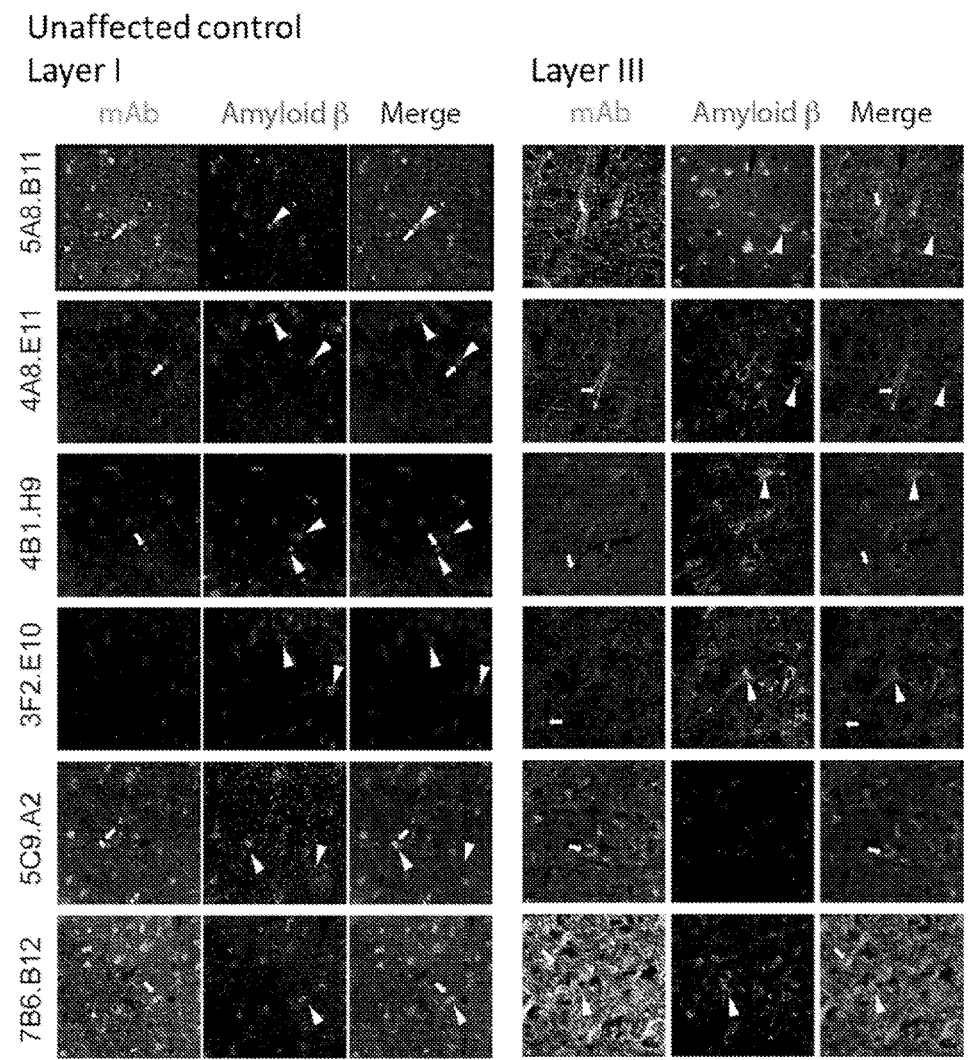
Figure 22:
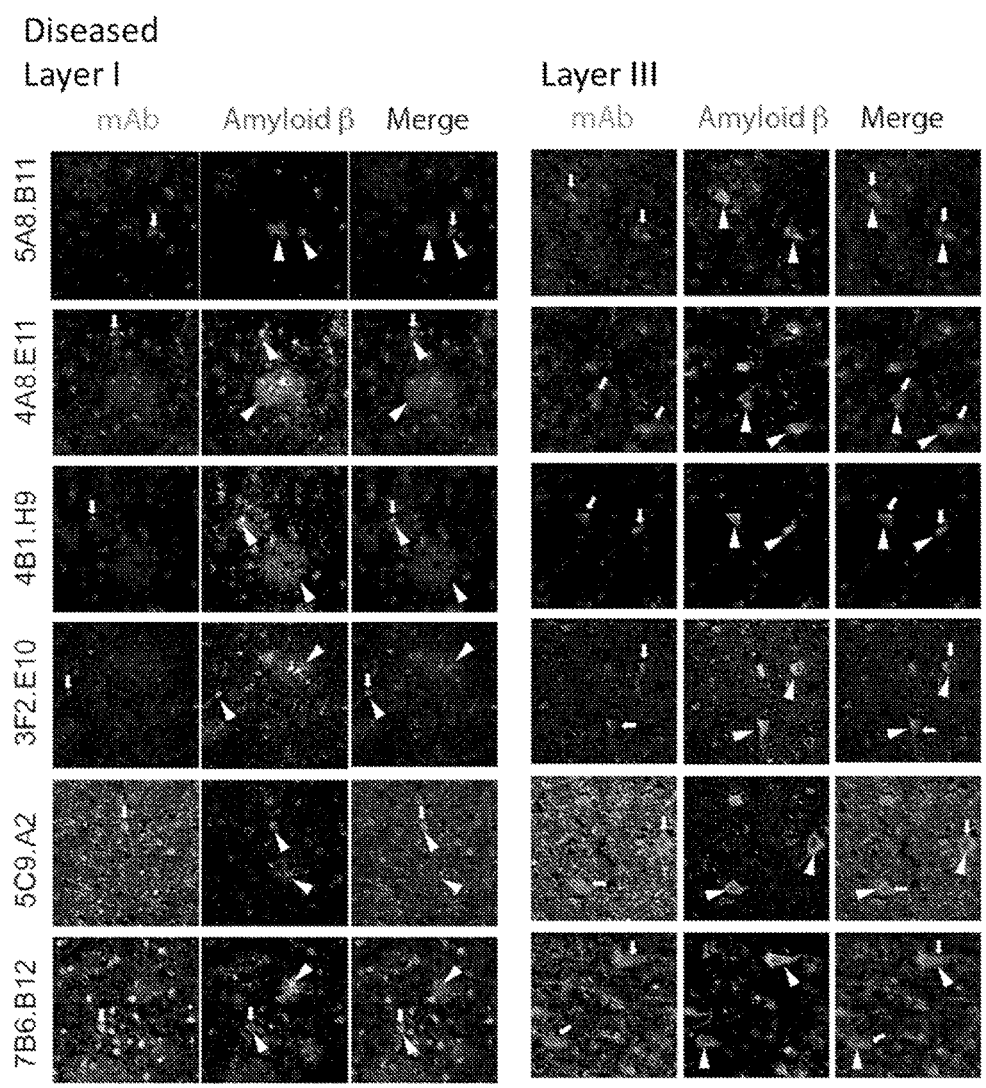

The scsAb (anti-protofibril antibodies) were used to study brain tissue specimens (FIGS. 22 C, D, and E). All brain materials were obtained from the Huddinge Brain Bank at Karolinska Institutet Alzheimer Disease Research Center, Huddinge, Sweden. All Alzheimer's disease (AD) subjects that were sporadic cases met the criteria for definitive AD according to the Consortium to Establish a Registry for AD (CERAD). The control subjects had no known symptoms of neurological or psychiatric disorders. Immunohistochemistry was performed on 7 μm-thick sections cut from formaldehyde fixed and paraffin embedded tissues (FIG. 22C). After the dewaxing and rehydration process the sections were treated in a pressure cooker for 1 hour using an antigen retrieval solution (Diva Decloaker™). Slides were blocked with Protein Block Serum-Free (Dako) and the sections were incubated at 4° C. overnight with each antibody diluted in blocking buffer. Slides were then washed 3 times with TBS, pH 7.4, followed by a 10-minute incubation with MACH 3 Probe for mouse antibodies (Biocare Medical). Slides were washed again with TBS 7.4 and the MACH 3 Mouse and Rabbit HRP Polymer detection system (BIOCARE MEDICAL) was used for detection of mouse monoclonal antibodies. All sections were counterstained with haematoxylin. Sections were analyzed with a conventional light microscope (Eclipse 80i microscope; Nikon). In control experiments, primary antibodies were omitted. For the immunofluorescence experiments shown in FIGS. 22D and 22E, slides treated as above and incubated with primary antibody (directly labeled or not) were washed 3 times with TBS pH7.4 followed by Alexa conjugated secondary antibodies directed to primary antibodies that were not already labeled with fluorescent dye. After a 1 hour incubation in Protein Block Serum-Free blocking buffer, slides were washed with TBS and mounted with DAPI-containing mounting medium (H-1200; Vector Laboratories, Burlingame, Calif., USA). Slides were visualized using an inverted laser-scanning confocal microscope (LSM 510 META; Zeiss, Thornwood, N.Y., USA). In control experiments, primary antibodies were omitted.

Example 13. Generation of mAb Directed Against Mutant TTR and Other Amyloid Protofibrils Immunization of mice will be with NUCB1 capped IAPP, NUCB1 capped TTR or NUCB1 capped mutant TTR, and capped Aβ42 (and potentially alternating mixtures of the above). The NUCB1 capped mutant TTR can be selected from the group consisting of NUCB1 capped V30M, V122I, T60A, L111M, A25T and D18G mutant TTR. Three groups of 10 mice will be immunized and boosted 3-4 times. Serum bleeds will be assessed for reactivity as follows. (I) Positive ELISA Binding to NUCB1-capped mutant TTR (V30M & V122I) and NUCB1-capped Aβ42. (OD450 nm>4.0 relative to background of ~0.4) and positive (blinded assessment and semi-quantitative) for slides previously shown to be positive for tau by immuno-histochemistry on frozen tissue sections, including immuno-precipitation/mass spectrometry confirmation for the presence of tau in the tissue section. (II) Does not bind to native TTR in either its monomeric or tetrameric form nor to NUCB1 alone by ELISA. (II) Cross-reactive to cynomolgus TTR amyloid protofibrils (and possibly mouse TTR amyloid protofibrils) to enable toxicology studies. Such cynomolgus TTR amyloid protofibrils and mouse TTR amyloid protofibrils can be obtained by NUCB1 capping of cynomolgus TTR amyloid protofibrils and mouse TTR amyloid protofibrils. There should be no need to demonstrate cross-reactivity with rodent tau or Aβ42 as these animal models of Alzheimer's Disease use human transgenes.

Fulfillment of these criteria will trigger hybridoma fusions and the generation of monoclonal antibodies which will be re-tested as above to identify lead candidates that are mouse anti human TTR protofibril antibodies (scsAb). Affinity rank ordering of binding constants ($K_D$) by Surface Plasmon Resonance to mutant TTR and Aβ42 will also be determined. Lead candidates that are effective in functional cell based assays and in the mouse model of mutant TTR disease (see below) will then be subsequently humanized and re-tested.

As the target immunogens are protofibrils capped by the NUCB1 molecule with a defined size and degree of order, the screening of a human Phage Antibody library will also be conducted. The criteria will for desirable reactivity will be as described above—however, separate rounds of panning may alternate on the various different targets of capped IAPP, TTR or TTR mutant(s), and Aβ42, and of differing species in order to ensure the desired cross-reactivity. The NUCB1 capped mutant TTR can be selected from the group consisting of NUCB1 capped V30M, V122I, T60A, L111M, A25T and D18G mutant TTR. The phage library derived antibodies are already human antibodies which will be subsequently affinity matured.

Example 14. Testing of Candidate Antibodies that Recognize Mutant TTR Protofibrils There are three relevant functional tests to determine if the candidate antibodies have the requisite properties for lead development—(i) ability to inhibit aggregation of mutant human TTR into amyloid fibril (ii) ability to inhibit protofibril induced cell death (iii) ability to bind to the mutant TTR molecules present in the plasma of FAP and FAC patients.

For the first test of ability to inhibit aggregation of TTR in a fluorescence based biochemical assay the antibodies will be tested dose-responsively relative to an isotype control antibody (specific for physiologically irrelevant antigen) and they will be rank ordered by percent inhibition of the relative fluorescence signal at a time point of maximal dynamic range. Inhibition of aggregation of Aβ42 will be similarly tested. See FIGS. 20A and 20B.

For the second test of ability to inhibit fibril induced cell death a stimulus dose response curve will be generated for both the mutant TTR V30M & V122I and the Aβ42 toxic species. The ability of the antibodies to inhibit cell death by standard MTT cytotoxicity assays using PC12 or other cell lines at the appropriate EC80 values for each stimulus will be measured dose responsively to determine efficacy and potency with rank ordering by IC50 values.

For the third test of ability to bind mutant TTR from clinical samples the antibodies will be tested in an ex vivo assay for the ability to bind by dose-responsive ELISA positivity to clarified FAP and FAC plasma samples from patients relative to normal control plasma samples, with mutant TTR confirmation by Western blot and tandem mass spectrometry.

Example 15. Testing of Antibodies in Transgenic Mouse Models of TTR Disease

From these series of in vitro assays of Examples 12 and 13, the most potent clones that are functionally effective in the biochemical and cell based assays will be selected for testing in in vivo models of mechanistically relevant biology. The human disease FAP is somewhat re-capitulated by mice transgenic for mutants of the human transthyretin protein—specifically TTR null mice transgenic for the human transthyretin with Valine 30 mutated to Methionine or Leucine 55 mutated to Proline (Santos et al. Neurobiol Aging. 2010 February; 31(2):280-9; Sousa et al., Am J Pathol. 2002 November; 161(5):1935-48.

Depending on the mouse strain (usually C57BL/6), the promoter (metallothionein or human homologous) and the absence of heat shock transcription factor 1, mice develop high nM to mM plasma levels of mutant human TTR, measurable amyloid deposition in organs such the mucosa, small intestine, skin, heart and/or nervous system. Pharmacologic agents such as the anti oxidative β adrenergic antagonist Carvedilol™ have been described as having efficacy at reducing deposited TTR aggregate when treatment is started at 3 months of age and continued for a further three months (Macedo et al., Pharmacol Res. 2010 December; 62(6):514-22.

The test antibodies will be tested dose-responsively by prophylactic parenteral administration in the transgenic TTRV30M/Hsf1KO model mice along with contemporaneous treatments of control transgenic TTRV30M/Hsf1KO mice per os with 2 mg/kg/day Carvedilol. Normal, non-diseased mice will also be included as a reference control in the ex vivo assays to demonstrate drug in vivo exposure, mutant TTR target coverage and TTR protofibril target function modulation.

The best mouse anti human/mouse TTR monoclonal antibody will ultimately be converted to a human anti human TTR monoclonal antibody for use as a clinical probe by standard CDR grafting with rational back-mutations as necessary in order to maximize the potency of the parental murine antibody—this humanized antibody will also be re-tested in the in vitro biochemical and cell based assays and the mechanistically relevant in vivo models as previously described. Phage library derived human antibodies will be affinity matured and similarly tested in vivo Example 16. Clinical Studies FAP and FAC are caused by documented mutations in the TTR gene, enabling straightforward prospective stratification for a proof-of-mechanism clinical study. Tafamidis has been shown to exhibit proof-of-mechanism within 6 weeks of dosing by ex vivo analysis of the plasma levels of the drug stabilized TTR tetramer using an immuno-turbidimetric assay in patients with multiple mutant TTR genotypes—and to cause an improvement in disease signs and symptoms in FAP patients within 6-18 months, principally with the V30M mutation ((Bulawa et al. Proc Natl Acad Sci USA. 2012 Jun. 12; 109(24):9629-34; Ruberg F L and Berk J L. Circulation. 2012; 124:1286-1300; Scott L J. Drugs. 2014 Jul. 15; Merlini et al., Cardiovasc Transl Res. 2013 Dec.; 6(6):1011-20. doi: 10.1007/s12265-013-9512-x). The anti protofibril Mab clinical candidate identified in examples 12-14 is designed to antagonize mutant TTR protofibril development into deposited fibrils and hence we envisage testing in a similar prospectively stratified V30M FAP and V122I FAC patient population. Inclusion Criteria: Aged 18-75 years with documented V30M or V122I mutation of transthyretin; biopsy confirmed amyloid deposits; peripheral or autonomic neuropathy with a Karnovsky performance status of C50. Exclusion Criteria: Presence of primary amyloidosis; other causes of sensorimotor neuropathy; absence of a recordable sensory threshold for vibration perception in both feet; liver function test abnormalities; prior liver transplantation; renal insufficiency. Possible Clinical End-Points: Neuropathy Impairment Score-Lower Limbs response rate and the least-square mean change from baseline in the Norfolk Quality-of-Life Diabetic-Neuropathy Questionnaire total scores at 18 months.

Example 17. Summary of Biological, Antibody, and Primer Sequences

TABLE 5

Sequences

| SEQ ID NO: | Description | Sequence |
|---|---|---|
| 1 | Human NUCB1 NCBI Accession Number NP_006175.2 | MPPSGPRGTLLLLPLLLLLLRAVLAVPLERGAPNKEETPAT ESPDTGLYYHRYLQEVIDVLETDGHFRE KLQAANAEDIKSGKLSRELDFVSHHVRTKLDELKRQEVSRL RMLLKAKMDAEQDPNVQVDHLNLLKQFEH LDPQNQHTFEARDLELLIQTATRDLAQYDAAHHEEFKRYE MLKEHERRRYLESLGEEQRKEAERKLEEQQ RRHREHPKVNVPGSQAQLKEVWEELDGLDPNRFNPKTFFIL HDINSDGVLDEQELEALFTKELEKVYDPK NEEDDMREMEEERLRMREHVMKNVDTNQDRLVTLEEFLA STQRKFFGDTGEGWETVEMHPAYTEEELRRF EEELAAREAELNAKAQRLSQETEALGRSQGRLEAQKRELQ QAVLHMEQRKQQQQQQGHKAPAAHPEGQL KFHPDTDDVPVPAPAGDQKEVDTSEKKLLERLPEVEVPQHL |
| 2 | Bos Taurus NUCB1 | MPPSGPRAALFLLPSLLLLRAVLAVPLERGAPKEENPATESP DTGLYYHRYLQEVINVLETDGHFREKLQ AANAEDIKSGKLSRELDFVSHHVRTKLDELKRQEVSRLRM LLKAKMDAQQEPNIQLDHLNLLKQFEHLDP QNQHTFEARDLELLIQTATRDLAQYDAAHHEEFKRYEMLK EHERRRYLESLGEEQRKEAERKLEEQQRRH REHPKVNVPGSQAQLKEVWEELDGLDPNRFNPKTFFILHDI NSDGVLDEQELEALFTKELEKVYDPKNED DDMREMEEERLRMREHVMKNVDTNQDRLVTLEEFLASTQ RKEFGDTGEGWEQGKAGVPLPMAPVLTLQTV EMHPAYTEEELRRFEEELAAREAELNAKAQRLSQETEALGR SQGRLEAQKRELQQAVLQMEQRKQQQQSH NNPAPGPEGQLKFHPDTDDVPVPAPAGDQKDVDASEKKVP EQTPEPPQLDSQHL |
| 3 | Sus scrofa NUCB1 | MPPYGTLTALLLLPPLLLLHAVLAVPLDRGASKEENPATES PDTGLYYHRYLQEVINVLETDGHFREKLQ AANAEDIKSGKLSRELDFVSHHVRTKLDELKRQEVSRLRM LLKAKMDAEQEPNVQLDHLNLLKQFEHLDP QNQHTFEARDLELLIQTATRDLAQYDAAHHEEFKRYEMLK EHERRRYLESLGEEQRKEAEKKLEEQQRRH REHPKVNVPGSQAQLKEVWEELDGLDPNRFNPKTFFILHDI NSDGVLDEQELEALFTKELEKVYDPKNEE DDMREMEEERLRMREHVMKNVDTNQDRLVTLDEFLASTQ RKEFGDTGEGWETVEMHPAYTEDELRRFEEE LAAREAELNAKAQRLSQETEALGRSQGRLEAQKRELQQAV LQMEQRKQQQGHKDPATGPEGQLKFHPDT DDAPVPAPAGDQKDVDASEKKVPEQTPFLPQLDSQHL |
| 4 | Canis familiaris NUCB1 | MPSSGPRAALLLLPPLLLLRAVLAVPLERGAPKQESPATESP DTGLYYHRYLQEVINVLETDGHFREKLQ AANAEDIKSGKLSRELDFVSHHVRTKLDELKRQEVSRLRM LLKAKMDAEQEPNVQLDHLSLLKQFEHLDP QNQHTFEARDLELLIQTATRDLAQYDAAHHEEFKRYEMLK EHERRRYLESLGEEQRKEAERKLEEQQRRH REHPKVNVPGSQAQLKEVWEELDGLDPNRFNPKTFFILHDI NSDGVLDEQELEALFTKELEKVYDPKNEE DDMREMEEERLRMREHVMKNVDTNQDRLVTLEEFLASTQ RKEFGDTGEGWETVEMHPAYTEEELRRFEEE LAAREAELNAKAQRLSQETEALGRSQGRLEAQKRELQQAV LQMEQRKQQQNQNSPAPGPEGQLQFHPDT DDAPVPAPAGDQKDADTSEKKAPDQPPELPQLDTQHL |
| 5 | Heavy chain Igh 1st PCR 5' MsVHE | GGGAATTCGAGGTGCAGCTGCAGGAGTCTGG |
| 6 | Heavy chain Igh 1st PCR 3' Cµ outer | AGGGGGCTCTCGCAGGAGACGAGG |

TABLE 5-continued

Sequences

| SEQ ID NO: | Description | Sequence |
|---|---|---|
| 7 | Heavy chain Igh 1st PCR 3' Cγ1 outer | GGAAGGTGTGCACACCGCTGGAC |
| 8 | Heavy chain Igh 1st PCR 3' Cγ2c outer | GGAAGGTGTGCACACCACTGGAC |
| 9 | Heavy chain Igh 1st PCR 3' Cγ2b outer | GGAAGGTGTGCACACTGCTGGAC |
| 10 | Heavy chain Igh 1st PCR 3' Cγ3 outer | AGACTGTGCGCACACCGCTGGAC |
| 11 | Heavy chain Igh 1st PCR 3' Cα outer | GAAAGTTCACGGTGGTTATATCC |
| 12 | Heavy chain Igh 2nd PCR 5' MsVHE | GGGAATTCGAGGTGCAGCTGCAGGAGTCTGG |
| 13 | Heavy chain Igh 2nd PCR 3' Cµ inner | AGGGGGAAGACATTTGGGAAGGAC |
| 14 | Heavy chain Igh 2nd PCR 3' Cγ1 inner | GCTCAGGGAAATAGCCCTTGAC |
| 15 | Heavy chain Igh 2nd PCR 3' Cγ2c inner | GCTCAGGGAAATAACCCTTGAC |
| 16 | Heavy chain Igh 2nd PCR 3' Cγ2b inner | ACTCAGGGAAGTAGCCCTTGAC |
| 17 | Heavy chain Igh 2nd PCR 3' Cγinner | GCTCAGGGAAGTAGCCTTTGAC |
| 18 | 3' Cα inner | TGCCGAAAGGGAAGTAATCGTGAAT |
| 19 | Kappa Light chain Igk 1st PCR 5' L-Vκ_3 | TGCTGCTGCTCTGGGTTCCAG |
| 20 | Kappa Light chain Igk 1st PCR 5' L-Vκ_4 | ATTWTCAGCTTCCTGCTAATC |
| 21 | Kappa Light chain Igk 1st PCR 5' L-Vκ_5 | TTTTGCTTTTCTGGATTYCAG |
| 22 | Kappa Light chain Igk 1st PCR 5' L-Vκ_6 | TCGTGTTKCTSTGGTTGTCTG |
| 23 | Kappa Light chain Igk 1st PCR 5' L-Vκ_6,8,9 | ATGGAATCACAGRCYCWGGT |

TABLE 5-continued

Sequences

| SEQ ID NO: | Description | Sequence |
|---|---|---|
| 24 | Kappa Light chain Igk 1st PCR 5' L-Vκ_14 | TCTTGTTGCTCTGGTTYCCAG |
| 25 | Kappa Light chain Igk 1st PCR 5' L-Vκ_19 | CAGTTCCTGGGGCTCTTGTTGTTC |
| 26 | Kappa Light chain Igk 1st PCR 5' L-Vκ_20 | CTCACTAGCTCTTCTCCTC |
| 27 | Kappa Light chain Igk 1st PCR 3' mCκ | GATGGTGGGAAGATGGATACAGTT |
| 28 | Kappa Light chain Igk 2nd PCR 5' mVkappa | GAYATTGTGMTSACMCARWCTMCA |
| 29 | Kappa Light chain Igk 2nd PCR 3' BsiWI P-mJK01 | GCCACCGTACGTTTGATTTCCAGCTTGGTG |
| 30 | Kappa Light chain Igk 2nd PCR 3' BsiWI P-mJK02 | GCCACCGTACGTTTTATTTCCAGCTTGGTC |
| 31 | Kappa Light chain Igk 2nd PCR 3' BsiWI P-mJK03 | GCCACCGTACGTTTTATTTCCAACTTTGTC |
| 32 | Kappa Light chain Igk 2nd PCR 3' BsiWI P-mJK04 | GCCACCGTACGTTTCAGCTCCAGCTTGGTC |
| 33 | Lambda light chain Igl 1st PCR 5' mVλ1/2 | CAGGCTGTTGTGACTCAG |
| 34 | Lambda light chain Igl 1st PCR 5' mVλx | CAACTTGTGCTCACTCAG |
| 35 | Lambda light chain Igl 1st PCR 3' mCλ outer | GTACCATYTGCCTTCCAGKCCACT |
| 36 | Lambda light chain Igl 2nd PCR 5' mVλ1/2 | CAGGCTGTTGTGACTCAG |
| 37 | Lambda light chain Igl 2nd PCR 5' mVλx | CAACTTGTGCTCACTCAG |

TABLE 5-continued

Sequences

| SEQ ID NO: | Description | Sequence |
|---|---|---|
| 38 | Lambda light chain Igl 2nd PCR 3' mCλ inner | CTCYTCAGRGGAAGGTGGRAACA |
| 39 | 5a8.b11 mAb heavy chain variable region DNA | GAGGTGCAGCTGCAGGAGTCTGGACCTGAGCTGGTGAAG CCTGGGGCTTCAGTGAAGATACCCTGCAAGGCTTCTGGA TACACATTCACTGACTACAACATGGACTGGGTGAAGCAG AGCCATGGAAAGAGCCTTGAGTGGATTGGAGATATTAAT CCTAACAATGGTGGTACTATCTACAACCAGAAGTTCAAG GGCAAGGCCACATTGACTGTAGACAAGTCCTCCAGCACA GCCTACATGGAGCTCCGCAGCCTGACATCTGAGGACACT GCAGTCTATTACTGTGCAAGAAAGGGGGAGAGGGGCTTT GACTACTGGGGCCAAGGCACCACTCTCACAGTCTCCTCA G |
| 40 | 5a8.b11 mAb heavy chain variable region protein | EVQLQESGPELVKPGASVKIPCKASGYTFTDYNMDWVKQS HGKSLEWIGDINPNNGGTIYNQKFKGKATLTVDKSSSTAY MELRSLTSEDTAVYYCARKGERGFDYWGQGTTLTVSS |
| 41 | 5a8.b11 mAb light (kappa) chain variable region DNA | GAAAATGTGCTCACCCAGTCTCCAGCAATCATGTCTGCA TCTCTAGGGGAGAAGGTCACCATGAGCTGCAGGGCCAGC TCAAGTGTAAATTACATGTACTGGTACCAGCAGAAGTCA GATGCCTCCCCCAAACTATGGATTTATTACACATCCAACC TGGCTCCTGGAGTCCCAGCTCGCTTCAGTGGCAGTGGGT CTGGGAACTCTTATTCTCTCACAATCAGCAGCATGGAGG GTGAAGATGCTGCCACTTATTACTGCCAGCAGTTTACTA GTTCCCCATCCACGTTCGGTGCTGGGACCAAGCTGGAGC TGAAAC |
| 42 | 5a8.b11 mAb kappa light chain variable region protein | ENVLTQSPAIMSASLGEKVTMSCRASSSVNYMYWYQQKSD ASPKLWIYYTSNLAPGVPARFSGSGSGNSYSLTISSMEGEDA ATYYCQQFTSSPSTFGAGTKLELK |
| 43 | 5a8.b11 mAb heavy chain HVR H1 region protein | GYTFTDYN |
| 44 | 5a8.b11 mAb heavy chain HVR H2 region protein | INPNNGGT |
| 45 | 5a8.b11 mAb heavy chain HVR H3 region protein | ARKGERGFDY |
| 46 | 5a8.b11 mAb kappa light chain HVR L1 region protein | SSVNY |
| 47 | 5a8.b11 mAb kappa light chain HVR L2 region protein (YTS at residues 18-20) and flanking framework region | MYWYQQKSDASPKLWIYYTSNLAPGVPARFSGSGSGNSYS LTISSMEGEDAATYYC |

TABLE 5-continued

Sequences

| SEQ ID NO: | Description | Sequence |
|---|---|---|
| 48 | 5a8.b11 mAb kappa light chain HVR L3 region protein | QFTSSPST |
| 49 | 4a8.e11 mAb heavy chain variable region DNA | GAGGTGCAGCTGCAGGAGTCTGGGGGAGGCTTAGTGAA GCCTGGAGGGTCCCTGAAACTCTCCTGTGCAGCCTCTGG ATTCACTTTCAGTGACTATGGAATGCACTGGGTTCGTCAG GCTCCAGAGAAGGGACTGGAGTGGGTTGCATACATTAGT AGTGGCAGTAGTACCGTCTACTGTGCAGACACAGTGAAG GGCCGATTCACCATCTCCAGAGACAATGCCAAGAACACC CTGTTCCTGCAAATGACCAGTCTGAGGTCTGAGGACACG GCCATGTATTACTGTGCAAGGCGCTGGGGCTACTTTGAC TACTGGGGCCAAGGCACCACTCTCACAGTCTCCTCAG |
| 50 | 4a8.e11 mAb heavy chain variable region protein | EVQLQESGGGLVKPGGSLKLSCAASGFTFSDYGMHWVRQ APEKGLEWVAYISSGSSTVYCADTVKGRFTISRDNAKNTLF LQMTSLRSEDTAMYYCARRWGYFDYWGQGTTLTVSS |
| 51 | 4a8.e11 mAb light (kappa) chain variable region DNA | GACATCAAGATGACCCAGTCTCCATCTTCCATGTATGCAT CTCTAGGAGAGAGAGTCACTTTCACTTGCAAGGCGAGTC AGGACATTAATAGCTTTTTAAGCTGGTTCCAGCAGAAAC CAGGGAAATCTCCTAAGACCCTGATCTATCGTGCAAACA GATTGGTAGATGGGGTCCCATCAAGGTTCAGTGGCAGTG GATCTGGGCAAGATTATTCTCTCACCATCACCAGCCTGG AGTTTGAAGATATGGGAATTTATTATTGTCTACAGTATGA TGAGTTTCCGTACACGTTCGGAGGGGGGACCAAGCTGGA AATAAAAC |
| 52 | 4a8.e11 mAb kappa light chain variable region protein | DIKMTQSPSSMYASLGERVTFTCKASQDINSFLSWFQQKPG KSPKTLIYRANRLVDGVPSRFSGSGSGQDYSLTITSLEFEDM GIYYCLQYDEFPYTFGGGTKLEIK |
| 53 | 4a8.e11 mAb kappa mAb heavy chain HVR H1 region protein | GFTFSDYG |
| 54 | 4a8.e11 mAb heavy chain HVR H2 region protein | ISSGSSTV |
| 55 | 4a8.e11 mAb heavy chain HVR H3 region protein | ARRWGYFDY |
| 56 | 4a8.e11 mAb kappa light chain HVR L1 region protein | QDINSF |

TABLE 5-continued

Sequences

| SEQ ID NO: | Description | Sequence |
|---|---|---|
| 57 | 4a8.e11 mAb kappa light chain HVR L2 region protein (RAN at residues 18-20) and flanking framework region | LSWFQQKPGKSPKTLIYRANRLVDGVPSRFSGSGSGQDYSL TITSLEFEDMGIYYC |
| 58 | 4a8.e11 mAb kappa light chain HVR L3 region protein | LQYDEFPYT |
| 59 | 4b1.h9 mAb heavy chain variable region DNA | GAGGTGCAGCTGCAGGAGTCTGGACCTGTGCTGGTGAAG CCTGGGGCTTCAGTGAAGATGTCCTGTAAGGCTTCTGGA TACACATTCACTGACTACTATATGAACTGGGTGAAGCAG AGCCATGGAAAGAGCCTTGAGTGGATTGGAGTTATTAAT CCTTACAACGGTGGTACTAGCTACAACCAGAAGTTCAAG GGCAAGGCCACATTGACTGTTGACAAGTCCTCCAGCACA GCCTACATGGAGCTCAACAGCCTGACATCTGAGGACTCT GCAGTCTATTACTGTGCAAGACGGCGAGGCTATGCTATG GACTACTGGGGTCAAGGAACCTCAGTCACCGTCTCCTCA G |
| 60 | 4b1.h9 mAb heavy chain variable region protein | EVQLQESGPVLVKPGASVKMSCKASGYTFTDYYMNWVKQ SHGKSLEWIGVINPYNGGTSYNQKFKGKATLTVDKSSSTAY MELNSLTSEDSAVYYCARRRGYAMDYWGQGTSVTVSS |
| 61 | 4b1.h9 mAb light (kappa) chain variable region DNA | GACATCCAGATGACTCAGTCTCCAGCCTCCCTATCTGCAT CTGTGGGAGAAACTGTCACCATCACATGTCGAGCAAGTG AGAATATTTACAGTTATTTAGCATGGTATCAGCAGAAAC AGGGAAAATCTCCTCAGCTCCTGGTCTATAATGCAAAAA CCTTAGCAGAAGGTGTGCCATCAAGGTTCAGTGGCAGTG GATCAGGCACACAGTTTTCTCTGAAGATCAACAGCCTGC AGCCTGAAGATTTTGGGAGTTATTACTGTCAACATCATTA TGGTACTCCGTACACGTTCGGAGGGGGGACCAACCTGGA AATAAAAC |
| 62 | 4b1.h9 mAb kappa light chain variable region protein | DIQMTQSPASLSASVGETVTITCRASENIYSYLAWYQQKQG KSPQLLVYNAKTLAEGVPSRFSGSGSGTQFSLKINSLQPEDF GSYYCQHHYGTPYTFGGGTNLEIK |
| 63 | 4b1.h9 mAb heavy chain HVR H1 region protein | GYTFTDYY |
| 64 | 4b1.h9 mAb heavy chain HVR H2 region protein | INPYNGGT |
| 65 | 4b1.h9 mAb heavy chain HVR H3 region protein | ARRRGYAMDY |

TABLE 5-continued

Sequences

| SEQ ID NO: | Description | Sequence |
|---|---|---|
| 66 | 4b1.h9 mAb kappa light chain HVR L1 region protein | ENIYSY |
| 67 | 4b1.h9 mAb kappa light chain HVR L2 region protein (NAK at residues 18-20) and flanking framework region | LAWYQQKQGKSPQLLVYNAKTLAEGVPSRFSGSGSGTQFSLKINSLQPEDFGSYYC |
| 68 | 4b1.h9 mAb kappa light chain HVR L3 region protein | HHYGTPYT |
| 69 | 3f2.e10 mAb heavy chain variable region DNA | GAGGTGCAGCTGCAGGAGTCTGGTGGAGGATTGGTGCAGCCTAAAGGGTCATTGAAACTCTCATGTGCAGCCTCTGGATTCAGCTTCAATACCTACGCCATGAACTGGGTCCGCCAGGCTCCAGGAAAGGGTTTGGAATGGGTTGCTCGCATAAGAAGTAAAAGTAATAATTATGCAACATATTATGCCGATTCAGTGAAAGACAGATTCACCATCTCCAGAGATGATTCAGAAAGCATGCTCTATCTGCAAATGAACAACTTGAAAACTGAGGACACAGCCATGTATTACTGTGTGAGACTGGGAGCTATGGACTACTGGGGTCAAGGAACCTCAGTCACCGTCTCCTCAG |
| 70 | 3f2.e10 mAb heavy chain variable region protein | EVQLQESGGGLVQPKGSLKLSCAASGFSFNTYAMNWVRQAPGKGLEWVARIRSKSNNYATYYADSVKDRFTISRDDSESMLYLQMNNLKTEDTAMYYCVRLGAMDYWGQGTSVTVSS |
| 71 | 3f2.e10 mAb light (kappa) chain variable region DNA | GACATTGTGATGACCCAGTCTCAAAAATTCATGTCCACATCAGTAGGAGACAGGGTCAGCGTCACCTGCAAGGCCAGTCAGAATGTGGGTACTAATGTAGCCTGGTATCAACAGAAACCAGGGCAATCTCCTAAAGCACTGATTTACTCGGCATCCTACCGGTACAGTGGAGTCCCTGATCGCTTCACAGGCAGTGGATCTGGGACAGATTTCACTCTCACCATCAGCAATGTGCAGTCTGAAGACTTGGCAGAGTATTTCTGTCAGCAATATAACAGCTATCCGCTCACGTTCGGTGCTGGGACCAAGCTGGAGCTGAAAC |
| 72 | 3f2.e10 mAb kappa light chain variable region protein | DIVMTQSQKFMSTSVGDRVSVTCKASQNVGTNVAWYQQKPGQSPKALIYSASYRYSGVPDRFTGSGSGTDFTLTISNVQSEDLAEYFCQQYNSYPLTFGAGTKLEL |
| 73 | 3f2.e10 mAb heavy chain HVR H1 region protein | GFSFNTYA |
| 74 | 3f2.e10 mAb heavy chain HVR H2 region protein | IRSKSNNYAT |

TABLE 5-continued

Sequences

| SEQ ID NO: | Description | Sequence |
|---|---|---|
| 75 | 3f2.e10 mAb heavy chain HVR H3 region protein | VRLGAMDY |
| 76 | 3f2.e10 mAb kappa light chain HVR L1 region protein | QNVGTN |
| 77 | 3f2.e10 mAb kappa light chain HVR L2 region protein (SAS at residues 18-20) and flanking framework region | VAWYQQKPGQSPKALIYSASYRYSGVPDRFTGSGSGTDFTL TISNVQSEDLAEYFC |
| 78 | 3f2.e10 mAb kappa light chain HVR L3 region protein | QYNSYPLT |
| 79 | 5c9.a2 Heavy chain DNA | GAGGTGCAGCTGCAGGAGTCTGGACCTGTGCTGGTGAAG CCTGGGGCTTCAGTGAAGATGTCCTGTAAGGCTTCTGGA TACACATTCACTGACTACTATATGAACTGGGTGAAGCAG AGCCATGGAAAGAGCCTTGAGTGGATTGGAGTTATTAAT CCTTACAACGGTGGTACTAGCTACAACCAGAAGTTCAAG GGCAAGGCCACATTGACTGTTGACAAGTCCTCCAGCACA GCCTACATGGAGCTCAACAGCCTGACATCTGAGGACTCT GCAGTCTATTACTGTGCATCTTTACGACGCCGGACTGACT ACTTTGACTACTGGGGCCAAGGCACCACTCTCACAGTCT CCTCAG |
| 80 | 5c9.a2 >Heavy chain Protein | EVQLQESGPVLVKPGASVKMSCKASGYTFTDYYMNWVKQ SHGKSLEWIGVINPYNGGTSYNQKFKGKATLTVDKSSSTAY MELNSLTSEDSAVYYCASLRRRTDYFDYWGQGTTLTVSS |
| 81 | 5c9.a2 Light chain (kappa) DNA | GACATTGTGATGACCCAGTCTCACAAATTCATGTCCACA TCAGTAGGAGACAGGGTCAGCATCACCTGCAAGGCCAGT CAGGATGTGGGTACTGCTGTAGCCTGGTATCAACAGAAA CCAGGGCAATCTCCTAAACTACTGATTTACTGGGCATCC ACCCGGCACACTGGAGTCCCTGATCGCTTCACAGGCAGT GGATCTGGGACAGATTTCACTCTCACCATTAGCAATGTG CAGTCTGAAGACTTGGCAGATTATTTCTGTCAGCAATAT AGCAGCTATCCTCTCACGTTCGGTGCTGGGACCAAGCTG GAGCTGAAA |
| 82 | 5c9.a2 Light chain (kappa) protein | DIVMTQSHKFMSTSVGDRVSITCKASQDVGTAVAWYQQKP GQSPKLLIYWASTRHTGVPDRFTGSGSGTDFTLTISNVQSED LADYFCQQYSSYPLTFGAGTKLELK |
| 83 | 5c9.a2 mAb heavy chain HVR H1 region protein | GYTFTDYY |
| 84 | 5c9.a2 mAb heavy chain HVR H2 region protein | INPYNGGT |

TABLE 5-continued

Sequences

| SEQ ID NO: | Description | Sequence |
|---|---|---|
| 85 | 5c9.a2 mAb heavy chain HVR H3 region protein | ASLRRRTDYFDY |
| 86 | 5c9.a2 mAb kappa light chain HVR L1 region protein | QDVGTA |
| 87 | 5c9.a2 mAb kappa light chain HVR L2 region protein (WAS at residues 18-20) and flanking framework region | VAWYQQKPGQSPKLLIYWASTRHTGVPDRFTGSGSGTDFT LTISNVQSEDLADYFC |
| 88 | 5c9.a2 mAb kappa light chain HVR L3 region protein | QYSSYPLT |
| 89 | 7b6.b12 Heavy chain DNA | GAGGTGCAGCTGCAGGAGTCTGGCGCTGAGTTGGTGAAA CCTGGGAGCTTCAGTGAAGATATCCTGCAAGGTTTCTGGC TACACCTTCACTGACCATACTATTCACTGGATGAAGCAG AGGCCTGAACAGGGCCTGGAATGGATTGGATATATTTAT CCTAGAGATGGTAGTACTAAGTACAATGAGAAGTTCAAG GGCAAGGCCACATTGACTGCAGACAAATCCTCCAGCACA GCCTACATGCAGCTCAACAGCCTGACATCTGAGGACTCT GCAGTCTATTTCTGTGCAAGACCGTATGATTACGCCTGGT TTGCTTACTGGGGCCAAGGGACTCTGGTCACTGTCTCTGC AG |
| 90 | 7b6.b12 >Heavy chain Protein | EVQLQESGAELVKPGASVKISCKVSGYTFTDHTIHWMKQR PEQGLEWIGYIYPRDGSTKYNEKFKGKATLTADKSSSTAYM QLNSLTSEDSAVYFCARPYDYAWFAYWGQGTLVTVSA |
| 91 | 7b6.b12 Light chain (kappa) DNA | GACATCTTGCTGACTCAGTCTCCAGCCATCCTGTCTGTGA GTCCAGGAGAAAGAGTCAGTTTCTCCTGCAGGGCCAGTC AGAGCATTGGCACAAGCATACACTGGTATCAGCAAAGA ACAAATGGTTCTCCAAGGCTTCTCATAAAGTATGCTTCTG AGTCTATCTCTGGGATCCCTTCCAGGTTTAGTGGCAGTGG ATCAGGGACAGATTTTACTCTTAGCATCAACAGTGTGGA GTCTGAAGATATTGCAGATTATTACTGTCAACAAAGTAA TAGCTGGCCATTCACGTTCGGCTCGGGGACAAAGTTGGA AATAAAAC |
| 92 | 7b6.b12 Light chain (kappa) protein | DILLTQSPAILSVSPGERVSFSCRASQSIGTSIHWYQQRTNGS PRLLIKYASESISGIPSRFSGSGSGTDFTLSINSVESEDIADYY CQQSNSWPFTFGSGTKLEIK |
| 93 | 7b6.b12 mAb heavy chain HVR H1 region protein | GYTFTDHT |
| 94 | 7b6.b12 mAb heavy chain HVR H2 region protein | IYPRDGST |

TABLE 5-continued

Sequences

| SEQ ID NO: | Description | Sequence |
|---|---|---|
| 95 | 7b6.b12 mAb heavy chain HVR H3 region protein | ARPYDYAWFAY |
| 96 | 7b6.b12 mAb kappa light chain HVR L1 region protein | QSIGTS |
| 97 | 7b6.b12 mAb kappa light chain HVR L2 region protein (YAS at residues 18-20) and flanking framework region | IHWYQQRTNGSPRLLIKYASESISGIPSRFSGSGSGTDFTLSIN SVESEDIADYYC |
| 98 | 7b6.b12 mAb kappa light chain HVR L3 region protein | QSNSWPFT |
| 99 | amyloid-β Aβ(M1-42) | MDAEFRHDSGYEVHHQKLVFFAEDVGSNKGAIIGLMVGGV VIA |
| 100 | transthyretin (TTR) precursor [*Homo sapiens*] | MASHRLLLLCLAGLVFVSEAGPTGTGESKCPLMVKVLDAV RGSPAINVAVHVFRKAADDTWEPFASGKTSESGELHGLTTE EEFVEGIYKVEIDTKSYWKALGISPFHEHAEVVFTANDSGPR RYTIAALLSPYSYSTTAVVTNPKE |
| 101 | Mature transthyretin (TTR) [*Homo sapiens*] | GPTGTGESKCPLMVKVLDAVRGSPAINVAVHVFRKAADDT WEPFASGKTSESGELHGLTTEEEFVEGIYKVEIDTKSYWKA LGISPFHEHAEVVFTANDSGPRRYTIAALLSPYSYSTTAVVT NPKE |
| 102 | human islet amyloid polypeptide (IAPP) | MGILKLQVFLIVLSVALNHLKATPIESHQVEKRKCNTATCA TQRLANFLVHSCNNFGAILSSTNVGSNTYGKRNAVEVLKRE PLNYLPL |

Certain biological sequences referenced herein by their "NCBI Accession Number" or common names can be accessed through the National Center of Biotechnology Information on the world wide web at ncbi.nlm.nih.gov.

Various patent and non-patent publications are cited herein, the disclosures of each of which are, to the extent necessary, incorporated herein by reference in their entireties. Inclusion of these references herein is not to be construed as any admission that these references in any way anticipate or suggest the claimed subject matter of this patent application.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments.

CITED REFERENCES

1. Chiti F, Dobson C M. 2006. Protein misfolding, functional amyloid, and human disease. *Annu Rev Biochem* 75: 333-66
2. Caughey B, Lansbury P T. 2003. Protofibrils, pores, fibrils, and neurodegeneration: separating the responsible protein aggregates from the innocent bystanders. *Annu Rev Neurosci* 26: 267-98
3. Uversky V N. 2010. Mysterious oligomerization of the amyloidogenic proteins. *Febs J* 277: 2940-53
4. Lorenzo A, Razzaboni B, Weir G C, Yankner B A. 1994. Pancreatic islet cell toxicity of amylin associated with type-2 diabetes mellitus. *Nature* 368: 756-60

5. Clark A, Nilsson M R. 2004. Islet amyloid: a complication of islet dysfunction or an aetiological factor in Type 2 diabetes? *Diabetologia* 47: 157-69
6. Enoki S, Mitsukawa T, Takemura J, Nakazato M, Aburaya J, Toshimori H, Matsukara S. 1992. Plasma islet amyloid polypeptide levels in obesity, impaired glucose tolerance and non-insulin-dependent diabetes mellitus. *Diabetes Res Clin Pract* 15: 97-102
7. Kahn S E, Andrikopoulos S, Verchere C B. 1999. Islet amyloid: a long-recognized but underappreciated pathological feature of type 2 diabetes. Diabetes 48: 241-53
8. Hull R L, Westermark G T, Westermark P, Kahn S E. 2004. Islet amyloid: a critical entity in the pathogenesis of type 2 diabetes. *J Clin Endocrinol Metab* 89: 3629-43
9. Wookey P J, Lutz T A, Andrikopoulos S. 2006. Amylin in the periphery II: An updated mini-review. *Scientific World Journal* 6: 1642-55
10. Gupta R, Kapoor N, Raleigh D P, Sakmar T P. 2012. Nucleobindin 1 Caps Human Islet Amyloid Polypeptide Protofibrils to Prevent Amyloid Fibril Formation. *J Mol Biol* 421: 378-79
11. Kayed R, Head E, Sarsoza F, Saing T, Cotman C W, Necula M, Margol L, Wu J, Breydo L, Thompson J L, Rasool S, Gurlo T, Butler P, Glabe C G. 2007. Fibril specific, conformation dependent antibodies recognize a generic epitope common to amyloid fibrils and fibrillar oligomers that is absent in prefibrillar oligomers. *Mol Neurodegener* 2: 18-27.

Sample claims of various inventive aspects of the disclosed invention, not to be considered as exhaustive or limiting, all of which are fully described so as to satisfy the written description, enablement, and best mode requirement of the Patent Laws, are as follows:

What is claimed is:

1. A method for obtaining an antibody that comprises exposing a host organism or an antibody display library to a Nucleobindin 1-capped (NUCB1-capped) amyloid protofibril, and selecting an antibody from said host or said library that specifically binds at least one amyloid protofibril.

2. The method of claim 1, wherein the antibody does not specifically bind an isolated amyloid peptide monomer that is not assembled in an amyloid protofibril.

3. The method of claim 1, wherein the antibody specifically binds to two or more distinct amyloid protofibrils that are each comprised of distinct amyloid peptide monomers.

4. The method of claim 1, wherein the antibody is selected from the group consisting of a monoclonal antibody, a synthetic antibody, a chimeric antibody, a human antibody, an affinity matured antibody, a bispecific antibody, and a humanized antibody.

5. The method of claim 1, wherein said antibody is isolated by forming a hybridoma cell line with a cell from the host organism that produces the antibody and a myeloma cell line.

6. The method of claim 1, wherein said NUCB1-capped amyloid protofibril comprises an amyloid peptide selected from the group consisting of Human Islet Amyloid Poly Peptide (hIAPP), Beta 23(β23), (Transthyretin) TTR, a TTR mutant, and Amyloid Beta 42 (Aβ42).

7. The method of claim 1, wherein said NUCB1-capped amyloid protofibril comprises an amyloid peptide selected from the group consisting of TTR, a TTR mutant, and β42.

8. The method of claim 1, wherein the selected antibody binds an amyloid protofibril comprised of an amyloid peptide that is different than the NUCB1-capped amyloid peptide.

9. A method for monitoring amyloid disease in a subject that comprises contacting a sample obtained from the subject to a NUCB1-capped amyloid protofibril or to a NUCB1-capped amyloid protofibril that is covalently or non-covalently linked to a detectable label and measuring binding of the NUCB1-capped amyloid protofibril or the NUCB1-capped amyloid protofibril linked to the detectable label to endogenous anti-amyloid protofibril antibodies in the sample, wherein an increase in binding of the NUCB1-capped amyloid protofibril or the NUCB1-capped amyloid protofibril linked to the detectable label to endogenous anti-amyloid protofibril antibodies in the sample relative to a control sample, indicates an increase in endogenous anti-amyloid protofibril antibodies in said subject and amyloid disease predisposition, presence, and/or progression.

10. The method of claim 9, wherein said detectable label is selected from the group consisting of a magnetic resonance imaging (MRI) contrast agent, a radioisotope, a heterologous epitope, a fluorophore, a nanoparticle, and an enzyme.

11. The method of claim 9, wherein said NUCB1-capped amyloid protofibril comprises an amyloid peptide selected from the group consisting of hIAPP, β23, TTR, a TTR mutant, alpha-synuclein, and Aβ42.

12. The method of claim 9, wherein said NUCB1-capped amyloid protofibril comprises an amyloid peptide selected from the group consisting of TTR, a TTR mutant, and β42.

13. A method for detecting an anti-amyloid protofibril antibody in a sample comprising exposing one or more samples suspected of containing an anti-protofibril antibody to a NUCB1-capped amyloid protofibril or to a NUCB1-capped amyloid protofibril that is covalently or non-covalently linked to a detectable label and measuring binding of the NUCB1-capped amyloid protofibril or the NUCB1-capped amyloid protofibril linked to the detectable label to antibodies in the sample, wherein an increase in binding of the NUCB1-capped amyloid protofibril or the NUCB1-capped amyloid protofibril linked to the detectable label to said antibody in the sample relative to a control sample indicates the presence of an anti-amyloid protofibril antibody in said sample.

14. The method of claim 13, wherein said detectable label is selected from the group consisting of a magnetic resonance imaging (MRI) contrast agent, a radioisotope, a heterologous epitope, a fluorophore, a nanoparticle, and an enzyme.

15. The method of claim 13, wherein said NUCB1-capped amyloid protofibril comprises an amyloid peptide selected from the group consisting of hIAPP, β23, TTR, a TTR mutant, alpha-synuclein, and Aβ42.

16. The method of claim 13, wherein said NUCB1-capped amyloid protofibril comprises an amyloid peptide selected from the group consisting of TTR, a TTR mutant, and β42.

* * * * *